(12) United States Patent
Schuele et al.

(10) Patent No.: US 7,981,623 B2
(45) Date of Patent: Jul. 19, 2011

(54) REPRESSOR OF SKELETAL MUSCLE DIFFERENTIATION, NUCLEIC ACIDS CODING THEREFOR AND THE USE THEREOF IN DIAGNOSIS AND THERAPY

(75) Inventors: Roland Schuele, Weisweil (DE); Philip Hublitz, Monterotondo (IT)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 12/341,655

(22) Filed: Dec. 22, 2008

(65) Prior Publication Data
US 2009/0233317 A1 Sep. 17, 2009

Related U.S. Application Data

(62) Division of application No. 10/507,780, filed as application No. PCT/EP03/02638 on Mar. 13, 2003, now abandoned.

(30) Foreign Application Priority Data

Mar. 20, 2002 (DE) ................................. 102 12 397

(51) Int. Cl.
*G01N 33/53* (2006.01)
*G01N 33/566* (2006.01)
(52) U.S. Cl. ........................................ 435/7.1; 436/501

(58) Field of Classification Search ........................ None
See application file for complete search history.

(56) References Cited

U.S. PATENT DOCUMENTS

| 2005/0002912 A1* | 1/2005 | Chachques | 424/93.7 |
| 2007/0031395 A1* | 2/2007 | Schuele et al. | 424/94.2 |

FOREIGN PATENT DOCUMENTS

| WO | WO 00/44900 | 8/2000 |
| WO | WO 01/57190 | 8/2001 |
| WO | WO 03087768 A2 * | 10/2003 |

OTHER PUBLICATIONS

Oka et al., 2000, Arterioscler Thromb Vas. Biol. pp. 907-914.*
Punch et al., 2009, WIREs Syst Biol. Med. vol. 1: 128-140.*

* cited by examiner

*Primary Examiner* — Amy E Juedes
(74) *Attorney, Agent, or Firm* — Arent Fox LLP

(57) ABSTRACT

Polypeptide sequences which play a part in the regulation of skeletal muscle differentiation, and nucleic acids coding therefor, and the use thereof in diagnosis and therapy are disclosed. Possible uses are also indicated for antibodies which are directed against corresponding epitopes of the GRIM1 polypeptide.

10 Claims, 35 Drawing Sheets

Figure 1

```
> hsGRIM1, according to Acc.# AL050019.1, 2250 bp, 5' --> 3'
ATGGCAGCTGCGGGGAGCCGCAAGAGGCGCCTGGCGGAGCTGACGGTGGACGAGTTCCTAGCTTCGGGCTTTGAC
TCCGAGTCCGAATCCGAGTCCGAAAATTCTCCACAAGCGGAGACACGGGAAGCACGCGAGGCTGCCCGGAGTCCG
GATAAGCCGGGCGGGAGCCCCTCGGCCAGCCGGCGTAAAGGCCGTGCCTCTGAGCACAAAGACCAGCTCTCTCGG
CTGAAGGACAGAGACCCCGAGTTCTACAAGTTCCTGCAGGAGAATGACCAGAGCCTGCTAAACTTCAGCGACTCG
GACAGCTCTGAGGAGGAAGAGGGGCCGTTCCACTCCCTGCCAGATGTGCTGGAGGAAGCCAGTGAGGAGGAGGAT
GGAGCGGAGGAAGGAGAAGATGGGGACAGAGTCCCCAGAGGGCTGAAGGGCAAGAAGAATTCTGTTCCTGTGACC
GTCGCCATGGTTGAGAGATGGAAGCAGGCAGCAAAGCAACGCCTCACTCCAAAGCTGTTCCATGAAGTGGTACAG
GCGTTCCGAGCAGCTGTGGCCACCACCCGAGGGGACCAGGAAAGTGCTGAGGCCAACAAATTCCAGGTCACGGAC
AGTGCTGCATTCAATGCTCTGGTTACCTTCTGCATCAGAGACCTCATTGGCTGTCTCCAGAAGCTGCTGTTTGGA
AAGGTGGCAAAGGATAGCAGCAGGATGCTGCAGCCGTCCAGCAGCCCGCTCTGGGGGAAGCTTCGTGTGGACATC
AAGGCTTACCTGGGCTCGGCCATACAGCTGGTGTCCTGTCTGTCGGAGACGACGGTGTTGGCGGCCGTGCTGCGG
CACATCAGCGTGCTGGTGCCCTGCTTCCTGACCTTCCCCAAGCAGTGCCGCATGCTGCTCAAGAGAATGGTGGTC
GTATGGAGCACTGGGGAGGAGTCTCTGCGGGTGCTGGCTTTCCTGGTCCTCAGCAGAGTCTGCCGGCACAAGAAG
GACACTTTCCTTGGCCCCGTCCTCAAGCAAATGTACATCACGTATGTGAGGAACTGCAAGTTCACCTCGCCTGGT
GCCCTCCCCTTCATCAGTTTCATGCAGTGGACCTTGACGGAGCTGCTGGCCCTGGAGCCGGGTGTGGCCTACCAG
CACGCCTTCCTCTACATCCGCCAGCTCGCCATACACCTGCGCAACGCCATGACCACCCGCAAGAAGGAAACATAC
CAGTCTGTGTACAACTGGCAGTATGTGCACTGCCTCTTCCTGTGGTGCCGGGTCCTGAGCACTGCGGGCCCCAGC
GAAGCCCTCCAGCCCTTGGTCTACCCCCTTGCCCAAGTCATCATTGGCTGTATCAAGCTCATCCCCACTGCCCGC
TTCTACCCGCTGCGAATGCACTGCATCCGTGCCCTGACGCTGCTCTCGGGGAGCTGGGGGCCTTCATCCCGGTG
CTGCCTTTCATCCTGGAGATGTTCCAGCAGGTCGACTTCAACAGGAAGCCAGGGCGCATGAGCTCCAAGCCCATC
AACTTCTCCGTGATCCTGAAGCTGTCCAATGTCAACCTGCAGGAGAAGGCGTACCGGACGGCCTGGTGGAGCAG
CTGTACGACCTCACCCTGGAGTACCTGCACAGCCAGGCACACTGCATCGGCTTCCCGGAGCTGGTGCTGCCTGTG
GTCCTGCAGCTGAAGTCGTTCCTCCGGGAGTGCAAGGTGGCCAACTACTGCCGGCAGGTGCAGCAGCTGCTTGGG
AAGGTTCAGGAGAACTCGGCATACATCTGCAGCCGCCGCCAGAGGGTTTCCTTCGGCGTCTCTGAGCAGCAGGCA
GTGGAAGCCTGGGAGAAGCTGACCCGGGAAGAGGGGACACCCTTGACCTTGTACTACAGCCACTGGCGCAAGCTG
CGTGACCGGGAGATCCAGCTGGAGATCAGTGGCAAAGAGCGGCTGGAAGACCTGAACTTCCCTGAGATCAAACGA
ACGAAGATGGCTGACAGGAAGGATGAGGACAGGAAGCAATTTAAAGACCTCTTTGACCTGAACAGCTCTGAAGAG
GACGACACCGAGGGATTCTCGGAGAGAGGGATACTGAGGCCCCTGAGCACTCGGCATGGGGTGGAAGACGATGAA
GAGGACGAGGAGGAGGGCGAGGAGGACAGCAGCAACTCGGAGGATGGAGACCCAGACGCAGAGGCGGGGCTGGCC
CCTGGGGAGCTGCAGCAGCTGGCCCAGGGGCCGGAGGACGAGCTGGAGGATCTGCAGCTCTCAGAGGACGACTGA
```

Figure 2

```
> mmGRIM1, calculated cDNA sequence, 2253 bp, 5' --> 3'
ATGGCTGCGTCTCGCGCTCCCCGCAGGCGCCTGGAGGACCTCAGTGTGGACGAGTTCCTGGCTTCCGGCTTCGAG
TCCGGATCCGAGTCGGAGCTGGAGGGCGCCGCGGAGGCGGCGGCGGAGGAGCGCAGGGCGCGAGGAGCCGCGTGG
AACCGGGAGCGGCGGGGCGCGCGCACCTCCCCGGGCCCCGCAGGACGCCCGCGTAAGGGCCGCGCCTCTGAGCAC
AAAGACCAGCTCTCTCGGCTGAAGGACAGAGACCCCGAGTTCTACAAGTTCCTGCAGGAGAATGACCGGAGCCTA
CTGGACTTCAGTGACTCGGACAGCTCTGCGGAAGAAGAAGAGCCATTCCACTCCCTGCCAGACACGCTGGAGGAA
GCGAGCGAAACAGAGGAAGACGGAGGAGAGGACAGTGACGCGTTGCCCAGAGGGCTGAGGAGCAAGAAGAATGAG
CCTGTACCCGTGACCCTCGCCATGGTGGAAAGGTGGAGGCAGGGCTCCAGGCACCACCTTAGTCCCAGGCTGTTC
CATGAAGTTGTACAGGCGTTCCGAGCAGCTGTAGCCACCACCCAAGGAGAGCAGGAAGCTGCTGAGACTTGCAGG
TTCCAGGTTGCAGATAGTGCTGTGTTCAATGCTCTGGTTACTTTCTGCATTCGAGACCTCTGTGGTTGCCTTCAG
AAGCTGCTGTTTGGAAAGACACCAAAGGATAGCAATAGGCTGCTGCCATCCAGTAGCCCACTGTGGGGGAAGCTC
CGTGTGGATGTCAAGACATACCTAAGTGCGGTGTGCAGCTGGTAGCCTGTCTAGCGGAAGCCACAGTGTCTGCA
GCTGTCCTGCAGCATATCAGCAGCTTGGTTCCTTACTTCCTGACTTTCCCGAAGCAGTGCCGAATGCTGCTCAAG
AGGATGGTGGTTCTGTGGAGCACGGGTGAAGAGTCTCTGCGGGTCCTGGCCTTCCTGGTACTCATCAGAGTCTGT
CGGCACAAGAAGGAAGCCTTCCTTGGTCCCATTCTGAAGCAAATGTACATCATGTATGTGAGAAACTGCAAGTTC
ACCTCCCCCAGTACCCTCCCCCCTCATAAGCTTCATGCAGCGGACACTGACTGAAATGCTTGCCTTGGACCCCAGC
GTCTCCTATCAGCACGCCTTCCTCTACATCCGCCAGCTTGCCGTCCACCTGCGGAATGCTATGACCACAGGCAAG
AAGGAGACACACCAGTCTGTGTACAACTGGCAGTATGTGCACTGCCTCTACCTGTGGTGTCGWGTCCTGAGTACC
CTTGGTTCCAGTGAGATCCTGCAGCCGCTACTCTACCCTCTCTCACAGATCATCATTGGCTGTATCAAGTTGTTG
CCCACTGCTCGATTTTATCCATTGCGCATGCATTGTGTACGTGCCCTGACACTGCTGTCCCAGACCATCGGCACC
TTCATACCTGTCCTGCCCTTCATTCTYGAGATTTTCCAGCAGGTGGACTTCAATAGGCGGCCAGGTCGCATGAGC
TCCAAGCCCATCAACTTCTCTGTGATCTTGAAGCTGTCCAGCACCAACCTGCAGGAGAAGGCGTACCGGGACGGG
CTGCTGGAACAGCTGTGTGACCTTACTCTGGAATACTGCACAGCCAGGCCCACAGCATCGCTTTCCCAGAGTTG
GTGTTGCCTACTGTTCTACAGCTGAAATCTTTTCTCCGGGAGTGCAAAGTGGCTAACTACTGCCGGCAGGTGCGC
CACTMGCTGGAGAAAGTGCAAGAGAATGCACAACATATCCAAAGTCTTCGACAGAGCGCGACCTTCAGCGTGTCT
GACCGGACGGCAGTGGATGCGTGGAGAAGCAGGTTYGTGAAGAGGGGACCCCACTCACCAGATACTACGGCCAC
TGGAAGAAGCTGAGGGACCGTGAAATCCAGCTGGAAATCAGTGGCAAAGAGCGGCTAGAAGACCTGAACTTCCCA
GAGATCAAAAGGCGGAAGGTGGAAGACAGGAAGGATGAAGACAGGAAAGAATTAAAGGACCTGTTTGAGTTGGAC
AGTTCTGAGGGCGAGGACAGCACCGACTTCTTTGAGAGAGGAGTACCTAGGCTCCCAGAAGCTCACCAAGGACTG
AAAGAAGATCAGGAAGAAGAAGATAAAGAAGAAGGTGACAGCGATTCAGAGGATGGAGACACAGACACGGGAGTG
GATCTGAGCGAACTGTGGCAGCTGGCTCAGGGACCACAAGATGAGCTGGAGGATCTTCAGCTCTCAGAAGAGGAC
TGA
```

```
PREDICTPROTEIN: MaxHom-db

1 [                         .         .         :         . 60
    mmGRIM1      MAASRAPRRRLEDLSVDEFLASGFESGSESELEGAAEAAAEERRARGAAWNRERRGARTS
    hsGRIM1      MAAAGSRKRRLAELTVDEFLASGFDSESESESENSPQ--AETREAREAARSPDKPGGSPS
    yu20_drome   ---------------DAIRKTKPQTTSETKVTP--------RNPKQKVAEPVKNGKTT-
    yo26_yeast   -AAGTREQQQLkdMSVETFFEKGIEIPKENKKLKKKT-------------TKEQSDEDSS
    ytb2_caeel   -AGLKKRKVISKRIKIEKKPSSEDEGSSDEEVPKLDG-------------EGSLDGSEDE
    yu20_arath   MGA-----KELKGFEIDKHFKSNVDDKKRVKKLKSKKLEAEEELNNVQEIDamEQKSDKK 61                         .         .         :         . 120
    mmGRIM1      PGPAGRPRKGRASEHKDQLSRLKDRDPEFYKFLQENDRSLLDFSDSDSSAEEEEPFHSLP
    hsGRIM1      ----ASRRKGRASEHKDQLSRLKDRDPEFYKFLQENDQSLLNFSDSDSSEEEEGPFHSLP
    yu20_drome   -------KKGFKKSHKEELEGLKDIDPEFYDFLKNNDKKLLDFndTDDDDDEEGDEEDKE
    yo26_yeast   -------SSEEEEDMGQSMAKLAEKDPEFYKYLEENDKDLLDFAGTNPlsQDEGEDAERN
    ytb2_caeel   DDGTVTVEKGGVKKHKLDLEKLKQSDPEFFKFLQQEDADLLNMEDDGDDDEDDDEDDE--
    yu20_arath   RGKKVKSKKAEAEEHEEELKRLQEKDPDFFQYMKEHDAELLKFDATEIEDDADVE----P 121                         .         .         :         . 180
    mmGRIM1      DTLEEASETEEDGGEDSDALPRGLRSKKNEPVPVTLAMVERWRQGSRHHLSPRLFHEVVQ
    hsGRIM1      DVLEEASEEEDGagEDGDRVPRGLKGKKNS-VPVTVAMVERWKQAAKQRLTPKLFHEVVQ
    yu20_drome   DTVTKESKDDEDDEEKYHKPSKDLEVASDEsqKITLNLLHQWEQQlqANISIDIVRKVIQ
    yo26_yeast   SNIEEKSEQMELEKEKIE---------------LSLKLVRKWKKQLHDSPSLKLLRNIIS
    ytb2_caeel   DEEEEESDDDEDDEEDDDkrKPKIKSDNSGRLIVDSNVYSYLQQVlsTPTNPSDVRMAVD
    yu20_arath   DTDLEDTEKEGDDEATKMEIAKKVHVQKT----ITASMVDAWSKSIEDEAKLGGVRSILR 181                         .         .         :         . 240
    mmGRIM1      AFRAAVATTQGEQEAAETCRFQVADSAVFNALVTFCIRDLCGCLQKLLFGKTPKDSNRLL
    hsGRIM1      AFQAAVATTRGDQESAEANKFQVTDSAAFNALVTFCIRDLIGCLQKLLFGKVAKDSSRMl
    yu20_drome   AFNSALASIsgGENKHNAAAFKVVGAAAFNGVIQLCVIHLQPAIIRLLGVR---PNSSLP
    yo26_yeast   AFKVAVNLN--KEENIEDYKYAITDEKAFHELMFMVLKDVPQAIQKMAPYKIVKGARTLP
    ytb2_caeel   VFVACVARVGADIEAPK---YVINEQSIFEAVVRMCFQAMPDILKRLLKAKPEGDKVLF-
    yu20_arath   AYRTACHYGDDTGDDQST-KFSVMSSEVFNKIMIYVLSEMDGILRKLLRFPegTKETILE consensus/80%   sa.ssht....t.pt.p...a.1.ttthFptlh.hsh.th..hl.+hh.h......t..h.
    consensus/70%   AFpsAlshstspt-s.ps.tatlssptsFptlhhhslpch.shlp+LLhh+..tspshh.

241                         .         .         :         . 300
    mmGRIM1      PSSSPLWGKLRVDVKTYLSAVVQLVACLAEATVSAAVLQHISSLVPYFLTFPKQCRMLLK
    hsGRIM1      PSSSPLWGKLRVDIKAYLGSAIQLVSCLSETTVLAAVLRHISVLVPCFLTFPKQCRMLLK
    yu20_drome   LHKHKKWVKVRGCLRYYLTDLIRLVEQVSSPNILGVLLKHLHQMAGMVVPFSALGKTILK
    yo26_yeast   --NGGNVSRVSSIVKSHAGSLLILLNDITNTETAALVLHSVNELMPYLLSYRRILKELIK
    ytb2_caeel   --SKTAIKKYQTYVRTYLHAMIVFLNEVQTTEVLIATIKAMTRLVDLYAHFSRMSKLLIK
    yu20_arath   LTNTRPWKNYNHLVKSYLGNSLHVLNQMTDTEMITFTLRRLKHSSVFLAAFPSLLRKYIK consensus/80%   ..pt..h.php..l+.ahts.l.hltphtpsph.hhhlptnp...shhh.a.t..+.hlK
    consensus/70%   ..sp..ht+hps.l+sYLsshl.llsplspsphhshsL+plpphsshhhsFsp.h+llK 301                         .         .         :         . 360
    mmGRIM1      RMVVLWSTGEESLRVLAFLVLIRVCRHKKEAFLGPILKQMYIMYVRNCKFTSPSTLPLIS
    hsGRIM1      RMVVVWSTGEESLRVLAFLVLSRVCRHKKDTFLGPVLKQMYITYVRNCEFTSPGALPFIS
    yu20_drome   RLVVLWSTGDETVRVLAFLCILKITRKQQATMLNHVLKAMYLAYVRNSKFVSPNTLPGIN
    yo26_yeast   SIVGVWSTTRElQIASFAFLINTTKEFKKSMLETTLKTTYSTFIKSCRKTNMRSMPLIN
    ytb2_caeel   AVVRIWSRKTLECRLPAFVCMNLLVKNYPQHFV-PLYKTAYVAFVANSKIVTNETWPLLQ
    yu20_arath   VALHFWGTGSGALPVVSLLFLRDLCIRLGSDCVDDCFKGMYKAYVLNCQFVNADKLKHIS consensus/80%   .hlhhWuptp..h.l.uhhhh..hshp...tthl..hhKthY.halhsephss.tth.hlp
    consensus/70%   thVhlWSTspthplhuFlhl.pls+chtpshltshhKthYhsaVtNschssspshPhIs 361                         .         .         :         . 420
    mmGRIM1      FMQRTLTEMLALDPSVSYQHAFLYIRQLAVHLRNAMTTGKKETHQSVYNWQYVHCLYLWC
    hsGRIM1      FMQWTLTELLALEPGVAYQHAFLYIRQLAIHLRNAMTTRKKETYQSVYNWQYVHCLFLWC
    yu20_drome   FMRRSLVEMFALDLNVSYQHVFLYIRQLAIHLRNAVILKKKDSFQAVYNWQFINSLRLWA
    yo26_yeast   FQKNSAAELFGIDEVLGYQVGFEYIRQLAIHLRNTMNanSAEAYKIVYNWQFCHSLDPWS
    ytb2_caeel   FMHRTFAELTILNPEQAYKYAFVYIRQTAVHLRNAMIsgRKDLIFSIYNWQMMQCMYMWV
    yu20_arath   FLGNCFIELLGTDISAAYQHAFVFIRQLAMILREALNTKTKEAFRKVYQWKFIHCLELWT
```

FIG. 4 Cont'd

```
consensus/80%    F.t.shhEhhhhp...uYphsF.aIRQhAhhLRpsh..tpt-.h..lYpWphhpsh.hWs
consensus/70%    FhppohsEhhul-.shuYQauFlYIRQLAlHLRNAh.stpK-saptVYNWQahpsL.hWs 421                         :                      .  480
mmGRIM1          RVLSTLGSSEILQPLLYPLSQIIIGCIKLLPTARFYPLRMHCVRALTLLSQTIGTFIPVL
hsGRIM1          RVLSTAGPSEALQPLVYPLAQVIIGCIKLIPTARFYPLRMHCIRALTLLSGSSGAFIPVL
yu20_drome       DLLGASANKPQLQPLIYPLVTIATGVIRLIPTAQYFPLRFHCLQTLISLAKETNTYVPVL
yo26_yeast       RVLSFagSESPLRQLIYPLVQVTLGVIRLIPTPQFFPLRFYLIKSLIRLSQNSGVFIPIY
ytb2_caeel       RVIAKAHsaEQIGELVYPLIQVIVGIFKLCNAPTFLPLRLHCCQLLIQLQASCTNYIPIL
yu20_arath       GAVCAYSSQSELRPVAYPLAQIITGVARLVPTARYTPLRLRCVRMLNRLAAATGTFIPVS consensus/80%    thlsh.tst..lt.lhYPL.plhhGhh+LhssspahPLRhhhhp.L..Lttt.ssalPl.
consensus/70%    clluthuspp.Lp.LlYPLsQlhhGsh+LlPTspahPLRh+ClphLh.LutssssaIPlh 481                         .                      .  540
mmGRIM1          PFILEIFQQVDFNRRPGRMSSKPINFSVILKLSSTNLQEKAYRDGLLEQLCDLTLEYLHS
hsGRIM1          PFILEMFQQVDFNRKPGRMSSKPINFSVILKLSNVNLQEKAYRDGLVEQLYDLTLEYLHS
yu20_drome       PLIVEVLKSNTFNRKHSAVSMKPVQFTCVLRLNKGQLAENGFRDEVIEQVCGLLLEYLAH
yo26_yeast       PLLSEILTSTAFTKAPKkpNLAAFDPEHNIKCTQAYLNTKIYQEGLSEQFVDLLGDYFAL
ytb2_caeel       QVSCDCLEElkSKPKPVKGAVKLPDIECTLKCSSQFSDLPQWRKVISEHVFRTMMQSAHL
yu20_arath       MLLVDMLEMKELNRPPTGGVGKGVDLRTLLKVSKPAVKTRAFQEACVYTVVEELVEHLSQ consensus/100%   .....hhp..t.p....t.s.t..phph.l+hsp...t...apc.h..phht.hhp.ht.
consensus/90%    .....hhp..t.p....t.s.t..phph.l+hsp...t...apc.h..phht.hhp.ht.
consensus/80%    .h..-hhpphphs+tPsths.KshshpshLKhops.lppptap-sl.Eplhchhh-aht.
consensus/70%    .hlh-hhppscFNR+Ps+husKslsFpslLKlSpstLpp+uaR-ullEQls-LhlEYLpp 541                         .                      .  600
mmGRIM1          QAHSIAFPELVLPTVLQLKSFLRECKVANYCRQVRHXLEKVQENAQHIQSLRQSATFSVS
hsGRIM1          QAHCIGFPELVLPVVLQLKSFLRECKVANYCRQVQQLLGKVQENSAYICSRRQRVSFGVS
yu20_drome       ESTSLAFSDLVVPTVMAIKTYLKECRNANYARKLKQLLEKIQESARFIEQQRGKStFDIK
yo26_yeast       YCKNIAFPELVTPVIISLRRYIKTSTNVKLNKRLSTVVEKLNQNSTFIQEKRSDVEFGPT
ytb2_caeel       LASQAAFPDVVLPINHRISAILETMKNGDHAHLFRGFQTKLKEHSRFVLDVLARKSVDIN
yu20_arath       WSCSVAFFELSFIPTIRLRSFCKSTKAERFRKEMKQLISQIEANSEFVNKKRALIKFLPN consensus/100%   .spphuF,-lsh...htlpthhcp.ps.pht+.hpt..tplptputal.p.ht..ph..p
consensus/90%    .spphuF.-lsh...htlpthhcp.ps.pht+.hpt..tplptputal.p.ht..ph..p
consensus/80%    .upslAFs-LVhPsshpl+sal+ps+sspas+phpphlpKlppsupalpphRthphpFs.s
consensus/70%    .upslAFPELVlPsllpL+oaL+psKsusas+pl+pllpKlpENupalpphRtpsoFsls 601                         .                      .  660
mmGRIM1          DRTAVDAWEKQVXEEGTPLTRYYGHWKKLRDREIQLEISGKERLEDLNFPEIKRRKVEDR
hsGRIM1          EQQAVEAWEKLTREEGTPLTLYYSHWRKLRDREIQLEISGKERLEDLNFPEIKRRKMADR
yu20_drome       DAQAVAAWEQQLRLKRTPLDVYYASWLKTHETKKRRQAAHTDEiaDYDVPKLKKLPvtGV
yo26_yeast       NKSEVSRFLNDVAWNKTPLGSYVAVQREVKEEKARL-----------+-MRESMEEQD
ytb2_caeel       DEMQVRAVRFDLNNHDSPIKTFYRQWEKVWKMK------------------ERSAVENS
yu20_arath       DLAAESFLEDEKKAGKTPLLQYAEIIRQRAQQRNESLVESDVIVGENSAVPGKNAP---- consensus/100%   p..t.thh...h..ttoPl..aht...phhp.c..................cp......
consensus/90%    p..t.thh...h..ttoPl..aht...phhp.c..................cp......
consensus/80%    -tttVpthcppht.ptTPLt.Yht.hcchtcpc.p...............h+ct..tt.
consensus/70%    DppAVsAaEpplptctTPLspYYupW+Kl+-pchph.http..lt-.shs.hK+phhpsp 661                         "                      ,  720
mmGRIM1          KDEDRKELKDLFELDSSEGEDSTDFFERGVPRLPEAHQGLKEDQEEEDKEEGDSDSEDGD
hsGRIM1          KDEDRKQFKDLFDLNSSEEDDTEGFSERGILRPLSTRHGVEDDEEDEegEEDSSNSEDGD
yu20_drome       PVRNENGEVELFPSDSEDEGDD------------GLHLGSDDDDDEDVQEEEEVEVEHPK
yo26_yeast       KERETEEAKLLNSLESDDDNEDVEMSD---------------------------------
ytb2_caeel       KKDDKKK--------KKEEEAA------------AAKKRKPNETVEDEDDVKPEVSKAK
yu20_arath       ---------------SSDDEDDEDRMEKGAAAFNSSWLPGSDSKEKEPEEEKTKKKKRKR consensus/100%   ...............pp-ttts......................................
consensus/90%    ...............pp-ttts......................................
consensus/80%    ..cpppt........Sp-tp-s..............h...p.spp.-..t---p.p.pc.c
consensus/70%    Kcc-ccp.h.L...pSs---Ds.th.-........tst.shc-sp-cEspEEtpscsccsc 721              ] 750
mmGRIM1          TDTGVDLSELWQLAQGPQDELEDLQLSEED
hsGRIM1          PDAEAGLaeLQQLAQGPEDELEDLQLSEDD
yu20_drome       AKKaaTVEDDYDEAGGAVDIVKDLDLNE--
yo26_yeast       ------------------------------
ytb2_caeel       RKRIKIGAAAKKADASVPDQFADMSMWSDE
```

FIG. 4 Cont'd

```
yu20_arath      GGKSKTEKKQDEQGLGEDDVVEDFVLSSDE consensus/80%   .tt.h..tt..p.s.u..D.htDh.h.p..
consensus/70%   scpthshtc..p.utGs.D.lcDhpLsp--
```

Figure 5 human GRIM1 genomic DNA
>gi|17434913:c742700-727596,
NT_025635
DKFZ-clone AL050019.1, GI 4884087

GGCGGCGGAAGTGCGCAGCCGCGCGGCATTCTGGGGCCGGAAGTGGGGTGCACGCTTCGGGTTGGTGTCA
TGGCAGCTGGGGAGCTGCAAGAGGTAAGCCGCGGGTCCGAGGGCCGATTTGGCCTCCCGGTGGGTGTC
TGTATCCAAGGGGGCTTTTCTTGCTCCTCTCAACGGGGCTTGGGCCAACTTGGCCTTCCGGCCACTTTGA
CTTCTTCCTTAACCGCAGGCGGCTGGCGGAGCTGAGGGTGGACGAGTTCCTAGCTTCGGGCTTGATCC
CAGTCCGAATCGGAGTCCGAAAAATTCTCCACAAGCGGAGACACGGGAAGCACGGGAGGCTGCCCGGAGTC
CGGATAAGCCGGCGGGAGCCCCTCGGCCAGGTTAGTGGGGACATGCGTGAGCAGAACCTCTTGCTCGTC
CTGTCCCACCCCGGTTGGGTTGCTGACCTCGCCTGGGGTCTCAGGGCCAAGGCCTAAGGATCGCCGACCT
CTGCCCCCCAGTCCTTTCAGCTTAACTTACTCTTTCATCCGATGTTTACTGAGCTCCTGTTCCGTGCCAA
ACTCTGTCCTAGGCAGGGAGCGTATGTTGGTGAGTTGTGCAAAAATCTCTTCCCGATCTAGGAGAACTCT
CACGTTCTTGGGTGAAATCACCGCCTGCAGTTCGGTAGAAGAGAGATAAGTGCTGGGGAGGGAAAGGAAG
GACAGAGGGGCTGAAGAGAGAGTTGCAGGGGAGCCGAGTTGCTCTGTTAGAAGGAGCGGAGGCTGTGCTC
GGTGGCTCACGCCTGTAATGCCAGCACTTTGGGAGGCCGAGGCGGGCAGATTACCTGAGGTCAGGAATTC
GAGACCAGCCTGACCAACACGGAAAAATCATGTCTCTACTAAAAATATAAAAATTAGCCGGGCGTGGTGG
GCACCTGTAATCCCAACTACTCGGGAGGCTGAGGCAGGAGAATCGCTTGAACTTGGGAGGCGGAGGTTGC
AGTGAGCCGAGATGGCACCATTGCATTCCAGCCTGGGTGAGAGAGTGAGACTCCATCTCAAAAAGAAAAA
GAAAGAAATCAAAAGATACAAAAATTAGCCTGGCGTGGTGACACACACCTGTCGTCCCAGCTACTCGGGA
GGCTGAGGCAGGAGAATCGCTTGAACCCGGGAGGCGGAGGTTGCGGTGAGTGGAGATTGCGCCACTGCAC
TCCAGCCTGGGCGACAGAGTGAGATTCCGCCTCGAACAAGGAGGCCACACAGACAGTAGGGGAAACGTGTC
TTAGGATTTCAGGCAGCAGAAAACAGCAAAAGCCTTGCAGTGGGAGCATTTGGGGAGAGTACAGAGGTAA
ACGTGGCTACGGCAGGAGTGAGGGGGTGAATAGGGGTAGATGAGCCCAGAAGGGTGATGAAGAGCCAGGT
GCCGTAGACCGTCATAAGATTGCCTCGTAAAACAGGGAGTTACTTCTGGGTTTGAGCGGTGGAGTGCCTT
GTAGGTGACAAGGGTGGAAACAGAGAGACCCTTTAGGTTAACTGAGAATTGAACTATGTGGTGGTTTGAGA
GGAGGCACGAACGGTTTTGAAGGTGTTGCTGATGAGATCTGATGACAAGTTGCGTGCTGGGTATTAGAGA
CAGAGATTTGCCTTTAGTCTGAGCCTCTGGAAGGGTGAAGCCACCATCAGGCAAAAGTAGCGCAGGGCAC
AGGCACAGCAAGTCCAGGGAAGACCGCGGCTGGGGGCCTGTGTAGCGCAGGGCGCAGGCACAGCAAGTCC
AGGGAAGACCGCGGCTGGGGGGCCTGTGTAGTGTGTTTGAGGGTATGTTGTAGAGGTTGTTGGGTAGGAG
ACGTGAGTCTGCCAAAAACGTACCTCCTGGCAATCCTGTCTTGCTAGTTGGTAACCCTTGTGAAGGGAGT
AGACTGACCCTGTAGGCCACTCCCCGCCCCCTCTACTTCCACTTCCCACTGGGGTCGCTGACTTCTGCCT
CCTCAGCCGGCGTAAAGGCCGTGCCTCTGAGCACAAAGAGCAGCTCTCTCGGCTGAAGGACAGAGACCCC
GAGTTCTACAAGTTCCTGCAGGAGAATGAGCAGAGCCTGCTAAAGTTCAGCGACTCGGACAGCTGTGAGG
AGGAAGAGGGCCGTTCCACTCCCTGCCAGATGTGCTGGAGGTGAGGGCGTGGGCCAAACCAGAAGGGGG
GCACTTGTCTCTACACTCTCCTTCAGCTCAGCAGTGTCTGTGCAGGAAGCCAGTGAGGAGGAGGATGGAGC
GGAGGAAGGAGAAGATGGGACAGAGTGCCCAGAGGCTGAAGGGGAAGAAGAATTCTGTTGCTGTGACC
GTCGCCATGGTTGAGAGATGGAAGCAGCCAGCAAGGTGAGCAGCAGCCAGGGGCGGGCAGCTGGGTGCC
CAGGCAGAAATCTGGCCTTGCCTCACCTGAGGTGAGCAGCAGCGAGGGCGGGCAGCTGGGTGCCCAGGC
AGAGATCTGGCCTTGCCTCACCTGAGGCGCCTGAGGCTGTGCTGGTGGGAGGGCTGTTCTCCACGCAGG
GGACGCTTGGAGCCTTCTTCAGCGCAAGTGACAACACGTTGCTCCTCCTGCTTGCTTGGTTGCCCCAGGA
CTGTGTGTTCACTTTTGGGTAGATTCCAGGGGCTCTGTTGGCGCCCCACTCCCCAAAGTCAGTCCCGCTG
TGGGTGGGACGGACTGTGCCTTTGTTGGTTGGTGGAGCTGGGGTCCTTCTGAGCCTCTCACAGTGTTTTT
TTCCAGGGACAAGGATACGGAGAGCTCCAGATACCACCTGGAGGTGGCCATAGTCCAGGATCTGGAACTC
CCAGTCCTTTTCCTGGGGCTCCTGAGCCAGACTCCCTCCTCTTCCCAGAGAATTCTAGACTTTGTTTCCA
TTTTTGTTATCAGTATGGGGCTCTGTGCCTCCCCCCAACCTCTGCCCTATGTCTGAGGGTGAGGGTGAGG
GTGCCTTTCTCTGGGGCTGCCGTTTCCACTCTGCCAAGTGCAGTCTCAGCTCCCCTGACGCCCTGGTAC
TCTTGCTCCTTCAGCAACGCCTCACTCCAAAGGTGTTCCATGAAGTGGTAGAGGCTTGGAGGCAGCTGT
GGCCAGCACCCGAGGGGACCAGGAAAGTGCTGAGGCCAACAAATTCCAGGTCACGGACAGTGCTGGTGAG
CTTGGGGGGAGCCTGGCATCCAGGCTGTCTGTTGCGTTCTCTGTCCCGTGAGTACATCCAGGCCTTTTCG
TTGCAGCATTCAATGCTCTGGTTACCTTGTGGAATGCAGACAGTTGGCGTCTCCAGAAGCTGCTGTT
TGGAAAGGTGGCAAAGGATAGCAGCAGGTAAGAGGGGAGGGGGTGAAGGGGGTAGGGTGGAAGGTGGGT
CGGGACCACACACAGGAGAAGCCAGAGGCCTTGTGGCTAGGACAGAGACATGGCAACAGAGCCAGCGTCT

FIG. 5 Cont'd

```
TCTTGGGGACCCTGAGAAGGCAGCGGGGCACGAGGGACCGTTGGGAGAGGCTGGGCACTTGGGGCCAGTT
GGAGCGGCCCCACCTTCTTTCCTTCCTGAAAAGGGAAGTTGTCTGCTCAGAGTCTCAGAAGGTGTGGCGT
GTGCAGCTGCCTTTGCTCTCAGATTTTCCCAGGTTAGGGTTCTTGCTCTATTTCCCTTTGTAAGAACTTG
TAAGTCCTGTCCATACTCCTTGATCTCTGCACTATGACTGGCCTGTTTCCTGGAGCTGTGTGTGTCTGTA
GACAGGGGCCTCATCAATGCTGAGAACCTGAGGGCCTCAACTTCCCCTTTAGAGAAAGATTGGGCAGAGA
AGGCCGTGGAAGGTTTTCAGAGAAGAGAGACGCACGGCCAAGCATTTGGTAGAGCATGGAGCACGTTGGG
GTTCCGGGGCTGTGCAGCCATGTGACCTTGAGGCAGTGGAGGCCTAGAGTTGGAACTGCCCCAGGACACC
TTCAAAGGAAGAAAGGAGACCCACAGGAGAGGTCTCGCCGACAGCGGCTCAGGAGACAGGGGCACTGTTG
CTGGTGGTAGTGGTCGGGGCTGGACGGATAGAACAGAGCCATGTCCACATGGAGGCAGTGCTGTCCGAAG
GGGACAAGGAAGCTGGCAGATGGGGGTGGAGGGACAGGCAGCGATTGGGAGGCAGCACGCACTGCAGCCT
GAGCCACCAGGTCAGGGACCCCTGTCGAGGCAGCAGCTGTACCGGAGGGAGTCAGGCCGTGGGGAGCAGA
GCTGCCTCCTGGGTCTGGGTGGGCAGCTGCAGGTGCCCAGCAGCCAGTGTCAGCACAGGTGTGAGGAGGG
TCGAGGACGGGGGGCCTTTCTGGGGCCCTGCCCTTTGTCCTTCCCATGCTTCAGCAGATTTTAGTGAGCG
CCTACTGCGTGGGCTCTGGTAAATGTTTTGTTTTGTTTTGTTTTGTTTTGTTTGGTTTTTGGTTTTTTTT
TTCCTTACGAGATAGGATCTTGCTCTGTCGCCCAGGCTGGAATGCAGTGATCATAGCTCACTGCGACACG
TACCTTCTGGATTCAAGTGATTCTCTCACCTTAGCCTCCCAAGTAACTGGGACTCCGCCACCAGGCCTGG
ATAATATTTTGTATATTTTTGTAGAGACGGGGTCTCACTGTGTTGTTCAGGCTGGTCTCAAACTCCTGGG
CTTGGAGTTTGATCCTCCTGCCTTGGCCTCCCAAAGTGCAGTGAGTACTGGCATGAGTCTCCACACCTGC
CCTCTGATTTTCTTTTCTTTGTGCAGCAAATGTGGGCCAAAGGAAACCAGTCTGCGGCAGTTGGTGGTGC
CTGGGCGACCCCAGAGGTGCTGAGTACCAGCTGCTGGGCTTAGGGACCTCGTGTGGTCTCACGGTGGGGA
TGTGATCAAGGGGACCTAGAAAAGGTTTATGTCTGAGAGGGAGTTGGAGGCTGGGACTTCCGGGGACTCT
TAGGGCGGTGGCCAACCCTGGGCAGGGCAGACAGGAGTTCAAGGCCACTGAAGGAGGAGCTAATGCACTT
GAGAGGGTCCTCCTAAGCCCCTGTGTCTGTCCAGCTGTAAGGGGCCCTGAGCTTTTTTGAGTGGAGAGAC
GGGGGGTCTCTGCAGAGTCGTAGAGGCTATGCTGGCCAGGGCACGCGCCAACATGCTGAGCAGCCTCGCG
TCCGAGCCGTGGGGCCTCCCAGCCAGGGGTGGGTGGTCTCTCTGCAGGATGCTGCAGGCGTCGAGCAGCG
CGCTCTGGGGAAGCTTCGTGTGGACATCAAGGCTTACCTGGCTCGGCCATACAGGTGCTATTCTGGTG
GGGAGGGCACGGGGGCCTGGCTGTATCTGGTGGTCGGTCCTTTTTTGTATCCCAGAATACATGGGTTTGG
GGCTTCACTGTCCCCTCCTGCCCCCAGCTGGTGTCCTGTCTGTCGGAGACGACGGTGTTGCCGGCCGTGG
TGCGGCACATCAGCGTGCTGGTGGGCTGCTTCCTGACCTTCCCCAAGGAGTCCGGATGCTGCTCAAGGT
TCGTGGCCCAGTCCCCTCCCTGTGTCTGTCATGGGGTCGGGGGGCCACACGGCTACCCCCACCACATCCC
ACTCCTGGCCAGGGCACAGGTGGTGCCCACACTCCACTGGCTCCGCTTGGCTAGAGAGGCCACAGAAGCA
CCTGGCCCCCACCCCCACCTGGGGTTTCTGTCTCAGGCAGTCCCTGCCTGCCCGGGCAGCGCGGCTCAGT
CCGTGAGCAAAGCCACGGTGAGGTATCTTCTTCCCGGTGTGATCTCACATACGTCGGCGTGTCTGACGTG
GTAAACTTTTGTGGTCCTCTTCTCACAAGGAGCAACACACCTGTTCTGTTCACTTCTGTAACTGAGCACC
TAACTCACGGCTCCCCCGAGGTGCTTTGGGAAGAGCTGGTGGCCATGGAGCCTTTGCCTGGCTGGGGAG
GGCTGTGCTGGCCCTGGGCATCCCTGCTGAGGAGGCTGGGGGGCCACCAGTGACGTCTGACCTTCTGCA
GAGAATGGTGATCGTATGCAGCACTGGGAAGAGTCTGTGCGGTGCTGCTGTTTCGCGGTCGTCAGGACA
GTCTGCCGGCACAAGAAGGACACTTTGCTTGGCCCCGTCCTCAAGGTAGTGGTGGGCCCTGCGTCTGTGT
CCCTCAGCATCTGCATTGGAAATCTCGGCCTAAGGGCAGGGCGGGCTGCCTTTGTGGTTGGTGCCCCTCA
CTGGACCCTCACTGCAGCTCTGAGCAGACCTGGGCCCTTGGATCACGAATGTCTCACAGAGCACCTGGGG
GTGGTGGGCAGGGAAGAGAGCCCTCGGCCTTCTCAGGGCCCCACCTGACCCTGCTTCACACAGCTTCCCC
AGGGGAGGGCCTCTCTGGCTGGAGGAGGACACTGGGTGTTGGGACCTGAGGCCATGGCCAGGGTACAGTC
CTACTGCCCGTCCCCAAGCCATGGGTGGCCTGCATGTGGGGACCCTCAGCCCCAGAGGGGCCAGTGTG
CAGCAGGAGCTTCTGCCCCAGCTTCTCCCAGGCCTGAGGCTGGTGGGCACTTGGGGGTGGGGGCTGTGCA
AGGGGCTACGGCTCTTCCTCGAGGCCCAGCTCTGAGGGAAAGGCCCAGGTGTTCACAGGGGCCCTGGAGT
GGGCGGTGGAGGTGCATGGCCCTGATCCCAGGTGGCTCTGACCCGGGTCTCTCCGCAGCAAATGTACATC
ACGTATGTGAGGAACTGCAAGTTCACCTCGCCTGGTGCGGTCCCCTTCATCAGTTTCATGCAGTGGACCT
TGACCGAGCTGCTGGCCCTGGAGCCGGTGTGGCCTACCAGCACGCCTTCCTCTACATCCGCCAGCTCGC
CATACACCTGCGCAACGCCATGACCACTCGCAAGAAGGTGTGTGGTGGGGCCCTTCCAGGCTCATGCTGG
GCATGGGGTGGGGCAGCCCAGGTGCCCGACCCAAGGCAGGGCCTGGGGCCTCCCCGAAGCCCCTGTCTGG
AGACAGCCCAGCACCCTGGTGCAGTCGGTCCTTGCAGGTGGGGAAGGGTGGATGGGTTGAGACCCCGTG
TGCAAGATGAGGAAATGATTCCTGTGCCGGCCCAGGAGGAACGTGCATCAGCCTGACTTGTCAGCCTGGC
CAGTAGCTGACGTGGTTCTCTCTGACCAGGAAACATACCAGTCTGTGTACAACTGGCAGTATGTGCACTG
CCTCTTCCTGTGGTGCCGGGTCCTGAGCAGTGCGGCCCCAGCGAAGCCCTGCAGCCTTGGTCTACGCC
CTTGCCCAAGTCATCATTGGCTGTATCAAGTGAGTTGTGGGTGGGCAGGGTTGTGCGGGAGGGTCAGGA
GAAGCAAATTTGCTGGGACTGTGTGGGCGGTGCCTCTGGCGTTCAGGGCCTTGGGGCCTGAGTCTGTGTC
CTGGCCGTCCCTGAGGAAGGGCTGGGGTCCCTGTACCTGCTACGGGGAGATGCTCTGGATTCTGGAGAGC
TAGGGCTGGTGGGCACCTGTGACATGAGCTCCTCCAACAGCGGTTTAGCCGCCTCGGGTGCCACCCAGCG
```

FIG. 5 Cont'd

```
TGTGTTCTGGGGGCTTGTGTGCAGTTTGCAGTGAGTTTGGTTCATTACGTGGGGTTCTTGGGTGGAGCAC
ATCTGATGCAGTGAACTGCATTTTGGGTGTGAGCGCTTAGGAGGGTCCAGGCACGGTAGGGGCTGCAGCA
GGAAAAGGTGGGAGCAGTACTGTGGCCTCTTTGGCCAGGAGGGGGCATCTGTCTGGCTGAGCCTTAGAAA
CTCAAGGCTGGGAAGGGAGGTGGGAAGTCCAAGGGAAGAAGTAGGAAAGGCGGGAACAGGGGAGGAGAGCA
GGCAGGAACAGATGACCCCTGCCACCGTGTTGAAATAAAGCTGAAAGCTGGGTAAGGTACCTGCAGCCCC
ATAGCTGGGCAAGGGGTGCAGGTCCCTGCGGTTCAGACGTGCCTTGTCCTGCTTTAGGGGTCTGATGTCG
GTGAGTGGGGGAGGAGGTCCAAGACAGCAGGGGAGGGGCAGGGGCTGCCAGAGCCGGGGCCTCTGCTCA
CTCGGCCTTCCCACCCCCAGGCTCATCCCCACTGCCCGGTTCTACCCGCTGCGAATGCAGTGGATCCGTG
GGCTGACCGTGGTGGGCGGAGCTGGGGGCCTTCATCCCGGTGCTGCCTTTCATCCTGGAGGTGAGTGA
GGCTGTGGTGGGCGTGTGGCACCTCTGCCTGCTCCTGTAGGGAGCATCTGCTGCTCCGGGCGTCTGTGCT
GAGTTGTCCGGCGACTTCCCGGAGCCCTGGCCGCCTCCTTGTCACGGGTGTCACGAGGACAGTGCTCCTC
CGTGTGCTGGGGGCAGTGTTGGGGAACGTGGGACCACTGGGGATGAAGGCGGCTGCTGCTAGGGCTGTGC
TTGAGGATGCCGGGACCTGACCCTGTAGGTGCTTGCCCAAGACTGGAGTAGGCAGGAGGCGAGATGGGCC
AAAACCCAAGTCTGATTGCTGAACTGTACACTGAACAGTGCCCTGCCCTGACAGTTGTGTGCATGTGTAT
GCATTTGTATGGAGGATGTGTGTACATCTGGGTGGGTGCGTTTGTCTGTGCATGCATGCGTGTGTGTGCA
CCATCTGGGTGCATGGGTCTGTAAATCTGTGTGTGTGTGCATATCAGTTCATGTGTGCATCTGTATGTGT
GTATGCACGTGTATCCATGAATGCCTGTGTGCCTGCAGGTGTGTGCATCTGTGCGTGTGTACACCTGTGT
GTATGCATGTGTGTACCTTTGCGTGTACCTTTCGTGTGTGCACCTGTGCATGTGTCTTTGTATACCAGT
GTGTACCTGTGTGTACCTGTATGCATGCACATGCGTGTGTACCTGTGTGCACCTGTCTGCATGTGTGTAC
CTGTGCGTGTGTGCACCTGTGTGCATGCATTTGCGTCTGCATGTGTCTACCTGTGCATGCATGAACCTTT
GCATGTGTGCATCTGTGTGCATGCATGTGATGTGTGTCTGCGTGCATCTATGTACCTGTGTGCACCTATG
TGCATACACACGTGTCTGTGTGCACTTGTGTGCATGCATTTGCATCTGCATGTGTGTACTGTGCGTGTGT
ACCTGTGCGTGTACCTGTACACTTGGGTGCATGCATGCACGTCTGCTTGTGTGTGCCTGTGCGTGTGTGC
ACCTGTGTGCATGTACGTGCGTCTACGTGTGTGCCTGTGCATGTGTGCGCCTGTGTGTACCTGTGTGTAT
GCATCTTTGCACGTGCACATGCCACTCAGGTAGGGAAAGATTGGAGTCCGAAGTTTCAACTTTCAGTGGG
TGGGTTAGGCCCCACCCCGCTGTAAATTTAGGAATTCACGATCTCCACCCTGTTTATCTAATGAGTTCTC
AGCCTCATGAAGGCCCAGAGTCGTGTCACAGCTGTCCTTGGGGCTGGGTCCCAGGTTGCTGGGTCCAGAA
GGTATGGAAGCCCCAGGCACGTTCTGATTCCCCTTCCACTGAGGCAGGGATGCTGAACATCTTTAGGAAG
CCATGTTCACTCCCATGGCAGCCAGCAGTGGTCTCTGATTGCCCAGCCCTTGGCCTGGCCCCTGTGTCTG
TGGGCCTCCAGCTCTGCTGCCCAGCTCCAGGCATGCTTTGTGTCTGTTTCCCTTGTCCAATCTCCTTGGC
TACGTGCTTTCTTACTCTCTTGCAGTGTCTGTTTCTTCACTTGTGCACTGCCCTGGTTCACTGCAGCCGC
ACCCTGTAGGCCCCTCTCACGCAGGGATGCAGGCCTCTCCTCTCCGGAAAAAGCAAACCCTAAAAGCTAA
AACAAAGCCCTCAGCTGTAGGCCGTGCCTGCCCTTCCCCGGTGCCTGGACAGGAAGCCAGTCGCCTGCCC
ATACTTTTGGCCCAGGCTAGAGAAGGGCAGTGTCCTCCCAGAGGTTCATCAGTACCAGGGCGTTTTCCCA
TCTGGACCTGAGCTCAGCTGTCTGGCAGCCACCCCTGCTGAGTGGGGTGTCTTGCTGGGGCCTCCACCCT
TGGGCCCCCCATAATCTGCTTCTGTCCTCTGGTGCCCCAGCATGTACCCTGGATCTCTCTGGTTCACAGC
CTGAGGGCTCCTAGTGGTTGGGAGGGGTCACAAGACTGAGAGGCCAGGCTGACTCTTTCTCTGCTCCTC
CTGGCATGTCCTACGGAGGTGCATGGCCTGTGGCTTCTGTGGAGGGTGTGGGAGGGGCCCCCCAGGCCTC
CCGTGACCTCCCATCTGTCCCGTCCTGTGTCTGGCACTCTTTGCTGTTGCTGCTGCGTCTTCTGGTTGCTC
GGGACGGAGCCCCATGTGGCATTGCTGTGCTGAGGGCCAGGATGGGCCTCAGTGCCATGTTGTCAGGAAT
GGGGGCTGTCCTGGTACTCTGTGTGGCAGGGACCTCTAGGTCTCCAGACGTGGGTCCTTAGTGCTTCCCA
GGATTTTGGGAGAGGGCCCGTGTTCCTGATCCTTCCCTGCTGATCAGAGCCCCACTCGGGGACACGCCAG
GCTGTGTGGGGCCATGGGGCTGGGACCGTGCCTAGCTGCTTATCTCTTGTTTCGGGTTGGGTCTCCTCGT
GCTGAAGCCTGAGGACCAGGGTGACCAGGGTGCAGCCAGGTGCAGGGCCAAAGGGACCAGGGGGACCAGG
GTGCAGCCAGGGTGAAGCCAGGGTGACCAGGCATGGGGCCGAGAGAGCCTGACACTGGCCCTTGGGGCAG
ATGTTCCAGCAGGTCGACTTCAACAGGAAGCCAGGGCGATGAGCTCCAAGGCCATGAGTTCTCGGTGA
TCCTGAAGCTGTCCAATGTCAACCTGCAGGAGAAGGCGTACCGGGTGAGGCTGGCTCCTGGGGAGGGCCT
GGGCAGTTCCCAGGGTGGGGTTGGGGGTGCTGAGGTGGATGGGAGGGGGCTGGCATCCTCCAAGTTCAAG
CATGGACCTTCATGGTCTCCCAGGGCTGGGGCATGGAGCCCCTTCCTTGCAGTCCGTGCCCTGGAGATGG
CGCTGCCCTGACAGCCTGAGGGGAAGGGGCCTGAGTGCAGCCCAGCCTCTCCCTGATGCACTCGGCCCT
CTCTCCTGCTCTTCAGGACGGCCTGGTGGAGCAGCTGTACGACCTCACCCTGGAGTAGCCTGCACAGCCAG
GCACAGTGCATGGGTCCGGACCTGGTGCTGCCTGTGGTCTGCAGGTGTGTGTCCTGCCCACACCGG
CTCGTGGCCGACTCAGACTGTCTTATAACGGGCTTGGCTGCCCCAGGCTGGTAGGAGGTGCCCTTGTCCC
GGGTACCTGGGACTGGGGTGGAACCTGACTGCTGGCAACGCGCCCCGTGAGGCCCCCTTGGAGGGGCTGA
TGAGGGGTTCTAAGCCATTCAGGAGGTTTGGGGGCAGGCCTGGGCAGTGGGCTGAGGACCCTGGGAGCAC
AACAGCCTCCTCCCCAGGTGGGAACCACAAGGCTGATCTTTGCTTCGGGGTTGGGACTGAGCATGCCGAC
CCTGGCTCAGGCTGGTACGCTGATCGCACACTTCCCCAGGCCATCCCGGGTGTGGGGAGTGGGTGGAGTG
GCTTCTCAGGTGGCAGGAAGGCCTGGCCTGCCCCGCCAAATACCCCACATCAGCCTCATAGGAAGGCCCA
```

FIG. 5 Cont'd

```
GCCTGCCCCGCTAAATACCCCACGTCAGCCTCATCTTAGGCAGGAGTGGGGTGGAGGAGGGGGTTCTCCT
TATCCTCAGAAGGTCCTTCTGGGCCCCCACGGGAGGTCTGTTTGCTCTCAGCCGTGATGTTTCCAGCCTC
AGGGAGCGCTGTGCTAGTGGAAGGGGTGGGGGCCTGCTGTCTGGCCCTGGTGCTGGAATCAGATGTGCCG
ACTATAGGTCTGTGCAGTGTGGGGAGGAGGGATCTGCTCACATGAGCCACAATTGGTCAGAGGCTTATCC
AGATAGAGGTGTGTGCATGTGTGTGTACTCACACACGGCCACACATGTCACATGCACAGAGCCGGGACCC
CCTTTCTGGGGCACTCACAGCATGGGCCACAGCCTCTGTTCCTGCCCATGTCCTACTTGGGTGGTGATAC
CTGGCATTGGGGCATCTCTGCTTCTGGGACTCAAGGGCCCAGGGTCGGGTTCTGGGGTAGGGGTCAGAAAA
TGTTTTTGGTGAGGGGCCAAATGGTAAACGTGGCTTTCTACGGATGTTCAGCTGCACAGGCAACTGCAGA
ACCATGCAATGCACACGTGTGGCTGCACGTCAGCGAGACTGTATTTTATTAGTAGTAGTAGTATTGTTTG
AGATGGAGTCTCGCTGTGTTGCCCAGGCTGGAGTGCAATGGTGCGATCTCGGCTCACTGCAATCTCCATC
TCCTGGGCTCAAGCGATTCTCCAGCCTCAGCCTCCCAAGGAGCTGGGTTTACAGGCGCCCACCACCACAC
CCAGCTAATTTTTGGTATTTTAGTAGAGACGGGGTTTTGCCACGTTGGCCAGGCTGGTCTTGAACTCCTGA
CCTCAGGTGATCCACCCGCCTCAGCCTCCCAAAGTGCTGGGATTACAGGCGAGAGCCACCACGCCTGGCA
TAAAACTTTATTTCCAGAGGTGAGTAGTGGGCAGGGTTGGCCCAGAGGGTGGGCTGATTCTGCCTCTGCC
ATCCCAGCTGCAACAGCTATGCACTTGAGCCCTGAGATGGGATCCATGTCCCCTCCTGGGGTATCCCCGT
GGCCACCACGCGTGGTTTTGCACAGGACCTGGGCCAGCTGTGCACATGGAGCGGTCCTGGGCTTCAGTGG
CTGACCCCTCCCTTCCGCAGCTGAAGTCGTTCCTCCGGCAGTGCAAGGTGGCGAATACTGGCGGCAGGT
GCAGCAGCTGCTTGGGAAGGTTCAGGAGAACTCGGCATACACTGCAGGCGCCGCCAGAGGGTTTCCTTC
GGCGTCTCTGAGCAGCAGGCAGTGGTTAGTGGGCCCTGGGGTAGTGCCACCTGAGGGCACCTGCCAGGG
TATAGCCCCAGCTACATGTGGGGTTTGCCCAGGGTGAGGCATGACCCTGAACTCCCCAACCCCCAGG
AAGCCTGGGAGAAGCTGACCCCGGAAGAGGGGACAGGCCTGACCTTGTACTATAGAGCACTGGCCAAGGT
GCGTGACCGGGAGATCCAGCTGGAGATCAGTGGCAAAGAGCGGGTGCGGCTCGGCGAGGGGACCTGGGGG
TGTGTTGTGACTTCCTGGGTTTCAGATCTAGCGCACTATGACTTGAGACCAGGGCGAGGGTTTGGAAACA
GTGCCAGGCGGCCAGGGCCGTGCCCGGATGATTCGACTTGGAGAGGGGGTAGGTGTTGGAGAACTGGCCA
GAACCAGGCGTTTCCAGGGAGGGGAAGCCCCAGGCTGCACTAGGTTGGGGAGGCCATGCCCCCTCAGGCC
TGATGGGCTGGAGGCTCCGGGCAGGTGGAGTGGCTGGACTGACCTCGTCACCCAGGCCAGTATGTGGGCA
CCAGGGGCCCGTGAGGAGAAGCAGGAAGGGCTCTGCCTTTGACCTTGGACATGGGATGGACAACTTGGAG
GATGGCTTTGTGATTTGGGAACAGAGGGGACTAGAAATTGGCCACATGGGCCCTGGTGGTGGGTCTGGC
GATGCCTGGCCCTGCTGTGGCCGCCAGCCCCTGCCCTCTCTCACCTGAGCCCCTGGTTCTTTGGCCTTCC
AGCTGGAAGACGTGAACTTCGCTGAGATCAAACGAAGGAAGATGGCTGACAGGAAGGATGAGGACAGCAA
GCAATTTAAAGACCTCTTTGACCTGAACAGCTCTGAAGAGGACGAGCCGAGCGATTCTCGGAGAGAGGT
GGGGCCTGCGTGGTGCTCCCAGGGGAAGGGTGGGCCTGGAGGGCTCTGCTGGACTTCCCAGAGCCACGAG
GGCCACCTGTACCCATCCTGCAGGGGGCTCACCAGTCTCTGGCCCAGCTGGGGCCAACCTCAGTGTTGCC
AGGCTTCTGGTGCCAGCGCCTTCCCTCCTTGAAGTGAAGGCCTACTGGGATTGGTAACTCTGTCCCCAGG
CCTGTGACCTCCCAGTTCCTCCCCAGGGCTCCTCTCCACCTGCTGGAAGTCAGCGGAGGGAAGGGTGTTG
GGAGCCTGGCCACCCTCCTGCCCCACTGTGACTTTGCTGGTGGACCCTGTGGGTGGGAGTCATATGGAC
TCTGCTTCTTGTTCCTCAGGGATACTGAGGCCCTGACCATCCGGATGGCTGAAGACGATGAAGAGG
ACGAGGAGGACGGCGAGGAGGACAGCAGCAACTCGCAGGGTGAATGGTCTTGGGGTGAGAGGGTGTGGCC
CTGTGAGCCCATCTGGCGGGAGGGCAGAGCCACGTGGGCGGGGGCGTGGGGCTCTGGGCCAGGCTTTTC
CCTCCCTGGGAAGGCCAGGCCAAATGCTCTGTTCTCTGGCAGCCAGCAACAGGGATAAATTAATTAGTGC
CGTGATTAATTAGTGATGAGTAACCTCTAAGGCTGGCTTCTTCCTGATAAAGCAAAATTTATGTAGCCTC
CATCTCTCCCCGCAGATGGAGACCCAGACGCAGAGGCGGGCTGGCCCTGGGAGCTGCAGCAGCTGGC
CCAGGGGCCGGAGGACGAGCTGGAGGATCTGCAGGTCTCAGAGGACGACTGAGGCAGCCCATCTGGGGGG
CCTGTAGGGGCTGCCGGGCTGGTGGCCAGTGTTTCCACCTCCCTGGCAGTCAGGCCTAGAGGCTGGCGTC
TGTGCAGTTGGGGGAGGCAGTAGACACGGGACAGGCTTTATTATTTATTTTTCAGCATGAAAGACCAAAC
GTATCGAGAGCTGGGCTGGGCTGGGCTGGTGTGGCTGCTGAAGCCCCACAACTGTGGGCTGCTGAAGTCA
ACTCCGCGGGGGAAACTTACCCTTGACGTCAGCAGACCGAGACCAGTTCCCAGTTCCAGGGGAAGGCTTC
AAGGCCCCTGGCCCTTCCACCCACCTTTGCCCTCAGTATGCAGACCTCGTCCATTTGCACCAGGTTCTGC
CTTCACTCCACCAAGTCTTTGAAATTTGTTTCCTTTCCTTTGAAGTCACATTTTCTTTTAAAATTTTTTG
TTTTGCATCCGAAACCGAAAGAAATAAAGCGGGGGAGGCAGGGCCATTGTGTTG
```

Figure 6

5'
AACATGCAGGATGCCGCCACCCACTTGTTGGTCCTCGGGTTGTACTTCTCTATGGAGTTGAGGCTGGAGCTGCC
GTCATTGCCCCCACGGCGTAGAGCCAGCCGTCCATGGCCACCAGGTCATGTGTGCTCCTGGGGAGTTGGATAG
GCAAGAGTAAGCCCAAGGGGCAAGCCAAGAGACAGGCCAAATGAGTGGGGCACAGAGGGAGTAACCATAGGGAC
AGGGCAACGAAAGGAGCCCCCTATGCCCGGGGGGAACCCAAGGACCTGCCGTACTGTTGAGGTGCTGTGTGCAC
AACCCCTGGGGCTACACTCCTGGAATAAACCAGATGTAGTGGCAGAACCACTCACCACCCGCCCCTGGCCTTAT
ACACCTGCGGATATTCATGGGTGCCACACTCTCCCAGGCACCAGCCTTGGTGCTATATCTCTCCACTGAGTTGA
GGCAGCTTGTGCCATCATTGCCCCCTGCGACATACAGGGCACCCTCCAGCACTGCTACTCCTGCTGAGCTGCGC
CGGCTCAGCATGGAAGCTACAGGTGTCCATGAATTCACCTGTAGAGACAATAGGACAGGCTGGAGGCAGACCCA
CCAAGGGCCCCCCAACCCTGCCACCACATAGACTCTACTCTTGGTTGGGTATCTGAGGGTCAGGGGTGGGATAT
AGAAAGCAGACCCCTTGGGTGGCACAGATGGCCAGAATCTGGGATTATGCCCCATCCCCCCCAGCACTTTAGAG
GAGGACATTGTGATGGGGTGCGCTATGCACCTGGGGCTCATACTTCTCCACGGTGGCCAGGTGTGACGAGCTGT
CATAACCACCCACGGCGTACAGGTTCCCATCTGTGGGAAGGCAATATACCCACGAAGCTCCTGCAGGGTGTAGG
AGTTTTGGGGGTGGGTGGGAAGGGGAGAGGCAGGAAAGCGGGTACCACGGGAAGCCTGTCACCCACCAAGTGTG
GCCACACGCACATATCGCCTCCGGGTGCTCATGGCAGCAATGGATGTCCATGTTCCCGTCAGTGGGTCATATCG
TTCAGCACTGTGGACACCAGAATGATGCCGACGTTCAGTTACAACAGTTAAGTCATCCTTGCCCAGGCTCTGTC
CCCTCACTCCCCCCAAAGCTACGGCTGAAATCCCGGGCATCACAGACTCTATGAATAGAGAGCAAGGTGTGCTG
GGCGGATACTGGCTGCTGGCTGCTTGGACTGGAGGGAGGGCCCCTCCAGGAGGAGAATGGTGCCAAGGCCCTGC
GGATGCTGTGCCCTGAGGTAAGGAAGCCTTGAGGACCCAGTAGCCTGGATTAGGCCCTCATTCTCTTAGCCAGA
TGTGACTTCATAGTTAAGCCAGCCTTAGCTGCTGCTGCTGAGCCGACCCTGCAAAGCCACTGGGGCCCTAACCC
AAACTACTACCTGTTGAGGCAGGAAGCCCCATCGTAGCCACCAGCTGCATACAGGAGCCCATGCAGAGCAGCTA
CACCTAGGCAGCTCCGCCTTGTGCCCATGGAGACCTCGGGCTGCCATGTGTTTGTCACAGGGTCATAGGACTCC
ACCGTAGCCAGGTCTGAGGTTCCATCGTAGCTAGGAGAAGAGTCCGCTACTGACCAAGGATGGCCCGGCAGGCT
TGTGACAAACCTTTCAGCCTACATGGCCAGCTTCTATGCTTACCCGCCCACAGCACATACAGTCGGTTCCCGACGG
CAGCAACTCCTACACGAGCCCGACGTGTAGACATGGAGGCCACCACATGCCAACGGTCAGTCCGCGTGTCATAC
GCTTCACAGTCTCCGTGGATCGCGAACAGGCTCCCACCACCTAGAGATGGGTAACTATAAATAAAGGGGCTCAA
GGCTGGGCAGAGGACTCTAGTGTGACCCAAGTACAAAGACATGAAGGCTCCAGGGGTGGGAAGAGATAGAGACT
GGGACACACTAGTGGGCCCCATCCTATAGGGTCTCTGAGACACACAGGTCTAAGTATAATGGGTTGGGTTTATA
GTCTGAGTTGGGGTGGATGGCCTAGGGCAAAATGGGAAGGAGAAGGGGTTTAGCATACCGACAGCAAAGAGCAC
AGGGCCAGCGCCCTCACATCGACGGGGTCTCGTGCGGCTGGTTCCCAGAACACCTCTCTGCTCAGGCAGCAGGT
GGAACTTAAGGGCCTCGATGAGCAGATCCTTGCAGTCAGGGTGATGCCTCACAAGGCTTTCGGCATCCACGTGG
CCCAGGAGGAAGTCTCGGCTCAGCAGAGGCAGCCGTACACACTTCATCAACTAGGGCAGGAAGCGCCATGTAAG
GCAAAACCCTGGGCGTACTTGGCCCAGGGCTAAGACCCACTCAGGTGCCTATAGCACCTGTGAGATTGGGTCTT
GAGACAGGTGGCTCAACCACTCCAAAGGAGTCCCTGGATGGAAGATGCTAAGGACTTGAAGAAGTAAGCTTATA
CCGCAGCCACCTGCATTCCCTTCTGACAGCACGGGAGCTCCAGGACCTGGCCTCACCCTTGGTACATGCTGCCT
CCGAGTGTCTACGTCATGTTTGACCCAGCTCAGGACTGCACGGTACACATCTTCCTCTGAGGGCACGTTCAGGC
TATCACTAGAGACCAATTCCAGCACCTGGGGCGAGAGGTCCTCAGACCTGACATCTGGGTAGGGGAGGGCCCA
GAGAACCCTGAACGTGTCTGAGAGTATCAGACAGAGGGCATGTGCGTGTCCATGCACAAACACGCACACTTAAC
GTTCTTAGAGTGAAGAACCAAGCAGAGTCAAGATTCACAGATTTTGTTCCCAGTAGAGGGGTGAGGGGTGTCCA
AGGTCCTAAGTAGTCTCGGGTACATAGAATCAGAGACTGGGAAATCATGGCCCTAGAATGCGGTAAAGACAGGC
ATCTAAGACAAATGATTGGGTGACATGAGAAGATGGAAACAGGGTTGGGAGGAGATGGCCAGGGAATGAATCAT
AGGGTGAAACTCGCACCAGAAACTTGAAATGAGGATTGCAGAACACTGGCTGCAAGGGTCTGGGCTTGGGCAAT
ACATGGTGGGGCTGGGCCCAAACTGGCATGTTACCTGCTTCAGTGGTTACCTGCTTCAGTGGCAACAGCATGA
ACTCCTCAGTCTTGGCCACATCCACGAAGTGCTGCAGCACGTACCTGTGTGCTGCCTTGAGCAGGTCACTGCAT
GAGTGTGTGTCTGCAAATCCTCGAATGCCCAGGCAGTTGGAAGGGTCCAGCTGGCTCAGGAGGAACTTGCAGCA
GGCATCTCGAACACCATTCAACTGTAGAAGGCTGGCAGCTGGGAGCAGAGTCTGGGGCATGAAGATGGGTGAGG
CAGGAGGGTTCCAGAAGAGCACAGAGTGACTGGATATTGGGGAGAGGCATGGGGGGGGGCAGGGCACACAGAT
CTGGGCTGGAGATCTCAGGGGACGTGGGTATGGGAATGGTAGGCCTCACCTGAACGTTGCCCTCGCCCACCACG
ATCTCAGCTGTGTATGCAAACTGCACCAGCTGGTCTAAGGCTTGCGGGTCAATGTCATGCAGTGTCACATGTGT
CTGGCGGCTCTCACTCATCTCATCTGTGAAAACAGTGGATTAGGCGGCCTACCCGGGAGATCTCGGAGATTC
CCCCTAGGGCTGCCCAGACTGTTGTATGTGGTACTTGCTTGTGAACATGGCGTGGAAGTAGGGGCTACAGGAGG
CCAACACCACCTTATGAGCCCGGATCTCCTTGGCAGCCACATGCAGGACGATGTCGCACAGGAGGCCACGCTGC
CGCATGCGGCTCATAGCCACAAAGCATCATGGTAGTGCCGCTTTGAGTTGTGTGCCACACTGTGACCCTCTCT
GCTCAACAGCTGCATCGCACCTTCCATCGGGGCTGCAGGCCGGGCCTGCCGGGGCCGAGCTCGCTCTGCCTCGG
GGCTGCAGGCCGCAGGACTAGGTCAGGGTTTGTACCCTGTAGAGGGCCACTCA

FIG. 6 Cont'd

```
CCCGCCTTTGAGAACTCCCAGCACAGCCAAGGCAGCTGCGGTCTATGCCCAGGAGTTCGTTCAGTCATCAGGCA
CCAAAGCCCATGGAGGACCAGCCTGTCACTCACTGCCACTTTCCAGGGCTCTAGATCTCTCTCCGGTCCAGGAA
CCTCGCTGGAGCCGGAGCAGATTCTTTCATAAATGTAAGCCTGCTCTACCTGTCCCCCTTCCTCTGCTGACTAC
CTCTCCTGGGGCTCCGAGCCCCTCATCTAGTGCCCAGGCCACTCATGGGGAGGAAGTTGGCAAACGTTGTCCTC
TGAATCCCCAGATCCCAGTCANNNNNNNNNNNNNNNNNNNNCCCGCCCTCCCGCCCGCCCTCCCACTCACGCCG
GCGGCTGGGGCGGCGGTGGCGCCTCAGGCCCGGGCCCCGGGCTGCTGTGCTCGGGACTCTGCGTCCTGCCCGCC
GGCCGCTCGCCACGGGGCTGCATAACTCCAGCCGCCAAAGCCGCGACCCTGATGGACGGATTGGGACGCGGGTG
CCCGCCCGGCCGCTCGCTCCACTCGGGCGCTCGCCCGTCGCCGCAGACCCTGTTTCTCGGCGCCGCCCGCCCTG
CCGCACGCAAGGTTGCAGGAGCCGCTGCCACCCGCGTCCCCGCTCTCCTCCCAGGAGCGGCCTTCCTTCGTGTGG
CGCCTAGGTTAGCTTCACATCCCAGCGCCCCGGTTCTCACCTGCTAGAGCTTGCTGTGACTGACAAAGCTCCAT
AGCACGGGGGTAGAGCGGGACACTTGCAAGTGTGTGTCCCCCCCCTTACCCTCAGGCCTCCTGTGCACAAGCGC
GTGCAAAGGTTCAGCGCCCCTATACATGCATATTTGAGCATGAGGCGGACGGGGGCTGCTAGCGTCTGAGAGGT
GCAATTATCTATTGACATGGACGCAGCATTCTTGTCACACCCAGGCTCGCCAAGGAATTGGGTGTCCTTTGACT
TAAAAAAAAAAATATATATATATATATGTTTATATATATATATTATATATATATATATACCCGTACACATAATATATATA
TATATATATATACATACACACATATATATATATATATATTTTTTTTATGTGTACGGGTGTTTTGCCTACTTGTG
TACTATATAAATTACGTGTGTGCAGTGCCTACGGAAACCAGAAGAGAGCATCAGACCTCCTGGGACAACATTGG
TGATCCACTTCGTAGACCCTGGGAATTGACCCCAGTCCTCTGGAAGAGCAGCTTAGTGCTTTTAAGTCCCGGC
CATCTCTATGCAGCCCTTGCTTGCTCGGTCGGTCGGTCTGCTGCCTGCCTACAATTTATCATCTATCAATCCAT
CCATCTATCCCTTTATCTGCTTTTTTCCTGGAATTTGCTCTGTATGGACTGATCTCAGAGACAGCACAGAGCGA
GCTCGCTTGTCTCTGAGCGCGGAGATAAAAGGCGTGCGGTCGGGACAGCCCTTTACTTTTTAAAAAAAAAAAAG
ATATTTTTCCCCCTCCACCCTCCGGGCGTGGTAGGCAGGCTGTTCAGATTTCCAGCCTTGTTTCCCGGGTGCGA
GCGGTCGTTCCAGGCGGGGCTTTGAGCTGTGAGAGCCTGAGCCGAGCTCGCCGCCCTCCCGCCCGGGGACCGCG
GCCGCGGCGGCTCGAGAACCCGAAAGCCAGCAGCAGGGGTGGCATGGGCGGGGCTCGCGGGAGGAAGTCGGAGG
GCGCAAGGCATTCGTGGGCCCGGAAGTCGGCGCACGCGGCTGGGCGCGCCATGGCTGCCGTCTCGCGCTCGCGG
CAGGTGAGTGGCCTGGGCGGGCGCGCGGACCCCGGCGGGCGCCTGGTCGCGGGGTCCGTTCCGATCCTGACGCG
GTGTCACTGGCAGGCGCCTGGAGGACGTCAGTCGTGGACGAGTTCCTGGCTTCCGGCTTCGAGTCCGGATCCGAG
TCGGAGCTGGAGGGCGCGGCGGAGGCGGCGGGGAGGAGGGCAGGGCGCCAGGGAGCGGCCTGGAACCGGGAGCG
GCGGGCCGCGCGCACCTGCCCGGGCCCCGCAGGAGGGTACGCGCGGCTCCAGAAAGTCTTTTTGCAAAACGGGC
AGCTCGTCGTGGGCTGGAACACGCGGGCTTGAGCTTAAGGAACACACGACGGGGGCCTCGGGGTCCGAGCGATGGGA
AGGGTTGCAAGGTTGGAAATGGAGGAGAGCTTGGAGGGGGAAGCGCACGCGTGGTTGGGAGGGGGAAGCGCACG
CGTGGTTGGGAGCGGGAAGCGCANNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNAGGGGGAAGCGCACGCGT
GGTTGGGAGGGGGAAGCGCACGCGTGGCTTGGAGGGGGAAGTGCACGCGTGGTTGGGAGGGGGAAGCGCACGCG
TGGTTGGGAGGGGGAAGTCCACGCGTGGTTGGGAGGGGGAAGCGCACGCGTGGTTGGGAGGGGGAAGCGCACGC
GTGGCTTGGAGGGGGAAGTCCACGCGTGGTTGGGAGGGGGAAGCGCACGCGTGGCTTGGAGGGGGAAGTGCACG
CGTGGTTTGGAGGTGCTGTTGGAGGAGAGCTGAGGACGGTCTGTTTTACAGCAATGAGGCGAGCATGGTGGGTG
GGGTCACAGCTGCTCTGGGCCGGGAGGGCGCTCAGCGGGTGCTGAGTTTGAGATGGTTGTGTTGGAACAATGT
CAGAGGTGCTGTGCGTGTGACGATGGAGGAGAGGCAAGCCCGATGGTCATCGATCCCACAGTGAAGGGAATAAA
CTAACATGGCCTCACGGAGGCGACAACCAGATTGGCTGTGTAGGGTCGAAAAACTCCGTCCCCCGACCCGACAC
CCGTTTTCTCAGCCCGCGTAAGGGCCGCGCTCTGAGCACAAGAGCGCTCTTGGCGTGAAGCAGCAGAGACC
CCGAGTTCTACAAGTTCCTGCAGGAGAATGACGGGAGCCTACTGGACTTCAGTGACTCGACAGCTCTGCCGAA
GAAGAAGAGCCATTCCACTCCCTGCCAGACACGCTGGAGGTGAAACCCGGCAGACCTGGGCGTGGGGGCACCTG
TGGTTTCTATACACCGTCCCAGCCTTGTCCTTCTGTATCTGGTCCAGGAAGCTAGCGAAACAGGGAAGACGGA
GGAGGGACAGTGACGCGTTGCCCAGAGGCTGAGCAAGAACAATGAGCCTGTACCGTGACCCTGGCCAT
GGTGGAAAGGTGGAGGCAGGGCTCCAGGGTAAGAAGCAGTATAAGCTGGGTGGCTGCATCTCCACAGGCGGGAG
ACTCTGGCCTCGCCTCGTTTGAGGCGTCTGAGACAGCAGGTGAAAGACTGTGTTTCTGGGAAGCGCACAATGG
AGGCTCTTTCCAAGTGCCAGGGTCCTCCAGCTACGTCTCCTTATTTGTAGTGCATAGTCCTGCCTGCTTCCTCAC
ACTCTCTATCAGGGTTCTGACCCTTGTGGGGTGGTTGTAGAGTTTGTTTCATTTCTGTTAACAGGATACCACAG
ACGGGGCAATTTGTTTTTTGTTGTTGACTTACTCACCTGCATATAGGTTGGTGTACCG
```

FIG. 6 Cont'd

```
TATGCAAGTTCATAGTTAACCGATGGTTGTGAGCCACTGTGTGGGTGCTGGGAGTCAAACCTGGATCGTCTGGA
AGAACAGTCAGTACTCTTAACTACCAAGCCATCTTTCCAGCTCCAGACTAGTTAATTTGGAAAGAAATTTAACT
GGCTCACATTGCTGGAGGTAGGCAGGTCAAAAAGTACGGTGATGTCTTTGTTAAAGGCCTTGTGTTGTGATCCT
TGTTCAGTTACATCTTTTGAATTGTTAGAAATCAAGCCCAGGACTTGTACATTGTAGGTAATCACACTGTCCTG
AGCCCTGAGCCTTTTCGTTTGGCTTAGTTTGGTTTGGTTTTTGAGACAGGGTTTCTCTGTGCAGCCCTGGCTGT
CCTCGAACTCACTCTGTAGACCAGGCTGGCCTCGAACTCAGAAATCTGCCTGCCTCTGCCTTCCAAGTGCTGGG
ATTAAAGGCATGTGCCACCACTGCCCGGATGTTTCATGTGATCTTCATTACTTTCCAAAGGCTTTATTTCCAAA
TACCACCAAATAAACTTGGATATTAAATTTCTACTACATAAGCCTTTGGGCTATAGTCAGGCTTAGCATTATTT
CTTCACTGGGGACTTGGGAAATGAAGTCAGTGTCCTTTGAATAATTTCACACTTAACTTAGAGGTTTTGGGATTT
TTTTTTTTTTTTTTTTTACAGTTGGAGATCACTATGTAAATCACCCTGGTGGCTAACTTTGAACTCTATGTAGAG
TAGTTTGGCCTCAAAACTTGCTGTAGTCTCCTTGCCTTTGCTTTCCCAGTGCTGGCGTAGCCATCAGCTATCAT
GCTTGGCTTTCACTTTGGTTTCTTTAGGGAAGGGAGTGAAAAGGGAGATTCCCATACACTTTCTGGAGCAAGTT
TGTAATGCAGTATTCTCTCCCCTTTCTTCTGGGACTCTTGACACAGGCTCTGCCTGTCCAGGTGTGCGCAATAC
CTATTTTGTTGTTGGCTCATGGTCCAGTGATCTTAGCCCCACAGTTGCTCTGGCCCTGAGATTGTGGGTTAGAT
TAGCACCTTTTCAACTTGGAGCAGCTTCCTAGAGCCAGGTACTGTGAACTACTCTTTTAGTGATCTTGATCTCT
TGCCCCTTCAGCACCACCTTAGTCCCAGGCTGTTCGATGAAGTTGTACAGGCGTTCCGAGCAGGTGTAGGGACC
ACCCAAGGAGAGCAGGAAGCTGCTGAGACTGCAGGTTCCAGGTTGCAGATAGTGCTGGTGAGCTGGGACTGG
GGACCTGTGCCAGGCTTCAGTGTGACACCTGTGTGCCCTATATAGGTGAATGACACTTTGGTTCCTTGCAGTGT
TCAATGCTCTGGTTAGCTTTCTGCATTGACAAGGCTGTGTCCTTTCAGAGAAGGTGTCTTTGCAAAACATCCA
AAGGATAGCAATAGGTAAGGTATGGTCAGGGGTTTTGTCATTAAGGTAGAGGAGGTCACAAAGTCTTAAGGAAG
CACAGAAAGCAGCTAATAAATACAGATGAGTCATGTGGGGCTGGGAGTAGACATAGCCATGTGTCTTGAGATA
GCAGATGCAGAAGAGCAACCCTAACCCTAACCTGAAGGAGAAGATGGTGGCAGTTGGTTGATGCACTGACAGGA
TGAGTACATCTAGAGGCAGCAGAGAGTGAGGAGAGCAAGAAAACCCAACAGGTGGAGAGGGCAGAAAATAAGCC
AGGTGATATGACAGAAGCCTAAGTGAATGGCTAACACACCCAGAATCTGGGGAGCAGTTGTCATGAAGGGACAA
GTGAGATTTTAGAAACAGGGTTGCCCTCTGAATTGCATACAATGCTTGAGGTGTCACACAGATGAGATAGTGTT
GGTCTAGGTATCTGGAAGGTTAGACAGTGGGGTGCCTTAAATGGGCTTTGGTTTTTGTTCTTGGTACAGTTCAA
TAGATCTTGGTAAACACCTACTATGTTGCCAGGTGTTCATGGTTATACGGCTTGTGCTCGTGCAGGCTTGTGTC
TGAATTTCGGAATGGGCTGGGTGTATTCCCTGCAGGCTGCTGCCATGCAGTAGCCCACGTGGGGGAAGCTGCG
TGTGGATGTCAAGAGATACCTAAGCAGCGGGTGTGCAGGTACAGAATCCCAGGAGACCTGGTCATGTCTGATAGT
CTGGTGCTCTCTTACACCCAGATTCCAGTGACTTTCTCTTCTTCTTTAGCTGGTAGCCTGTTTAGGGAAGCC
ACGGTGCTGCAGCTGTGCTGGAGGATATGACAGCTTGGATGCCTTCCTACCTGACATTCCGTAAGCAGTGCCG
AATGTTGCTCAAGGTACGTTAGCTTGTCCTTGTCCTACTCCTGGCTAGAATAGAGGCAGCATTTGTGCCTATAC
TTGCTCTGCTCCTACTGTGTCCTCTACTCAGCAAGGGTCCCCAGTCTCAGATGGTCCCCGTCCTTTCAGGACA
GCGTGGCTTAGTAATGTGAGACTAGGCTCCACTGAGGCATGCGTGCTAGCCATGGAGGGTTCTAGGCCAGGAAA
GGCAGCGATGTATCTTTTTTCAGAGGATGGTGGTTCTGTCGAGCAGGGGTGAAGAATCTCTGCGGCTCCTGGCC
TTGGTGGTAGTCATCAACGCTGCCCGGCACAAGAAGGAAGCCTTCCTTGGTCCGATTGTGAAGGTAGCGTGAGT
CTTCTATTTGTTCATTAAGGTCTGTGTTGGGAATTGTGGTTGATGGTCCTTACGAGGACTTGACACCCAAACTCT
GATCATAGTTTTCTTACCAAGAAAATTGGGTGATGGTGGGAACAGGAACCCATGGTCTTGTGGGTATTGGTGGT
GATGGTGGGAGGGGCTCTTTTCCTCTGGGTACGAGAACGTTATACCCTAGAAAATAGGAACGTGTCTGAGGCCAC
CACCAAGATCAGATCCTGCTGTGTAGCTCCAGGCCTGGAGTGGCATCACCTGGACTCCTGCTGTACAGACCTAG
CTCGAAGTAGAGCGTCTCTACTTCCTTCCTCGGCCTTCGGTCCAGTCCCTGCCTAGTCCTCATCTTACCCTTCT
CTTGTACACCTTCCTCTCTTCTGCATATCTTAGATTATTTGTGGTGGGTACAAGTGTGTAGGCTGAGAAACATC
AGAGTTCTTGAGTGCTGGAACCATTCAGGAATTGAGTCTGCAGCTCTTTCAGACGGCAGTTCTAATGGAAAAC
CCTAGGTGTGGGCAGGTGGCTTGGAACTGAACAGTCGTTGCTCAGGTGGCTCTTAATTTTGGTTTGTCAGCAAA
TGTACATCATGTATGTGAGAAACTGCAAGTTCACCTCCCCCAGTAGCCTGCCCCTCATAAGCTTCATGCAACGG
ACACTGACTGAAATGCTTGCCTTGGACCCCAGCGTGTCCTATCAGCACGCCTTCCTCTACATCCGAGAGCTTGC
CGTCCACCTGCGGAATGCTATGACCGCAGGCAAGAAGGTAGGAGGGAGGCTGCTCAGCGCTGCGAGGGAGGCTTTGGGTG
ACCCGGGCCTTAGGGTTGCTAGAAGCCACTCTTTAATGGGGAGGGAGGCTGCTCAGCGCTGCGAGGGAGGCTTTGGGTG
GTTCTGGCAGGGAAGAACGGGCCTAGGATGTGGACTCACTCTCCCCAGGAGACACACCAGTCTGTGTACAAGTG
GCAGTAGTGCACTGCCTCTACCTGTGGTGTCGAGTCCTGAGTAGGGTTGGTTCCAGTGAGATCCTGGAGCCGC
TACTCTACCCTCTGTCACAGATCATCATGGCTGTATCAAGTGAGTTCAGGGACAGGGCTATGTTAGATTAGCC
TAGGGGTTGGGGCAGCAAGTTCCTCTTGGTATAGGGCAGAAGTTCCTGATTTGCTAGCTTCTGTGAATTACAT
TATACAAAGAATTTTCTCGGGTGGCCACACCCTAAATCTTAGCTTTTGTGGCTATAGTCTCTGAGGAAGGGCCT
GAGAAGATGAACTGGATGTGGATTTCAGGCAGCTGGGCTTCGCAGTCAGCCTCAGCTTAGGTAAATAGGTTAGG
TGTCCACAGTGTAGCACCTATATGGACCCGGCTCGGGCCCTTGTGCTATTGGAGGGCAATCAGATGTAGTTCTA
AGTGCTTTTGATAGTCTGCGAATGTGCTGTGCCTACCTCTTTGGCTAGGAGGGGCCTCTGTGTCCTCTCGAGCT
TTCTCCTGACACTGGAGACTGAGCTAGGAAGGGGAAGAGGCAGGTGGTACAAGAAAACAAGGCAGCAGGTGGTG
AGGAAAGGAGGCAGGAGTGAATGAACTAAGCTAAAGTTGGATGAGCGCCTTTCAGTCTCCCAGCTGAGCAGTGCC
GGCACCAAGGCCAAGCATTTTGGTTGTCCCTGTTGGTTTTGCTGACTGTTTAAATTAC
```

FIG. 6 Cont'd

```
TATTCCCCATGGGTGCTATGAGTACCCACCCTGTAGGAGTGGCCAGGGTCTCCTGGAGTTGGAGCTTGTGAACG
GCGAGGAGTCAGAGGCAGCGGGCAGTTAACTCATGTTTGGGCCTGGCTACCTGACTGGGCTCCGCTCCTCTTTT
CTCCAGGTTGTTGCCCACTGCTCGATTTTATGGATTCCGCATGCATTCTGTACCTGCCTGAGACTCCTGTCC
AGACCATCGGCACCTTCATACCTGTCCTGCCCTTCATTCTCGAGGTGACTGTGCTGGGCACAACTCGTGTTGGA
CTTAGAAATGTCTTTAGGAAACCACACCTCCGTCTCTGCGTCTGCCAGTGCTAACTTCTAACAATGACCCCGTG
ACCCCCCTCTCTTTGCAGTCCTTACAGATCTGCATTGAGTCTCTCCAAGTCTCACAGTTACTATGACACCTTTC
TCGTTTTCCTTATTGTACCTCTACCTTGAGTCGCTGTCCCTGCCCTCGGGCTTCCTATCAGGTGCAGATTCCTT
GAGAAAGTGAAGCACAAGGGTGAATCCAAGCCCCTGCTAACACCGACACCGCCCTTTCTTTAGTCTATGGCGAG
GATAAAGGTGGATATTGATAACCAGCTCTATATATTAGTTAGCATCCTTTGCTCAGAGAAAGGACTTTCCCTAC
CTCCAATTTATTAATCACTGTAGCTGGTTCACCTTCTAGCAACATGTTACGTAAGTTCTCTTATCAGGGCTTCC
CTATAGAACCTCCCCTCTCTATGCTTCTGTGTGTACCTTGTGCCTCCTTGGTTTACCTGTTCTGTGTGGGGCAT
CCTCCGACCAAGAGGTTAGGCTAGGCTCCGATTTCCCTCTTAGGAAGGCCAAAGTGTATATAGAGCCTGCAAGG
TTTGTTGGGTGTGGAAAACACAGTCTCCCTTCTGTCTTTCTTTATTGGTGGTTTTGTCCATAGTGCCTGGGATG
CCTGAGGCCCAGATCCGTATCTAAAGGCGGTTAAGTGTATGCAGGCGTCCTTATGGTTATCTGTCAAGGGGCTC
AGGCCTCTGGAAGGCCTGGTCTTGGGGGATCTCTTTGGCTCGGGCTTACACTCTGTGGGTAGATTTTCCAGCAG
GTGGACTTCAATAGGCGGCCAGGTCGCATGAGGTGGAAGCCCATCAAGTTCTGTGGATCTGAAGCTGTCCAG
CACCAACCTGCAGGAGAAGGCGTACCGGTGAGGCTGAACTCAAGGCCTTCTGGGAAGGCCTGGGGCTATGTT
TTAGTTGCTTCACAAGGACTTAATAAGGCCGTTGATATACAAGGGAGGGATTCCCATTGTGGACCATTTGTGGT
TTCTTTTGAGACAAGATCTCTCTATTATATTGCTCTTGCTGTCCTGGAACTTGCTATATTGATCAGGCTAGCCT
TGAACTCACAGAGTTCCACTTTTCAAATGCTAAGATTGAGGTTTTTGTAGTCATGGAGCAATGACTCCTTAATC
TCAGTTCCCGTGAAGCTGGGTGTGGCTTGGGGGGGTCTGTGCGTACTGTTTTATAGCCCTGGTCTTGGACATTG
AGCAGAGTTGGGGTGAAATGTAAGAAAATGGGCTACTGGGCTTCATCATCTGATGAGGTTGGCCTGCCCCCCA
GGACGGGCTGCTGGAACACTGTGTGACCTTACTCTGGAATACCTGCAGAGCCAGGGCCAGACCATGCTTTCC
CAGAGTTGGTGTTGCCTACTGTTCTACAGGTATGTACTCATCATCTGACTTCCTTTCCCTGGCCAGACCTTGGC
GTCCTCCTTGTGGCTATCTTGACAATCTTTTAGTAGGTTTGTCGTCCCCTTATGTTCTAGTCCTGGACCAGTA
GCAACACCGTGTTTATCCAGTTACCAATGGGCTGCCAGATCCATTGGCGCCAGTGCAGGGAGAGAGCGATCATT
TGCCTTGATAGCTTAAGGAACTTTCTCTAGGGACTGTGGAATTAACTTGTAAAGGATTATCGGCCTCTGCTGAA
GTTGGGCTGGGGCTGGGTAACTTAATCAGGATCTCAGGAATTTGCAGACCCTTCCCCAGTCTGACTGGAGCCTA
CCATCAACTATGGAAGTCTAAAGCCTGGGTTGGTCTGGTGCCCGTTTTGTTTTTCCGTGTGGTCATGGTCTCTC
TGTGCCCCTTCTGAGAATCTGTTTGCTCTCAGCTCAGCTATTTTCCATCTAGGTCCTTCTCATAGGAGGGGCT
GGTGCTGTCTCTTTTCTGGTACTGGTAGGGGATTAGATCCATTGCTCACAGACTTGTCGTGGTGTTGCTCATAC
CTGAGCTATGCCTGGGTCAGGCTCCTATGGGCACAGGTGTATGTGTGACGTTACATGTATAGCTGTGCACACGG
CTGTGTCGCGGTTGGTTGCATAATGTGGCATTGGCTTCCCCCTGTGTCCTCTTGGCTGATGATGTCAGGTAGTC
AGGATACCTTTAGTTTTAGGCTCAGCATTTTAGGTGTATGGATGTGTGGATCTAGATAGAAGTTAGCAGATGT
GTTTCAGTTAAAATAAAAGTAGCAAAAAAAAAAAAGAAACTTTTAAGGTTTATGTCTTGTCACAGCTCTTCAT
CTGCTTACCTCTCGGGCTGCGGGGACAAGCATGGTCTTATGCCTGTGAGACCTAAGAGATTGACAGCAGGTCCT
TGTGATTGTCACATGGCTTTTCACTGCTTGGACCCCTCGAGGGTGAGGAATGGAACTGTCACTGGAGCTGTACT
GAGTCTTTCCTTTCTGCAGCTGAAATCTTTTCTCCGGGAGTGCAAAGTGCTAACTACTGCCGGCAGGTGCGCC
AGCTGCTGGAGAAAGTGCAAGAGAATGCACGACACATCCAAAGTCTTCGACAGAGCGCGACCTTCAGCGTGTCT
GACCGGACGGCAGTGGTGGGTTGGACTTGGCATCTGCACTCGAATGGTGCTGCCTGGGGTCACCTGTTAGGGTG
TGGTGGATGTTTAAGGGTTTTCCAGAATGATCATGGTCCTGAATTTACTTCAATCCTTAGGATGCGTGGGAGA
GCAGGTTCGTGAAGAGGGACCCCACTCACAGAATACTATGGCACTGGAGAAGCCTGAGGGACCGTGAGATCC
AGCTGGAAATCAGTGGCAAAGAGCGGGTATGGCTGGGTCTGTGAAGATGGCCTAGTAGAAAGTGGCCAAGCAC
GTTATTTGTAAAGGCTTGGGGCTGAGGGGAGAAGTTGGAAAAGGAAACGAAATCAGGAGGGAAGAAAGAAAG
GTGAGTTTGACTGAACCCTCTAAGTTTCTGTTTACCTGCTGGGCAGCTGGTCCCCGGTATTGATATACATGGTT
CCCGAGGCGCAGCTGGGCCAGTTCTCTCGGCCTCTCCCTACCCTCACTTGTTGTTCTGTTTCTTGGTCCTTGAA
GCTAGAAGACTGAACTTCCCAGAGATCAAAAGGCGGAAGGTGGAAGACAGGAAGGATGAAGACAGGAAGAAT
TAAAGGACCTGTTTGAGTTGGACAGTTCTGAGGGCGAGGACAGCACCGAGTTCTTGAGAGGGTGAGGCCTGA
GCTGGAGTGGTTGAGAGCTGTGTGTGTCTGGGCATTCATGTCTGGCTAGTGGGCAGACCTGGTTTGTTGTTTT
TAATTTTTATGTCTGTGTGTTTTGGCTACATGTCTGTCTGTATCCAGATCCCCCTCAGACTGGAGTTAGAGACAC
TTGTGAGCCTCAGTGTGGGCACTGGGATCAAACCCATGTCCTTGAACCACTGAGCCATCTCTCTAGCCTCCAGA
TCTGTTTTTTTTTTTTTTTTTAAAGATTTATTTATTTATTATATGTAAGTACACTGTAGCTGTCTTCAGACAC
TCCAGAAGAGGGCGTCAGATCTTGTTACAGATGGTTGTGACCCACCATGTGGTTGCTGGGATTTGAACTCAGGA
CCTTTGGAAGAGCAGTCGGGTGCTCTTACCCACTGAGCCATCTCACCAGCCCTAGATCTGTTTCTTATACCACT
CATTGGCCCCTTATGTTTGAGCTGGGGACTCAGTATTGGTAATTGTCACCATGCTGGGGCCTCTATAGGTGGCA
GAGAGGGCTAGTGGCCCTGTTGCTACTGCTGAGACCTGGGGCCCTGTTGCATGTCCAGAGCCAGCCCTCCTGTG
TAGCTACTCATTGCTTTGTTATTTCACCCGGTGTGTGTGTGTGTCTGTGTGTGTCTGTGTGTGTCTGTGTGT
CTGTGTGACGACCGTTCTTCATTTGCAGGAGTACCTAGGCTCCGGAGCCTCATCAAGGACTGAAAGAAGATCA
GGAAGAAGAAGATAAAGAAGAAGGTGACAGCGATTCAGAGGGTAAGTGGTTTCTATAT
```

FIG. 6 Cont'd

```
GAAATAGATTGGCCCTGGAGTCTGTCTGGAGGCCACACCATGGGAAGACAGAGCTCTACGCCAGGCTTCTGCCC
CTCCCTGGGGTGCCAGGCCAGCTGCTCTGTACTCTTTAGCAACCAGCTATAGCATGCTGATAAATTTAATTAAT
GCTGCAATTAATTAGTGATGAGTAACTTCTAAAGCTGGCTTTTTCATGATATAGCAGAATTTATTTATGTGGCC
TCTTCCTTCTCTGTAGATGGAGACACAGACACGGGAGTGGATCTGAGCGAAGTGTGGGAAGCTGGCTGAGGACG
ACAAGATGAGCTGAGGATCTTCAGCTCTCAGAAGAGGACTGAGGGCCTCCTGCTGCCTCCTGGAGGCCTCGAC
AGCAACTGTGCGGCGAGAGGACAGCAGAGCGTAAACAGGCTTTTATTGTTACAGCACAGCAGAACAAGTGTACT
AGGAGCCATTTTGACCCTGAAAGGGAGGGAACTGTTTCTGCAGAGCCTTCTGCTGCCGGAAGCCGAAGGCTGAC
CCTGATGTTGTCCCAGTTCAGAGTGGGGAGGGCGGCTCCATGGCCTCTCCTCTCCACTTTGTCTTTGGTTTGTC
TGCAGAGCACTGCAGTTACCTCTAGAAGATAAACCCATTACTTTTGTTTGTTTGTTTGTTTGTTTGTTTGTTTG
TTTGTTTTTTCGAGACAGGGTTTCTCTGTGTAGCCCTGGCTGTCCTGGAACTCACTCTGTAGACCAGGCTGGCC
TCGAACTCAGAAATCCGCCTGCCTCTGCCTCCCGAGTGCTGGGATTAAAGGTGTGCGCCACCTCTGCCCAGCTC
ATTGCTTTTCTTCTTAAGCCTTATGTTTTCCTTTTAAGAACTCTCGGCATTTTGCATCTAAAAAGGGGAAA
TACCCTGGGGCGGAGTGAGGTTAGCAATTTGACTGGGAATCACGGAGTATGACGGTTGCCTGCCGGATCATTG
GAGAAGCTGGGAAGGGTCTGGGGCACCTGAAAGCAGAGCTATGGTCCCTGACCCATTCTCCTGCTTGGGTGAGG
CTTGTCCTGTGGGCAGGTGGGTCCCTTCATACGGGGAGGTGGTGGTTGCTGGCGACAGAGGTTGATGTCCTGGG
CTGAGCTCAGGTGCTTGCAGGCTTGGTGGCTGCAGCGGCAGGGCCACAGGGAAGCTGGCCATGTAGAAGACACG
GCCCAGGCGCTTGGCCACCTACAAAGAGACGAAGCTGGGTGAATACCTGCTAGGTAAAGGCGCCTAGGGAAACA
ACTCCAGGTACAGAGAATCCTAAAACCCTCTCTAGAGTGGTGAAAACACTGGACAAACTTACTTGTGCCCTGAT
CTTGAGGGCAGGCCCTAGCTTCAGTCCCATGGTGTTCAGAAGGTGCTCTTCTGTCAGTAGAGGCAAAGTCTCTC
CGTCTATTCCTTGTTCTCTGAATACCTGGGGACAAGGTGGGCCCATAGAGTAGAGTTGTAGAGCTTGCATGGAA
AAATAACAAAAGGAAAGTTCTTTTTTGTGGGAGACCGGGACATTGTCCAGAACTGGGCCAGAACCCTAGGGACC
TGCCACTCCCCTCACCCTGGCATACTCGCCACAGCCAGAAAGGCCCCCCACGAAGTTGCAGACATCATCTACAG
TCCACTTGTTGACATCCTCAAGGGTTGTGGTCTCCTCATCAGTGAAGAGCCCCCCATGGTACCTGGAGATAGA
AAGGATGTCACTAGGGCTTGGGCTTTCCCATTTCTTTGCCTCCTTCCCCACTGGCTGACCTTTCTCTGAATTGG
TAAAGTCTTTGGCTTAATGACAAATGATTTTTCTCCCCACGGGATCCCCTATCAGTGGGTGACTAAGGCTGCCC
ACCTGTGTGGAAGTAGGGGCTCACTGCCCCGCAAGGGAATCCCAGGGGCAGTGGAGGGGGCAGTGTGGACCCTG
ATAGAAGCCCCCTTCCTTCTGCTCTGGTCCCTCCTGCTGGGACTTGGCTGGGAGTGGAGGTCCCTTCCCTGGCA
GCTGCTGTCTCGGGGTCCTCTCCATCTGAGTCCTTGGATGGCTCCTCAGAGACTTCTTGAGCCCAGAGGCCAGC
CCCTGTCGTCTCCTTGGGTTGGCTGGGCTGGACACCAAGGCTCCCCTTTTCGGACCGGCTTCGAGCAGACTCCT
TGGGTGGGATAGGGGGTCCTGGGCCTGGGGGTCCCTGGGGTGGCAGGGCCAGTAGTGGTGCTGAGCTGTGTTTC
AAAACCAGCATGGAGCCACGTCGCTGCAGTTCGTCGGGACCCTCGGGGATATGCAAGGCCACCTCTGGTGCCGG
TAGCAGTGGCCGGTGAACACTGCCCAGTTCTTTCTGCCTAAGCAACTCTGACATTTCCAGCCTGACCAAAAGG
ACAGACGAGTCAGCCTGGGCACGCTTAGAACTGCTCCCGCTGGCCTTGCAGTCGCTTACCGAGCCAGGCTCTGC
TTCCGTAGAAGTTCCTGCTGCCGAGCTAACATCTCAGCTGGGCGGAGGGTAGGAAGCTGAAACCTGGGATAGA
AGAAAAGGCTGCTGAAGCCGGATGCTCTTCACTACTTTTATCTATCTGCCTAAAGAGAGCCTCATAGGAACACA
AACGGCTTACATACCCGACTTTCTCACCTGGGGTCTGACACACAGCTGTGGGCATCCCCAGAAAAGGAGGCGGG
AGATGGGAGCTCATTGTGATGTGGGCGGCATTCTGGGGTGACAGCAAAGGGGGTGGCTGTGACATTTCCCTGTG
GACAGCAGAATAGTGAGCACATGCCTAGGTCCGTCTGTGCACACCCCCTCTTTCCTGTCATCACCTCTGGGTGC
ACCCCTGCTAACCCTTCTAGTTGCCGACCCCTCAAGTGGCCGTTGGTTTCCTGATTATGGCTTGCTTGTGTACA
CACACACACACACACACCCCGCGCGCAAGTCTCCTTGTCAGCACAGAGGCAATGGCCCCATGGGCCACAC
TGCGTCAGTAATTACCGGGGTGGGGATACCTCTCGAGCAGTGAGGAGGGGAGGGGTGCAGGACAGGGCAAT
TAGCCCCAATTTGTAGATGTGGCAGATGCTGCAGTCTGCCAGGATCAGGGTGAGATAGGATGTGTTTGGGAAAC
CCGGGGACCCTGCCTAATGCTCTCCTTGGCTTAACTCGTCTGCCGCGGAGACTACTGTGAGCATGATGTCTCTG
CAGTTTATAGCAGGGTAGGGATGAGGGGGCGTATGTCCTTCACTCTGAATCCTCTGTGGTTGCTTTCTCCTTG
CCTTCCTCAACATCCCACCACCACCACCTGTGAGGGGAGGGCCTCTGCTCTCGGGGCAGCTCTACTAGGCTGGA
ATAGTCAGAGTTGCTTGACAAGAAAATTGTATTTGGCATTCTTGCCAGGGAGTGGGCATTTCTGCATATTTTGC
CCCCCAAATTGAGTCTTTGCAGTAGTTTTAGGAGCTTCCTGCAGTGGACCTTGAACGTGGTGAATGCATTATGC
ATATATGTGATGGAAGACTCAAGGGAAAGAAAGAATTGGCCTTCTCAAGTAACAAGCATAGCATGTGGGGCCTT
GCTGAAGCACGTCTTAATACCTTTCAGAGAAAGATGTGGCAGCAGCTGGAACCGCCCCTTCCCGGCGCTGAACT
AGGCCTTGCTTCCGTCGATGGTCTGCTGTAGACGAGGGCAGGTGAACTTCCAAGCCACTGGGACCCCTCAGTGT
TGCAGTTGCTACTTCCTGGCGTACCCTAAGCAGATCTGAGAAGGGAGGTGATAGCGGGCCCCCTGATAAGCTC
CCGTAGGATTTCCCCTTTCCATCTTGGTGAGCAGGGCATTGGCCCGGTGAAGGTATGAACAGAGTGGGAGGAGG
AGACTCTCACATGTCCTGAGCCTGCTTTTGTGTCACAGGCTAGAGGATCAGCAGGGAAGGCACTTTGCTTTAAC
ACCTACATGCTGTAGCCAGGCAAGTGAACTTGAAAAGGAATGTGAATAAGTAGGTCATCGAAACTGGAGAAGAA
AGGCTCCAACATGTAGAGTATTAGTGCTAATTTGGTTTGAATATTCACAAGGTCAGAGGTGGAAGGGCATAGGG
CTGCTCCAAGTAGGTGAGTGGGACAAGAGTCTATGGATTAGGAGGGGACCTCAAACAGAAGCCTGCCCAGGTAA
CTCCTTTCTAGACAGGAGACAAGAACAGGAAGGACTTGCCGTCCCTATAAAGCGATTCATAGCATACATGGTTA
TAATAGCAGATACCACTGACTAGCAGCAACACACAATCACAGACCTGCATGGTTGTGCCCCATTGCATTTAGG
AAGAGCGGAGGCTCCGAGCCCCTTTAATCCACCTGCTCAAGCTCCACTTCTCTACCGC
```

FIG. 6 Cont'd

```
TCTGCCTGTTTATAAATCACGTAGCTGAAAAAGGGACGTGGGCCTAGCTAGGGCTTGAAGCCAAATCCCAGACC
CTAATAAGCCCAGGCCACCCCAGTCATGCGCCACGCAATGGTGATTGACAGCCAGCTTGCTTGCACAGTCTCCT
GCACAGGCCAGCAGAGCTGGGTAAGCAATTAAAAAGAAAGATTTTTAAATTATTAACATTTAGTGAATTATTCA
GGCTCTCGGTGCCTGAGCTGCTGCCCTAGGGAACAGCGCCTTCTGCAAGAATCAGGAATCCTTTTCCCTTCTCT
GAGCCCCCGTCCACTTCTGCCAGAAAAGACAAGATTTGTCCGGTGCTGTAGCAGCACAGGGTGTCTCACAAGTC
CTCGGTAGCAAGGACGGTGCCTCAAGGCTTGGCTTCCCTCAAGCAACCTGGGGTGCATCCTGACTGTGACGCAG
GTTCCTATTTTTGCCATGCCCTCCTCCCTGTGTATCAACAAAACCTGAAAAGTCTGACACAGCATCAACACGAC
CACAGATTCACGTATTGCACTGACCACTCTGGGAGAAACTAGCACAGGCCAGAGGCCACATCTCTTCAACAAAG
AACAGGTGAACAAACTCTTCTGTCCCACCCTCACCTGGGCTCCTCGGGGACGCACAGTAGAGGACTGAGGCCAG
TGAGGCTGCATCACTACCCGGAAGCCCTTCTATGTATTCAATCCTGGTCTTGGTGTTGACCTCCAAGCATCCAG
ATCTTTTTCTTGGGGTTGGCTTAGTGGGGTGGAAAGGTAAGAGAGATTTGGCTCACTTGAAGTCTGAGCGCCGG
CCGTGGGGGTGGCACATACCGTGGCTGGGGATACCCAAGTGGTAGAGACGTTGAGTTTCCTCAAAGGAACTGGC
CTCACTCAGGGCCGACATAAGCTGATGGTAGTGGTCCTCAGGGGCCATTGTAGACTCTAGCTTGGGAAGCAGCG
AAGTCGCTGTTGGACAGAGCACATGGTGAGGACCACGGGGAAAGTCAAGGCTTCTTATGGTTTCCACCCAAGGT
CTGGGGAGCCCTTCAGGACCCAGTTGCTCCCCCCCTTCCCTGTGACCTGCATCCTTTTCCAGAGTCGGGCTTTC
ACCTTGGGGGTCCTTGCTTCTGGCCTTCTTCTCTGAAGAGCAGTGACTGGTGATGCAGGGGCAGCTCAGCCTCT
TGCCCAACAGGTCGCCTGTAGAGGATAGAGTGAGCCCCACCCAGTGTCTCATGGCTTCGAGAGAAAGCCATCTC
TGCCTTAGCTCAGTCTGGAGCCCCAATCACCACTATGTTCTCCCTGGCAGTTAAAGACCTTGTCCGATCTGGTG
TCCCAGGCTAGAGAGCACGATGACAGGTAGATGGAGAGTGCAGTAAAGACAAAGCGATCCTGACGCTGGCCTTG
GGCACGTAAGTAACAGTGAGAGCTCTGCATCAGTGTTTCCCCAGTCAGTCTCCTGTAAGCTCCTTGCCTCTCCC
CTCGGTGCATTTGCCCATCTGCATATCCAGGTCTGGGTTCTTAATGGGACTCCTAAGCATTTCACTCCATAGTG
CACAGTCTATATGTGCTATGCTTTTATGAGGCCAGGCCAGACACTGCTTACAATATCCCCAGAGATAATACATG
CCGAATCTCAGGCATTAATTGACCCAATTCCAGACTGGCCTGAACACTGCTGCCTAACTTCCTCCTGAGCTCCT
GCCCTGAGGCTAGGGCCTTTGCTGAACAGCCCATGACATCGCCATCATGGCTTCAAGCTAAGGTTCCTGTCTCT
GCCCTCCTTATCCTCACCAGCTAGGGGAGTGTGGAGGAACAATTCCGTGGGTGATTCAAAATCTCCATAATGCC
CAATAAGGGGCTGCTTCTACTTGTGTGCCCACCCTCCCTCAAAGCTGGTGGTGTCAGCGCCAGGACTGAATTCC
ATTTAAAAAAAATTCCTTAATTTGTCATTTTTATCAGATTGGGGAAGTGTGGCAGCAAAAACGCTGATCAATCT
CCACGTTATGGCTGACAGAATGGTGCTAATAACTTATTGATCTCAACTACCTCACTGCTGTTAGTCTAGCAGGC
CATCTCAGCCTCCGCCCAGAGAAAGAGACAGCGCCTACTGTCTGGACAAGGGCTCCACCCATAATATCTCAAG
GCAGATGGGTCCAGCAGACAGATAATGGGTATCTGGCTTCACTTGGTGCCACCAATAGTTTATCAGAGACCAGT
AGGCAGAAGAGGCAGCAGCTGGAGTAGACAGGAAGGAGGGTCCCTCAGGTCTGTGTGGCCTGGTCTCACTCACT
TTGTACCTGTTATTCTTGTCCCAACCCACAGATCCCCTTTAAGGACTAGGCAAGGGCTCTTTTCACAGCAGTCT
ATTCTCACTTTAAAAGTGGCTACCCCCAAAGGAGAGGGGAGGGAGAGAGGGAGAAAAGGAGG
```

Figure 7

| | | | | | |
|---|---|---|---|---|---|
| BI090012 | cervix | R50543 | breast | BI870713 | liver |
| BG335512 | placenta | H26449 | breast | BE253493 | eye |
| BE903516 | placenta | AI674272 | uterus | BF345524 | brain |
| BG699598 | brain | AI282823 | esophagus | BE070314 | breast |
| BI828140 | brain | RI0573 | pool | AW375280 | colon |
| BG763998 | skin | RI0574 | pool | BG388020 | prostate |
| BG760638 | skin | AW058011 | thymus, pooled | BG179766 | prostate |
| BE894669 | skin | AI660736 | thymus, pooled | BE383040 | brain |
| BG767001 | skin | AI765077 | kidney | BG764329 | skin |
| BF207343 | brain | AI677761 | pancreas | BE263417 | lung |
| BG337689 | uterus | AI266034 | lung | BE266643 | lung |
| BG394462 | eye | AI948457 | kidney | BE273581 | kidney |
| BF212645 | bone marrow | AA281338 | tonsil | BG674251 | skin |
| BE278111 | placenta | AA215719 | tonsil | BE514600 | ovary |
| BF984755 | small intestine | AI193564 | lung | BE778203 | eye |
| BG332620 | lung | AI185822 | lung | BI258705 | placenta |
| BG767665 | skin | AI660558 | colon | BI006483 | kidney_tumor |
| BG764689 | skin | AI681255 | lung | AW675721 | cervix |
| BG390277 | prostate | AI272873 | colon | BE871785 | colon |
| BI489732 | pooled brain, lung, testis | AI935918 | pancreas | BE545263 | placenta |
| | | AI799853 | prostate | BE746375 | ovary |
| BG776759 | lung | AI655977 | germ cell | AI989734 | colon |
| BG029437 | breast | AI633340 | germ cell | AW375221 | colon |
| BG699275 | brain | AI971531 | germ cell | AW365263 | head_neck |
| BE883535 | uterus | AA026277 | heart | BE746427 | ovary |
| BI459847 | testis, cell line | AA036278 | heart | AW375244 | colon |
| BI461880 | testis, cell line | AI400930 | prostate | BI15120 | muscle |
| BG830390 | pancreas | AI420991 | prostate | AI471616 | kidney |
| BI760633 | pooled colon, kidney, stomach | AI682274 | prostate | AL529521 | brain |
| | | AI744703 | colon | BE779713 | eye |
| BE732072 | placenta | AI810704 | prostate | BI256811 | placenta |
| AI254710 | colon | BE869684 | colon | AW237492 | kidney |
| AI611186 | uterus | BE900176 | placenta | AW179094 | stomach |
| AI990470 | thymus, pooled | AW572690 | lymph | AW512856 | uterus |
| AW028378 | stomach | BF868966 | lung_tumor | BE792414 | lung |
| R73178 | breast | BF346952 | brain | AW366003 | head_neck |
| R73124 | breast | AW673372 | cervix | AW104543 | pool |
| AI678640 | stomach | BI085040 | salivary gland | BE257381 | eye |
| R30640 | breast | BE515227 | uterus | BI222365 | placenta |
| | | BE410145 | placenta | BE391125 | uterus |

Figure 7 Cont'd

| | | | | | | | |
|---|---|---|---|---|---|---|---|
| BE746352 | ovary | AW365268 | head_neck | AW083558 | colon |
| AW366001 | head_neck | BG248934 | kidney | BE783940 | eye |
| BF874087 | lung_tumor | BE892013 | skin | BG327104 | kidney |
| AA427964 | whole embryo | BE543377 | placenta | BF734506 | amnion normal |
| BE740821 | ovary | AW674628 | placenta | AW071075 | breast |
| AL526148 | brain | AW351591 | colon | T16895 | brain |
| BF341263 | brain | BF883105 | lung_tumor | BF773461 | epid_tumor |
| BE262764 | brain | AW151790 | stomach | BG284070 | prostate |
| BI115932 | lung | BE391864 | uterus | AW366039 | head_neck |
| BE391378 | uterus | BI254811 | placenta | BG436830 | lung |
| BG576365 | breast | BE301196 | kidney | BE264490 | lung |
| BI259365 | placenta | BE296203 | muscle | BG829981 | pancreas |
| BG330302 | lung | BE2783632 | placenta | AA315693 | ATCC 111476 |
| BI772656 | pooled lung and spleen | BF797114 | lymph | T19249 | testis |
| | | BI857618 | breast | AW364797 | denis_drash |
| BG761400 | skin | BG256028 | prostate | BF223807 | germ cell |
| BG681166 | skin | AI526094 | brain | AA355948 | ATCC 158121 |
| AW365999 | head_neck | AW364731 | denis_drash | BI007523 | kidney_tumor |
| BE841886 | stomach | BF765941 | colon_est | AW351978 | head_neck |
| BE379093 | uterus | AW364764 | denis_drash | AW582985 | pancreas |
| BF768551 | epid_tumor | BE070313 | breast | BE727721 | skin |
| BE898791 | ovary | BF026243 | skin | AW366053 | head_neck |
| BE260929 | brain | AW364773 | denis_drash | BF309501 | muscle |
| BI857073 | breast | AW673544 | cervix | BF820822 | kidney_tumor |
| BF883094 | lung_tumor | AW375245 | colon | BG110646 | bone |
| BE882355 | uterus | AW375242 | colon | BI084625 | salivary gland |
| AW473561 | uterus | BF907757 | uterus_tumor | BI033036 | nervous normal |
| BG421457 | kidney | BG762271 | skin | | |
| BE901462 | placenta | AI632288 | germ cell | AW366052 | head_neck |
| AW351639 | colon | AA427857 | whole embryo | BF593548 | germ cell |
| BI859530 | breast | BE795961 | lung | BI860984 | breast |
| BG911714 | brain | T16894 | brain | AW366056 | head_neck |
| AW375257 | colon | AW366050 | head_neck | AW364784 | denis_drash |
| AA502771 | colon | BE383442 | brain | BG253158 | liver |
| BE742897 | ovary | BF817292 | colon_ins | BF858431 | prostate_tumor |
| AW020647 | ear | AI346323 | colon | BF955772 | nervous normal |
| AI372826 | colon | BF00005 | colon | AW366040 | head_neck |
| BG330696 | lung_tumor | BI160700 | pancreas | BG423930 | kidney |
| BG421512 | kidney | BG177975 | prostate | AA449674 | whole embryo |
| BE536984 | cervix | BI857814 | breast | BF913827 | uterus_tumor |
| AW375211 | colon | BI033334 | nervous normal | AW074084 | genitourmary tract |
| BF732410 | ovary | | | AW328624 | cervix |
| BE273057 | kidney | AW366007 | head_neck | BG030810 | breast |
| AW365264 | head_neck | AW375312 | colon | BG110635 | bone |
| AW365167 | head_neck | BI762663 | pooled colon, kidney, stomach | AL363470 | brain |
| AW375277 | colon | | | AW365161 | head_neck |
| AW375314 | colon | | | BI007446 | kidney_tumor |
| AW594248 | germ cell | AW272745 | colon | BF338161 | brain |
| BE389202 | uterus | AW675196 | placenta | AW387299 | stomach |
| AI636573 | germ cell | AW179097 | stomach | AW601835 | breast |
| BE746451 | ovary | BF338242 | brain | AW601811 | breast |
| BF868950 | lung_tumor | BE896763 | skin | BF846205 | lung_normal |
| BE729701 | skin | | | BG234482 | prostate |
| AW806654 | stomach | | | | |
| BG281880 | skin | | | | |
| BI094540 | cervix | | | | |

A

B

Figure 21
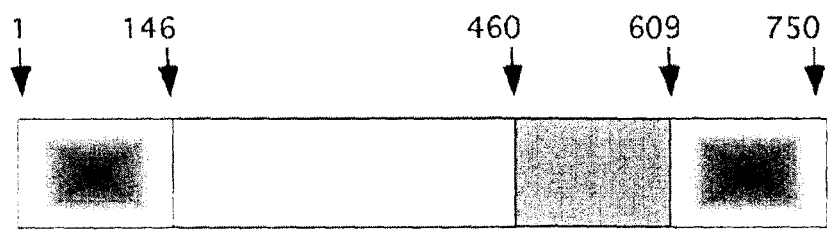
interaction test
not possible due
to lack of protein
 no interaction detectable
hormone or antagonist independent
 interaction with f.l. hAR detectable
interaction is independent of agonist or antagonist

```
                              SEQUENCE LISTING

<160> NUMBER OF SEQ ID NOS: 31

<210> SEQ ID NO 1
<211> LENGTH: 2250
<212> TYPE: DNA
<213> ORGANISM: Homo sapiens

<400> SEQUENCE: 1
atggcagctg cggggagccg caagaggcgc ctggcggagc tgacggtgga cgagttccta      60
gcttcgggct ttgactccga gtccgaatcc gagtccgaaa attctccaca agcggagaca     120
cgggaagcac gcgaggctgc ccggagtccg gataagccgg gcgggagccc ctcggccagc     180
cggcgtaaag gccgtgcctc tgagcacaaa gaccagctct ctcggctgaa ggacagagac     240
cccgagttct acaagttcct gcaggagaat gaccagagcc tgctaaactt cagcgactcg     300
gacagctctg aggaggaaga ggggccgttc cactccctgc agatgtgct ggaggaagcc      360 agtgaggagg aggatggagc ggaggaagga gaagatgggg acagagtccc cagagggctg     420 aagggggaaga agaattctgt tcctgtgacc gtcgccatgg ttgagagatg gaagcaggca     480
gcaaagcaac gcctcactcc aaagctgttc catgaagtgc tacaggcgtt ccgagcagct     540
gtggccacca cccgagggga ccaggaaagt gctgaggcca acaaattcca ggtcacggac     600
agtgctgcat tcaatgctct ggttaccttc tgcatcagag acctcattgg ctgtctccag     660
aagctgctgt ttggaaaggt ggcaaaggat agcagcagga tgctgcagcc gtccagcagc     720
ccgctctggg ggaagcttcg tgtggacatc aaggcttacc tgggctcggc catacagctg     780
gtgtcctgtc tgtcggagac gacggtgttg gcggccgtgc tgcggcacat cagcgtgctg     840
gtgccctgct tcctgacctt ccccaagcag tgccgcatgc tgctcaagag aatggtggtc     900
gtatggagca ctggggagga gtctctgcgg gtgctggctt tcctggtcct cagcagagtc     960
tgccggcaca agaaggacac tttccttggc cccgtcctca agcaaatgta catcacgtat    1020
gtgaggaact gcaagttcac ctcgcctggt gccctcccct tcatcagttt catgcagtgg    1080 acctttgacgg agctgctggc cctggagccg ggtgtggcct accagcacgc cttcctctac    1140
atccgccagc tcgccataca cctgcgcaac gccatgacca cccgcaagaa ggaaacatac    1200
cagtctgtgt acaactggca gtatgtgcac tgcctcttcc tgtggtgccg ggtcctgagc    1260
actgcgggcc ccagcgaagc cctccagccc ttggtctacc cccttgccca agtcatcatt    1320
ggctgtatca agctcatccc cactgcccgc ttctacccgc tgcgaatgca ctgcatccgt    1380
gccctgacgc tgctctcggg gagctcgggg gccttcatcc cggtgctgcc tttcatcctg    1440
gagatgttcc agcaggtcga cttcaacagg aagccagggc gcatgagctc caagcccatc    1500
aacttctccg tgatcctgaa gctgtccaat gtcaacctgc aggagaaggc gtaccgggac    1560
ggcctggtgg agcagctgta cgacctcacc ctggagtacc tgcacagcca ggcacactgc    1620
atcggcttcc cggagctggt gctgcctgtg gtcctgcagc tgaagtcgtt cctccgggag    1680
tgcaaggtgg ccaactactg ccggcaggtg cagcagctgc ttgggaaggt tcaggagaac    1740
tcggcataca tctgcagccg ccgccagagg gtttccttcg gcgtctctga gcagcaggca    1800
gtggaagcct gggagaagct gacccgggaa gagggacac ccttgacctt gtactacagc     1860
cactggcgca agctgcgtga ccgggagatc cagctggaga tcagtggcaa agagcggctg    1920
gaagacctga acttccctga gatcaaacga aggaagatgg ctgacaggaa ggatgaggac    1980
```

| | |
|---|---|
| aggaagcaat ttaaagacct ctttgacctg aacagctctg aagaggacga caccgaggga | 2040 |
| ttctcggaga gagggatact gaggcccctg agcactcggc atggggtgga agacgatgaa | 2100 |
| gaggacgagg aggagggcga ggaggacagc agcaactcgg aggatggaga cccagacgca | 2160 |
| gaggcgggc tggcccctgg ggagctgcag cagctggccc aggggccgga ggacgagctg | 2220 |
| gaggatctgc agctctcaga ggacgactga | 2250 |

```
<210> SEQ ID NO 2
<211> LENGTH: 2253
<212> TYPE: DNA
<213> ORGANISM: Mus musculus

<400> SEQUENCE: 2
```

| | |
|---|---|
| atggctgcgt ctcgcgctcc ccgcaggcgc ctggaggacc tcagtgtgga cgagttcctg | 60 |
| gcttccggct tcgagtccgg atccgagtcg gagctggagg gcgccgcgga ggcggcggcg | 120 |
| gaggagcgca gggcgcgagg agccgcgtgg aaccgggagc ggcggggcgc gcgcacctcc | 180 |
| ccgggccccg caggacgccc gcgtaagggc cgcgcctctg agcacaaaga ccagctctct | 240 |
| cggctgaagg acagagaccc cgagttctac aagttcctgc aggagaatga ccggagccta | 300 |
| ctggacttca gtgactcgga cagctctgcg gaagaagaag agccattcca ctccctgcca | 360 |
| gacacgctgg aggaagcgag cgaaacagag gaagacggag gagaggacag tgacgcgttg | 420 |
| cccagagggc tgaggagcaa gaagaatgag cctgtacccg tgaccctcgc catggtggaa | 480 |
| aggtggaggc agggctccag gcaccacctt agtcccaggc tgttccatga agttgtacag | 540 |
| gcgttccgag cagctgtagc caccacccaa ggagagcagg aagctgctga acttgcagg | 600 |
| ttccaggttg cagatagtgc tgtgttcaat gctctggtta cttctgcat tcgagacctc | 660 |
| tgtggttgcc ttcagaagct gctgtttgga aagacaccaa aggatagcaa taggctgctg | 720 |
| ccatccagta gcccactgtg ggggaagctc cgtgtggatg tcaagacata cctaagtgcg | 780 |
| gtkgtgcagc tggtagcctg tctagcggaa gcccagtgt ctgcagctgt cctgcagcat | 840 |
| atcagcagct tggttcctta cttcctgact ttcccgaagc agtgccgaat gctgctcaag | 900 |
| aggatggtgg ttctgtggag cacgggtgaa gagtctctgc gggtcctggc cttcctggta | 960 |
| ctcatcagag tctgtcggca caagaaggaa gccttccttg gtcccattct gaagcaaatg | 1020 |
| tacatcatgt atgtgagaaa ctgcaagttc acctccccca gtaccctccc cctcataagc | 1080 |
| ttcatgcagc ggacactgac tgaaatgctt gccttggacc ccagcgtctc ctatcagcac | 1140 |
| gccttcctct acatccgcca gcttgccgtc cacctgcgga atgctatgac cacaggcaag | 1200 |
| aaggagacac accagtctgt gtacaactgg cagtatgtgc actgcctcta cctgtggtgt | 1260 |
| cgwgtcctga gtacccttgg ttccagtgag atcctgcagc cgctactcta ccctctctca | 1320 |
| cagatcatca ttggctgtat caagttgttg cccactgctc gattttatcc attgcgcatg | 1380 |
| cattgtgtac gtgccctgac actgctgtcc cagaccatcg gcaccttcat acctgtcctg | 1440 |
| cccttcattc tygagatttt ccagcaggtg gacttcaata ggcggccagg tcgcatgagc | 1500 |
| tccaagccca tcaacttctc tgtgatcttg aagctgtcca gcaccaacct gcaggagaag | 1560 |
| gcgtaccggg acgggctgct ggaacagctg tgtgaccta ctctggaata cctgcacagc | 1620 |
| caggcccaca gcatcgcttt cccagagttg gtgttgccta ctgttctaca gctgaaatct | 1680 |
| tttctccggg agtgcaaagt ggctaactac tgccggcagg tgcgccactm gctggagaaa | 1740 |
| gtgcaagaga atgcacaaca tatccaaagt cttcgacaga gcgcgacctt cagcgtgtct | 1800 |
| gaccggacgg cagtggatgc gtgggagaag caggttygtg aagagggac cccactcacc | 1860 |

```
agatactacg gccactggaa gaagctgagg gaccgtgaaa tccagctgga aatcagtggc    1920
aaagagcggc tagaagacct gaacttccca gagatcaaaa ggcggaaggt ggaagacagg    1980
aaggatgaag acaggaaaga attaaaggac ctgtttgagt tggacagttc tgagggcgag    2040
gacagcaccg acttctttga gaggagta cctaggctcc cagaagctca ccaaggactg      2100
aaagaagatc aggaagaaga agataaagaa gaaggtgaca gcgattcaga ggatggagac    2160
acagacacgg gagtggatct gagcgaactg tggcagctgg ctcagggacc acaagatgag    2220
ctggaggatc ttcagctctc agaagaggac tga                                2253
```

```
<210> SEQ ID NO 3
<211> LENGTH: 749
<212> TYPE: PRT
<213> ORGANISM: Homo sapiens

<400> SEQUENCE: 3
```

```
Met Ala Ala Gly Ser Arg Lys Arg Arg Leu Ala Glu Leu Thr Val
  1               5                  10                  15

Asp Glu Phe Leu Ala Ser Gly Phe Asp Ser Glu Ser Glu Ser Glu
                 20                  25                  30

Glu Asn Ser Pro Gln Ala Glu Thr Arg Glu Ala Arg Glu Ala Arg
                 35                  40                  45

Ser Pro Asp Lys Pro Gly Gly Ser Pro Ser Ala Ser Arg Arg Lys Gly
 50                  55                  60

Arg Ala Ser Glu His Lys Asp Gln Leu Ser Arg Leu Lys Asp Arg Asp
 65                  70                  75                  80

Pro Glu Phe Tyr Lys Phe Leu Gln Glu Asn Asp Gln Ser Leu Leu Asn
                 85                  90                  95

Phe Ser Asp Ser Asp Ser Ser Glu Glu Glu Glu Gly Pro Phe His Ser
                100                 105                 110

Leu Pro Asp Val Leu Glu Glu Ala Ser Glu Glu Glu Asp Gly Ala Glu
                115                 120                 125

Glu Gly Glu Asp Gly Asp Arg Val Pro Arg Gly Leu Lys Gly Lys Lys
            130                 135                 140

Asn Ser Val Pro Val Thr Val Ala Met Val Glu Arg Trp Lys Gln Ala
145                 150                 155                 160

Ala Lys Gln Arg Leu Thr Pro Lys Leu Phe His Glu Val Val Gln Ala
                165                 170                 175

Phe Arg Ala Ala Val Ala Thr Thr Arg Gly Asp Gln Glu Ser Ala Glu
                180                 185                 190

Ala Asn Lys Phe Gln Val Thr Asp Ser Ala Ala Phe Asn Ala Leu Val
                195                 200                 205

Thr Phe Cys Ile Arg Asp Leu Ile Gly Cys Leu Gln Lys Leu Leu Phe
            210                 215                 220

Gly Lys Val Ala Lys Asp Ser Ser Arg Met Leu Gln Pro Ser Ser Ser
225                 230                 235                 240

Pro Leu Trp Gly Lys Leu Arg Val Asp Ile Lys Ala Tyr Leu Gly Ser
                245                 250                 255

Ala Ile Gln Leu Val Ser Cys Leu Ser Glu Thr Thr Val Leu Ala Ala
                260                 265                 270

Val Leu Arg His Ile Ser Val Leu Val Pro Cys Phe Leu Thr Phe Pro
                275                 280                 285

Lys Gln Cys Arg Met Leu Leu Lys Arg Met Val Val Trp Ser Thr
            290                 295                 300
```

```
Gly Glu Glu Ser Leu Arg Val Leu Ala Phe Leu Val Leu Ser Arg Val
305                 310                 315                 320

Cys Arg His Lys Lys Asp Thr Phe Leu Gly Pro Val Leu Lys Gln Met
            325                 330                 335

Tyr Ile Thr Tyr Val Arg Asn Cys Lys Phe Thr Ser Pro Gly Ala Leu
        340                 345                 350

Pro Phe Ile Ser Phe Met Gln Trp Thr Leu Thr Glu Leu Leu Ala Leu
    355                 360                 365

Glu Pro Gly Val Ala Tyr Gln His Ala Phe Leu Tyr Ile Arg Gln Leu
370                 375                 380

Ala Ile His Leu Arg Asn Ala Met Thr Thr Arg Lys Lys Glu Thr Tyr
385                 390                 395                 400

Gln Ser Val Tyr Asn Trp Gln Tyr Val His Cys Leu Phe Leu Trp Cys
                405                 410                 415

Arg Val Leu Ser Thr Ala Gly Pro Ser Glu Ala Leu Gln Pro Leu Val
                420                 425                 430

Tyr Pro Leu Ala Gln Val Ile Ile Gly Cys Ile Lys Leu Ile Pro Thr
            435                 440                 445

Ala Arg Phe Tyr Pro Leu Arg Met His Cys Ile Arg Ala Leu Thr Leu
450                 455                 460

Leu Ser Gly Ser Gly Ala Phe Ile Pro Val Leu Pro Phe Ile Leu
465                 470                 475                 480

Glu Met Phe Gln Gln Val Asp Phe Asn Arg Lys Pro Gly Arg Met Ser
                485                 490                 495

Ser Lys Pro Ile Asn Phe Ser Val Ile Leu Lys Leu Ser Asn Val Asn
            500                 505                 510

Leu Gln Glu Lys Ala Tyr Arg Asp Gly Leu Val Glu Gln Leu Tyr Asp
    515                 520                 525

Leu Thr Leu Glu Tyr Leu His Ser Gln Ala His Cys Ile Gly Phe Pro
530                 535                 540

Glu Leu Val Leu Pro Val Val Leu Gln Leu Lys Ser Phe Leu Arg Glu
545                 550                 555                 560

Cys Lys Val Ala Asn Tyr Cys Arg Gln Val Gln Gln Leu Leu Gly Lys
                565                 570                 575

Val Gln Glu Asn Ser Ala Tyr Ile Cys Ser Arg Arg Gln Arg Val Ser
                580                 585                 590

Phe Gly Val Ser Glu Gln Gln Ala Val Glu Ala Trp Glu Lys Leu Thr
                595                 600                 605

Arg Glu Glu Gly Thr Pro Leu Thr Leu Tyr Tyr Ser His Trp Arg Lys
                610                 615                 620

Leu Arg Asp Arg Glu Ile Gln Leu Glu Ile Ser Gly Lys Glu Arg Leu
625                 630                 635                 640

Glu Asp Leu Asn Phe Pro Glu Ile Lys Arg Arg Lys Met Ala Asp Arg
                645                 650                 655

Lys Asp Glu Asp Arg Lys Gln Phe Lys Asp Leu Phe Asp Leu Asn Ser
            660                 665                 670

Ser Glu Glu Asp Thr Glu Gly Phe Ser Arg Gly Ile Leu Arg
            675                 680                 685

Pro Leu Ser Thr Arg His Gly Val Glu Asp Glu Asp Glu Glu
    690                 695                 700

Glu Gly Glu Glu Asp Ser Ser Asn Ser Glu Asp Gly Asp Pro Asp Ala
705                 710                 715                 720

Glu Ala Gly Leu Ala Pro Gly Glu Leu Gln Gln Leu Ala Gln Gly Pro
                725                 730                 735
```

-continued

Glu Asp Glu Leu Glu Asp Leu Gln Leu Ser Glu Asp Asp
                740                 745

<210> SEQ ID NO 4
<211> LENGTH: 750
<212> TYPE: PRT
<213> ORGANISM: Mus musculus
<220> FEATURE:
<221> NAME/KEY: MOD_RES
<222> LOCATION: (577)..(577)
<223> OTHER INFORMATION: variable amino acid
<220> FEATURE:
<221> NAME/KEY: MOD_RES
<222> LOCATION: (613)..(613)
<223> OTHER INFORMATION: variable amino acid

<400> SEQUENCE: 4

Met Ala Ala Ser Arg Ala Pro Arg Arg Leu Glu Asp Leu Ser Val
 1               5                  10                  15

Asp Glu Phe Leu Ala Ser Gly Phe Glu Ser Gly Ser Glu Ser Glu Leu
                20                  25                  30

Glu Gly Ala Ala Glu Ala Ala Ala Glu Glu Arg Arg Ala Arg Gly Ala
            35                  40                  45

Ala Trp Asn Arg Glu Arg Arg Gly Ala Arg Thr Ser Pro Gly Pro Ala
        50                  55                  60

Gly Arg Pro Arg Lys Gly Arg Ala Ser Glu His Lys Asp Gln Leu Ser
65                  70                  75                  80

Arg Leu Lys Asp Arg Asp Pro Glu Phe Tyr Lys Phe Leu Gln Glu Asn
                85                  90                  95

Asp Arg Ser Leu Leu Asp Phe Ser Asp Ser Asp Ser Ser Ala Glu Glu
            100                 105                 110

Glu Glu Pro Phe His Ser Leu Pro Asp Thr Leu Glu Glu Ala Ser Glu
        115                 120                 125

Thr Glu Glu Asp Gly Gly Glu Asp Ser Asp Ala Leu Pro Arg Gly Leu
    130                 135                 140

Arg Ser Lys Lys Asn Glu Pro Val Pro Val Thr Leu Ala Met Val Glu
145                 150                 155                 160

Arg Trp Arg Gln Gly Ser Arg His His Leu Ser Pro Arg Leu Phe His
                165                 170                 175

Glu Val Val Gln Ala Phe Arg Ala Ala Val Ala Thr Thr Gln Gly Glu
            180                 185                 190

Gln Glu Ala Ala Glu Thr Cys Arg Phe Gln Val Ala Asp Ser Ala Val
        195                 200                 205

Phe Asn Ala Leu Val Thr Phe Cys Ile Arg Asp Leu Cys Gly Cys Leu
    210                 215                 220

Gln Lys Leu Leu Phe Gly Lys Thr Pro Lys Asp Ser Asn Arg Leu Leu
225                 230                 235                 240

Pro Ser Ser Ser Pro Leu Trp Gly Lys Leu Arg Val Asp Val Lys Thr
                245                 250                 255

Tyr Leu Ser Ala Val Val Gln Leu Val Ala Cys Leu Ala Glu Ala Thr
            260                 265                 270

Val Ser Ala Ala Val Leu Gln His Ile Ser Ser Leu Val Pro Tyr Phe
        275                 280                 285

Leu Thr Phe Pro Lys Gln Cys Arg Met Leu Leu Lys Arg Met Val Val
    290                 295                 300

Leu Trp Ser Thr Gly Glu Glu Ser Leu Arg Val Leu Ala Phe Leu Val
305                 310                 315                 320

-continued

```
Leu Ile Arg Val Cys Arg His Lys Lys Glu Ala Phe Leu Gly Pro Ile
            325                 330                 335

Leu Lys Gln Met Tyr Ile Met Tyr Val Arg Asn Cys Lys Phe Thr Ser
        340                 345                 350

Pro Ser Thr Leu Pro Leu Ile Ser Phe Met Gln Arg Thr Leu Thr Glu
    355                 360                 365

Met Leu Ala Leu Asp Pro Ser Val Ser Tyr Gln His Ala Phe Leu Tyr
370                 375                 380

Ile Arg Gln Leu Ala Val His Leu Arg Asn Ala Met Thr Thr Gly Lys
385                 390                 395                 400

Lys Glu Thr His Gln Ser Val Tyr Asn Trp Gln Tyr Val His Cys Leu
                405                 410                 415

Tyr Leu Trp Cys Arg Val Leu Ser Thr Leu Gly Ser Ser Glu Ile Leu
            420                 425                 430

Gln Pro Leu Leu Tyr Pro Leu Ser Gln Ile Ile Gly Cys Ile Lys
        435                 440                 445

Leu Leu Pro Thr Ala Arg Phe Tyr Pro Leu Arg Met His Cys Val Arg
    450                 455                 460

Ala Leu Thr Leu Leu Ser Gln Thr Ile Gly Thr Phe Ile Pro Val Leu
465                 470                 475                 480

Pro Phe Ile Leu Glu Ile Phe Gln Gln Val Asp Phe Asn Arg Arg Pro
                485                 490                 495

Gly Arg Met Ser Ser Lys Pro Ile Asn Phe Ser Val Ile Leu Lys Leu
            500                 505                 510

Ser Ser Thr Asn Leu Gln Glu Lys Ala Tyr Arg Asp Gly Leu Leu Glu
        515                 520                 525

Gln Leu Cys Asp Leu Thr Leu Glu Tyr Leu His Ser Gln Ala His Ser
    530                 535                 540

Ile Ala Phe Pro Glu Leu Val Leu Pro Thr Val Leu Gln Leu Lys Ser
545                 550                 555                 560

Phe Leu Arg Glu Cys Lys Val Ala Asn Tyr Cys Arg Gln Val Arg His
                565                 570                 575

Xaa Leu Glu Lys Val Gln Glu Asn Ala Gln His Ile Gln Ser Leu Arg
            580                 585                 590

Gln Ser Ala Thr Phe Ser Val Ser Asp Arg Thr Ala Val Asp Ala Trp
        595                 600                 605

Glu Lys Gln Val Xaa Glu Glu Gly Thr Pro Leu Thr Arg Tyr Tyr Gly
    610                 615                 620

His Trp Lys Lys Leu Arg Asp Arg Glu Ile Gln Leu Glu Ile Ser Gly
625                 630                 635                 640

Lys Glu Arg Leu Glu Asp Leu Asn Phe Pro Glu Ile Lys Arg Arg Lys
                645                 650                 655

Val Glu Asp Arg Lys Asp Glu Asp Arg Lys Glu Leu Lys Asp Leu Phe
            660                 665                 670

Glu Leu Asp Ser Ser Glu Gly Glu Asp Ser Thr Asp Phe Phe Glu Arg
        675                 680                 685

Gly Val Pro Arg Leu Pro Glu Ala His Gln Gly Leu Lys Glu Asp Gln
    690                 695                 700

Glu Glu Glu Asp Lys Glu Gly Asp Ser Asp Ser Glu Asp Gly Asp
705                 710                 715                 720

Thr Asp Thr Gly Val Asp Leu Ser Glu Leu Trp Gln Leu Ala Gln Gly
                725                 730                 735

Pro Gln Asp Glu Leu Glu Asp Leu Gln Leu Ser Glu Glu Asp
            740                 745                 750
```

<210> SEQ ID NO 5
<211> LENGTH: 15105
<212> TYPE: DNA
<213> ORGANISM: Homo sapiens

<400> SEQUENCE: 5

| | | | | | |
|---|---|---|---|---|---|
| ggcggcggaa | gtgcgcagcc | gcgcggcatt | ctggggccgg | aagtgggtg | cacgcttcgg | 60 |
| gttggtgtca | tggcagctgc | ggggagccgc | aagaggtaag | ccgcgggtcc | gagggccgat | 120 |
| ttggcctccc | ggtgggtgtc | tgtatccaag | ggggcttttc | ttgctcctct | caacggggct | 180 |
| tgggccaact | tggccttccg | gccactttga | cttcttcctt | aaccgcaggc | gcctggcgga | 240 |
| gctgacggtg | gacgagttcc | tagcttcggg | ctttgactcc | gagtccgaat | ccgagtccga | 300 |
| aaattctcca | caagcggaga | cacggaagc | acgcgaggct | gcccggagtc | cggataagcc | 360 |
| gggcgggagc | ccctcggcca | ggttagtggg | gacatgcgtg | agcagaacct | cttgctcgtc | 420 |
| ctgtcccacc | ccggttgggt | tgctgacctc | gcctggggtc | tcaggccaa | ggcctaagga | 480 |
| tcgccgacct | ctgcccccca | gtcctttcag | cttaacttac | tctttcatcc | gatgtttact | 540 |
| gagctcctgt | tccgtgccaa | actctgtcct | aggcaggag | cgtatgttgg | tgagttgtgc | 600 |
| aaaaatctct | tcccgatcta | ggagaactct | cacgttcttg | ggtgaaatca | ccgcctgcag | 660 |
| ttcggtagaa | gagagataag | tgctggggag | ggaaaggaag | gacagagggg | ctgaagagag | 720 |
| agttgcaggg | gagccgagtt | gctctgttag | aaggagcgga | ggctgtgctc | ggtggctcac | 780 |
| gcctgtaatg | ccagcacttt | gggaggccga | ggcgggcaga | ttacctgagg | tcaggaattc | 840 |
| gagaccagcc | tgaccaacac | ggaaaaatca | tgtctctact | aaaaatataa | aaattagccg | 900 |
| ggcgtggtgg | gcacctgtaa | tcccaactac | tcgggaggct | gaggcaggag | aatcgcttga | 960 |
| acttgggagg | cggaggttgc | agtgagccga | gatggcacca | ttgcattcca | gcctgggtga | 1020 |
| gagagtgaga | ctccatctca | aaagaaaaa | gaaagaaatc | aaaagataca | aaattagcc | 1080 |
| tggcgtggtg | acacacacct | gtcgtcccag | ctactcggga | ggctgaggca | ggagaatcgc | 1140 |
| ttgaacccgg | gaggcggagg | ttgcggtgag | tggagattgc | gccactgcac | tccagcctgg | 1200 |
| gcgacagagt | gagattccgc | tcaggagaa | aaaaaaaaa | aaaaaaaagc | ggaggtggtt | 1260 |
| gtttgagaag | atgacgtctg | aataaagacc | tcgaacaagg | aggccacaca | gacagtaggg | 1320 |
| gaaacgtgtc | ttaggatttc | aggcagcaga | aaacagcaaa | agccttgcag | tgggagcatt | 1380 |
| tggggagagt | acagaggtaa | acgtggctac | ggcaggagtg | aggggtgaa | taggggtaga | 1440 |
| tgagcccaga | agggtgatga | agagccaggt | gccgtagacc | gtcataagat | tgcctcgtaa | 1500 |
| aacagggagt | tacttctggg | tttgagcggt | ggagtgcctt | gtaggtgaca | agggtggaaa | 1560 |
| cagagagacc | tttaggttaa | ctgagaattg | aactatgtgg | tggtttgaga | ggaggcacga | 1620 |
| acggttttga | aggtgttgct | gatgagatct | gatgacaagt | tgcgtgctgg | gtattagaga | 1680 |
| cagagatttg | cctttagtct | gagcctctgg | aagggtgaag | ccaccatcag | gcaaaagtag | 1740 |
| cgcagggcac | aggcacagca | agtccaggga | agaccgcggc | tgggggcctg | tgtagcgcag | 1800 |
| ggcgcaggca | cagcaagtcc | agggaagacc | gcggctgggg | ggcctgtgta | gtgtgtttga | 1860 |
| gggtatgttg | tagaggttgt | tgggtaggag | acgtgagtct | gccaaaaacg | tacctcctgg | 1920 |
| caatcctgtc | ttgctagttg | gtaacccttg | tgaagggagt | agactgaccc | tgtaggccac | 1980 |
| tccccgcccc | ctctacttcc | acttcccact | ggggtcgctg | acttctgcct | cctcagccgg | 2040 |
| cgtaaaggcc | gtgcctctga | gcacaaagac | cagctctctc | ggctgaagga | cagagacccc | 2100 |
| gagttctaca | agttcctgca | ggagaatgac | cagagcctgc | taaacttcag | cgactcggac | 2160 |

-continued

```
agctctgagg aggaagaggg gccgttccac tccctgccag atgtgctgga ggtgagggcg    2220
tgggccaaac cagaaggggg gcacttgtct ctacactctc cttcagctca gcctttctgt    2280
gcaggaagcc agtgaggagg aggatggagc ggaggaagga gaagatgggg acagagtccc    2340
cagagggctg aaggggaaga agaattctgt tcctgtgacc gtcgccatgg ttgagagatg    2400
gaagcaggca gcaaaggtga gcagcagcca ggggcgggca gctgggtgcc caggcagaaa    2460
tctggccttg cctcacctga ggtgagcagc agcgaggggc gggcagctgg gtgcccaggc    2520
agagatctgg ccttgcctca cctgaggcgc ctgaggctgt gctggtggga ggggctgttc    2580
tccacgcagg ggacgcttgg agccttcttc agcgcaagtg acaacacgtt gctcctcctg    2640
cttgcttggt tgccccagga ctgtgtgttc acttttgggt agattccagg gctctgttg    2700 gcgcccact ccccaaagtc agtcccgctg tgggtgggac ggactgtgcc tttgttggtt     2760
ggtggagctg gggtccttct gagcctctca cagtgttttt ttccagggac aaggatacgg    2820
agagctccag ataccacctg gaggtggcca tagtccagga tctggaactc ccagtccttt    2880
tcctggggct cctgagccag actccctcct cttcccagag aattctagac tttgtttcca    2940
tttttgttat cagtatgggg ctctgtgcct cccccccaacc tctgccctat gtctgagggt    3000
gagggtgagg gtgcctttct ctggggctgc cgtttccact ctgccaagtg cagtctcagc    3060
tcccctgacg cccctggtac tcttgctcct tcagcaacgc ctcactccaa agctgttcca    3120
tgaagtggta caggcgttcc gagcagctgt ggccaccacc cgaggggacc aggaaagtgc    3180
tgaggccaac aaattccagg tcacggacag tgctggtgag cttgggggga gcctggcatc    3240
caggctgtct gttgcgttct ctgtcccgtg agtacatcca ggccttttcg ttgcagcatt    3300
caatgctctg gttaccttct gcatcagaga cctcattggc tgtctccaga agctgctgtt    3360
tggaaaggtg gcaaaggata gcagcaggta agaggggagg gggtgaaggg gggtagggtg    3420
gaaggtgggc cgggaccaca cacaggagaa gccagaggcc ttgtggctag dacagagaca    3480
tggcaacaga gccagcgtct tcttggggac cctgagaagg cagcggggca cgagggaccg    3540
ttgggagagg ctgggcactt gggggccagtt ggagcggccc caccttcttt ccttcctgaa    3600
aagggaagtt gtctgctcag agtctcagaa ggtgtggcgt gtgcagctgc ctttgctctc    3660
agattttccc aggttagggt tcttgctcta tttccctttg taagaacttg taagtcctgt    3720
ccatactcct tgatctctgc actatgactg gcctgtttcc tggagctgtg tgtgtctgta    3780
gacaggggcc tcatcaatgc tgagaacctg agggcctcaa cttcccctttt agagaaagat    3840 tgggcagaga aggccgtgga aggttttcag agaagagaga cgcacggcca agcatttggt    3900
agagcatgga gcacgttggg gttccggggc tgtgcagcca tgtgaccttg aggcagtgga    3960
ggcctagagt tggaactgcc ccaggacacc ttcaaaggaa gaaaggagac ccacaggaga    4020
ggtctcgccg acagcggctc aggagacagg ggcactgttg ctggtggtag tggtcggggc    4080
tggacggata gaacagagcc atgtccacat ggaggcagtg ctgtccgaag ggacaagga    4140 agctggcaga tggggtgga gggacaggca gcgattggga ggcagcacgc actgcagcct    4200
gagccaccag gtcagggacc cctgtcgagg cagcagctgt accggaggga gtcaggccgt    4260
ggggagcaga gctgcctcct gggtctgggt gggcagctgc aggtgcccag cagccagtgt    4320
cagcacaggt gtgaggaggg tcgaggacgg ggggcctttc tgggcccctg ccctttgtcc    4380
ttcccatgct tcagcagatt ttagtgagcg cctactgcgt gggctctggt aaatgttttg    4440
ttttgttttg ttttgtttgt ttggttttg gtttttttt ttccttacga gataggatct    4500
tgctctgtcg cccaggctgg aatgcagtga tcatagctca ctgcgacacg taccttctgg    4560
```

```
attcaagtga ttctctcacc ttagcctccc aagtaactgg gactccgcca ccaggcctgg    4620
ataatatttt gtatatttt gtagagacgg ggtctcactg tgttgttcag gctggtctca     4680
aactcctggg cttggagttt gatcctcctg ccttggcctc ccaaagtgca gtgagtactg    4740
gcatgagtct ccacacctgc cctctgattt tcttttcttt gtgcagcaaa tgtgggccaa    4800
aggaaaccag tctgcggcag ttggtggtgc ctgggcgacc ccagaggtgc tgagtaccag    4860
ctgctgggct tagggacctc gtgtggtctc acggtgggga tgtgatcaag ggacctaga    4920 aaaggtttat gtctgagagg gagttggagg ctgggacttc cggggactct tagggcggtg    4980
gccaaccctg gcagggcag acaggagttc aaggccactg aaggaggagc taatgcactt    5040
gagagggtcc tcctaagccc ctgtgtctgt ccagctgtaa ggggccctga gctttttga    5100 gtggagagac gggggtctc tgcagagtcg tagaggctat gctggccagg gcacgcgcca    5160
acatgctgag cagcctcgcg tccgagccgt ggggcctccc agccaggggt gggtggtctc    5220
tctgcaggat gctgcagccg tccagcagcc cgctctgggg gaagcttcgt gtggacatca    5280
aggcttacct gggctcggcc atacaggtgc tattctggtg gggagggcac ggggcctgg     5340 ctgtatctgg tggtcggtcc ttttttgtat cccagaatac atgggtttgg ggcttcactg    5400 tccctcctg ccccagctg gtgtcctgtc tgtcggagac gacggtgttg gcggccgtgc      5460
tgcggcacat cagcgtgctg gtgccctgct tcctgacctt ccccaagcag tgccgcatgc    5520
tgctcaaggt tcgtggccca gtcccctccc tgtgtctgtc atgggtcgg ggggccacac     5580 ggctacccc accacatccc actcctggcc agggcacagg tggtgcccac actccactgg    5640
ctccgcttgg ctagagaggc cacagaagca cctggccccc accccacct ggggtttctg     5700 tctcaggcag tccctgcctg cccgggcagc gcggctcagt ccgtgagcaa gccacggtg    5760 aggtatcttc ttcccggtgt gatctcacat acgtcggcgt gtctgacgtg gtaaactttt    5820
gtggtcctct tctcacaagg agcaacacac ctgttctgtt cacttctgta actgagcacc    5880
taactcacgg ctcccccgag gtgctttggg aagagctggt ggccatggga gcctttgcct    5940
ggctggggag ggctgtgctg gccctggggc atccctgctg aggaggctgg ggggccacca    6000
gtgacgtctg accttctgca gagaatggtg atcgtatgga gcactgggga agagtctctg    6060
cgggtgctgg cttcctggt cctcagcaga gtctgccggc acaagaagga cactttcctt     6120
ggccccgtcc tcaaggtagt ggtgggccct gcgtctgtgt ccctcagcat ctgcattgga    6180
aatctcggcc taagggcagg gcgggctgcc tttgtggttg gtgccctca ctggaccctc     6240 actgcagctc tgagcagacc tgggcccttg gatcacgaat gtctcacaga gcacctgggg    6300
gtggtgggca gggaagagag ccctcggcct tctcagggcc ccacctgacc ctgcttcaca    6360
cagcttcccc aggggagggc ctctctggct ggaggaggac actgggtgtt gggacctgag    6420
gccatggcca gggtacagtc ctactgcccg tccccaagcc atgggtggcc tgcatgtggg    6480
gaccctcagc ccccagaggg gcccagtgtg cagcaggagc ttctgcccca gcttctccca    6540
ggcctgaggc tggtgggcac ttggggtgg gggctgtgca aggggctacg gctcttcctc     6600
gaggcccagc tctgagggaa aggcccaggt gttcacaggg gccctggagt gggcggtgga    6660
ggtgcatggc cctgatccca ggtggctctg acccgggtct ctccgcagca aatgtacatc    6720
acgtatgtga ggaactgcaa gttcacctcg cctggtgccc tccccttcat cagtttcatg    6780
cagtggacct tgacggagct gctggccctg agccgggtg tggcctacca gcacgccttc    6840
ctctacatcc gccagctcgc catacacctg cgcaacgcca tgaccactcg caagaaggtg    6900
tgtggtgggg cccttccagg ctcatgctgg gcatggggtg gggcagccca ggtgcccgac    6960
```

```
ccaaggcagg gcctggggcc tccccgaagc ccctgtctgg agacagccca gcaccctggt  7020
gcagtcggtc cttgcaggtg ggggaagggt ggatgggttg agaccccgtg tgcaagatga  7080
ggaaatgatt cctgtgccgg cccaggagga acgtgcatca gcctgacttg tcagcctggc  7140
cagtagctga cgtggttctc tctgaccagg aaacatacca gtctgtgtac aactggcagt  7200
atgtgcactg cctcttcctg tggtgccggg tcctgagcac tgcgggcccc agcgaagccc  7260
tccagccctt ggtctacccc cttgcccaag tcatcattgg ctgtatcaag tgagttgtgg  7320
ggtgggcagg gttgtgcggg agggtcagga aagcaaatt tgctgggact gtgtgggcgg  7380
tgcctctggc gttcagggcc ttggggcctg agtctgtgtc ctggccgtcc ctgaggaagg  7440
gctggggtcc ctgtacctgc tacggggaga tgctctggat tctggagagc tagggctggt  7500
gggcacctgt gacatgagct cctccaacag cggtttagcc gcctcgggtg ccacccagcg  7560
tgtgttctgg gggcttgtgt gcagtttgca gtgagtttgg ttcattacgt ggggttcttg  7620
ggtggagcac atctgatgca gtgaactgca ttttgggtgt gagcgcttag gagggtccag  7680
gcacggtagg ggctgcagca ggaaaaggtg ggagcagtac tgtggcctct ttggccagga  7740
gggggcatct gtctggctga gccttagaaa ctcaaggctg ggaagggagg tgggaagtcc  7800
aagggaagaa gtaggaaagg cgggaacagg gaggagagca ggcaggaaca gatgaccct  7860 gccaccgtgt tgaaataaag ctgaaagctg ggtaaggtac ctgcagcccc atagctgggc  7920
aaggggtgca ggtccctgcg gttcagacgt gccttgtcct gctttagggg tctgatgtcg  7980
gtgagtgggg gaggaggtcc aagacagcag ggggagggc agggctgcc agagccgggg  8040 cctctgctca ctcggccttc ccacccccag gctcatcccc actgcccgct tctacccgct  8100
gcgaatgcac tgcatccgtg ccctgacgct gctctcgggg agctcggggg ccttcatccc  8160
ggtgctgcct ttcatcctgg aggtgagtga ggctgtggtg ggcgtgtggc acctctgcct  8220
gctcctgtag ggagcatctg ctgctccggg cgtctgtgct gagttgtccg gcgacttccc  8280
ggagccctgg ccgcctcctt gtcacgggtg tcacgaggac agtgctcctc cgtgtgctgg  8340
gggcagtgtt ggggaacgtg ggaccactgg ggatgaaggc ggctgctgct agggctgtgc  8400
ttgaggatgc cgggacctga ccctgtaggt gcttgcccaa gactggagta ggcaggaggc  8460
gagatgggcc aaaacccaag tctgattgct gaactgtaca ctgaacagtg ccctgccctg  8520
acagttgtgt gcatgtgtat gcatttgtat ggaggatgtg tgtacatctg ggtgggtgcg  8580
tttgtctgtg catgcatgcg tgtgtgtgca ccatctgggt gcatgggtct gtaaatctgt  8640
gtgtgtgtgc atatcagttc atgtgtgcat ctgtatgtgt gtatgcacgt gtatccatga  8700
atgcctgtgt gcctgcaggt gtgtgcatct gtgcgtgtgt acacctgtgt gtatgcatgt  8760
gtgtaccttt gcgtgtacct ttgcgtgtgt gcacctgtgc atgtgtcttt gtataccagt  8820
gtgtacctgt gtgtacctgt atgcatgcac atgcgtgtgt acctgtgtgc acctgtctgc  8880
atgtgtgtac ctgtgcgtgt gtgcacctgt gtgcatgcat ttgcgtctgc atgtgtctac  8940
ctgtgcatgc atgaaccttt gcatgtgtgc atctgtgtgc atgcatgtga tgtgtgtctg  9000
cgtgcatcta tgtacctgtg tgcacctatg tgcatacaca cgtgtctgtg tgcacttgtg  9060
tgcatgcatt tgcatctgca tgtgtgtact gtgcgtgtgt acctgtgcgt gtacctgtac  9120
acttgggtgc atgcatgcac gtctgcttgt gtgtgcctgt gcgtgtgtgc acctgtgtgc  9180
atgtacgtgt gtctacgtgt gtgcctgtgc atgtgtgcgc ctgtgtgtac ctgtgtgtat  9240
gcatctttgc acgtgcacat gccactcagg tagggaaaga ttggagtccg aagttttcaac  9300 tttcagtggg tgggttaggc cccaccccgc tgtaaattta ggaattcacg atctccaccc  9360
```

```
tgtttatcta atgagttctc agcctcatga aggcccagag tcgtgtcaca gctgtccttg   9420
gggctgggtc ccaggttgct gggtccagaa ggtatggaag ccccaggcac gttctgattc   9480
cccttccact gaggcaggga tgctgaacat ctttaggaag ccatgttcac tcccatggca   9540
gccagcagtg gtctctgatt gcccagccct tggcctggcc cctgtgtctg tgggcctcca   9600
gctctgctgc ccagctccag gcatgctttg tgtctgtttc ccttgtccaa tctccttggc   9660
tacgtgcttt cttactctct tgcagtgtct gtttcttcac ttgtgcactg ccctggttca   9720
ctgcagccgc accctgtagg cccctctcac gcagggatgc aggcctctcc tctccggaaa   9780
aagcaaaccc taaaagctaa acaaagccct cagctgtag gccgtgcctg cccttccccg   9840
gtgcctggac aggaagccag tcgcctgccc atacttttgg cccaggctag agaagggcag   9900
tgtcctccca gaggttcatc agtaccaggg cgttttccca tctggacctg agctcagctg   9960
tctggcagcc acccctgctg agtggggtgt cttgctgggg cctccaccct tgggccccc  10020 ataatctgct tctgtcctct ggtgcccag catgtaccct ggatctctct ggttcacagc  10080
ctgagggctc ctagtggttg gggagggtc acaagactga gaggccaggc tgactctttc  10140
tctgctcctc ctggcatgtc ctacggaggt gcatggcctg tggcttctgt ggagggtgtg  10200
ggaggggccc cccaggcctc ccgtgacctc catctgtccc gtcctgtgtc tggcactctt  10260
tgctgttgct gctgcgtctt ctggttgctc gggacggagc cccatgtggc attgctgtgc  10320
tgagggccag gatgggcctc agtgccatgt tgtcaggaat gggggctgtc ctggtactct  10380
gtgtggcagg gacctctagg tctccagacg tgggtcctta gtgcttccca ggatttgggg  10440
agagggcccg tgttcctgat ccttccctgc tgatcagagc cccactcggg gacacgccag  10500
gctgtgtggg gccatggggc tgggaccgtg cctagctgct tatctcttgt ttcgggttgg  10560
gtctcctcgt gctgaagcct gaggaccagg gtgaccaggg tgcagccagg tgcagggcca  10620
aagggaccag ggggaccagg gtgcagccag ggtgaagcca gggtgaccag gcatgggcc  10680 gagagagcct gacactggcc cttggggcag atgttccagc aggtcgactt caacaggaag  10740
ccagggcgca tgagctccaa gcccatcaac ttctccgtga tcctgaagct gtccaatgtc  10800
aacctgcagg agaaggcgta ccgggtgagg ctggctcctg ggagggcct gggcagttcc  10860 cagggtgggg ttgggggtgc tgaggtggat gggaggggc tggcatcctc caagttcaag  10920
catggacctt catggtctcc cagggctggg gcatggagcc ccttccttgc agtccgtgcc  10980
ctggagatgg cgctgccctg acagcctgag gggaaggggc ctgagtgcag ccccagcctc  11040
tccctgatgc actcggccct ctctcctgct cttcaggacg gcctggtgga gcagctgtac  11100
gacctcaccc tggagtacct gcacagccag gcacactgca tcggcttccc ggagctggtg  11160
ctgcctgtgg tcctgcaggt gtgtgtcctg cccacaccgg ctcgtggccg actcagactg  11220
tcttataacg ggcttggctg ccccaggctg gtaggaggtg cccttgtccc gggtacctgg  11280
gactggggtg gaacctgact gctggcaacg cgccccgtga ggcccccttg gaggggctga  11340 tgagggttc taagccattc aggaggtttg ggggcaggcc tggcagtgg gctgaggacc  11400 ctgggagcac aacagcctcc tccccaggtg ggaaccacaa ggctgatctt tgcttcgggg  11460
ttgggactga gcatgccgac cctggctcag gctggtacgc tgatcgcaca cttccccagg  11520
ccatcccggg tgtggggagt gggtggagtg gcttctcagg tggcaggaag gcctggcctg  11580
ccccgccaaa tacccacat cagcctcata ggaaggccca gcctgccccg ctaaataccc  11640
cacgtcagcc tcatcttagg caggagtggg gtggaggagg gggttctcct tatcctcaga  11700
aggtccttct gggcccccac gggaggtctg tttgctctca gccgtgatgt ttccagcctc  11760
```

```
agggagcgct gtgctagtgg aaggggtggg ggcctgctgt ctggccctgg tgctggaatc   11820
agatgtgccg actataggtc tgtgcagtgt ggggaggagg gatctgctca catgagccac   11880
aattggtcag aggcttatcc agatagaggt gtgtgcatgt gtgtgtactc acacacggcc   11940
acacatgtca catgcacaga gccgggaccc cctttctggg gcactcacag catgggccac   12000
agcctctgtt cctgcccatg tcctacttgg gtggtgatac ctggcattgg ggcatctctg   12060
cttctggact caagggccca gggtcgggtt ctggggtagg ggtcagaaaa tgttttggt    12120 gaggggccaa atggtaaacg tggctttcta cggatgttca gctgcacagg caactgcaga   12180
accatgcaat gcacacgtgt ggctgcacgt cagcgagact gtattttatt agtagtagta   12240
gtattgtttg agatggagtc tcgctgtgtt gcccaggctg gagtgcaatg gtgcgatctc   12300
ggctcactgc aatctccatc tcctgggctc aagcgattct ccagcctcag cctcccaagg   12360
agctgggttt acaggcgccc accaccacac ccagctaatt ttggtatttt agtagagacg   12420
gggttttgcc acgttggcca ggctggtctt gaactcctga cctcaggtga tccacccgcc   12480
tcagcctccc aaagtgctgg gattacaggc gagagccacc acgcctggca taaaacttta   12540
tttccagagg tgagtagtgg gcagggttgg cccagagggt gggctgattc tgcctctgcc   12600
atcccagctg caacagctat gcacttgagc cctgagatgg gatccatgtc ccctcctggg   12660
gtatccccgt ggccaccacg cgtggttttg cacaggacct gggccagctg tgcacatgga   12720
gcggtcctgg gcttcagtgg ctgacccctc ccttccgcag ctgaagtcgt tcctccggga   12780
gtgcaaggtg gccaactact gccggcaggt gcagcagctg cttgggaagg ttcaggagaa   12840
ctcggcatac atctgcagcc gccgccagag ggtttccttc ggcgtctctg agcagcaggc   12900
agtggttagt gggccctggg ggtagtgcca cctgagggca cctgccaggg tatagcccca   12960
gctacatgtg ggggtttgcc cagggtgagg catgacccctg aactcccca accccccagg   13020 aagcctggga gaagctgacc cgggaagagg ggacacccct gaccttgtac tacagccact   13080
ggcgcaagct gcgtgaccgg gagatccagc tggagatcag tggcaaagag cgggtgcggc   13140
tcggcgaggg gacctggggg tgtgttgtga cttcctgggt ttcagatcta gcgcactatg   13200
acttgagacc agggcgaggg tttggaaaca gtgccaggcg gccagggccg tgcccggatg   13260
attcgacttg gagaggggt aggtgttgga gaactggcca gaaccaggcg tttccaggga   13320
ggggaagccc caggctgcac taggttgggg aggccatgcc ccctcaggcc tgatgggctg   13380
gaggctccgg gcaggtggag tggctggact gacctcgtca cccaggccag tatgtgggca   13440
ccaggggccc gtgaggagaa gcaggaaggg ctctgccttt gaccttggac atgggatgga   13500
caacttggag gatggctttg tgatttggga acagagggga ctagaaattg gccacatggg   13560
gccctggtgg tgggtctggc gatgcctggc cctgctgtgg ccgccagccc ctgccctctc   13620
tcacctgagc ccctggttct ttggccttcc agctggaaga cctgaacttc cctgagatca   13680
aacgaaggaa gatggctgac aggaaggatg aggacaggaa gcaatttaaa gacctctttg   13740
acctgaacag ctctgaagag gacgacaccg agggattctc ggagagaggt ggggcctgcg   13800
tggtgctccc aggggaaggg tgggcctgga gggctctgct ggacttccca gagccacgag   13860
ggccacctgt acccatcctg caggggctc accagtctct ggcccagctg ggccaacct    13920 cagtgttgcc aggcttctgg tgccagcgcc ttccctcctt gaagtgaagg cctactggga   13980
ttggtaactc tgtccccagg cctgtgacct cccagttcct ccccagggct cctctccacc   14040
tgctggaagt cagcgagggg aagggtgttg ggagcctggc caccctcctg cccccactgt   14100
gactttgctg gtgaccctg tgggtgggag tcatatggac tctgcttctt gttcctcagg    14160
```

```
gatactgagg cccctgagca ctcggcatgg ggtggaagac gatgaagagg acgaggagga    14220
gggcgaggag gacagcagca actcggaggg tgaatggtct tggggtgaga gggtgtggcc    14280
ctgtgagccc atctggcggg agggcagagc cacgtgggcg gggggcgtgg ggctctgggc    14340
caggcttttc cctccctggg aaggccaggc caaatgctct gttctctggc agccagcaac    14400
agggataaat taattagtgc cgtgattaat tagtgatgag taacctctaa ggctggcttc    14460
ttcctgataa agcaaaattt atgtagcctc catctctccc cgcagatgga gacccagacg    14520
cagaggcggg gctggcccct ggggagctgc agcagctggc ccaggggccg gaggacgagc    14580
tggaggatct gcagctctca gaggacgact gaggcagccc atctgggggg cctgtagggg    14640
ctgccgggct ggtggccagt gtttccacct ccctggcagt caggcctaga ggctggcgtc    14700
tgtgcagttg ggggaggcag tagacacggg acaggcttta ttatttattt ttcagcatga    14760
aagaccaaac gtatcgagag ctgggctggg ctgggctggt gtggctgctg aagccccaca    14820
actgtgggct gctgaagtca actccgcggg ggaaacttac ccttgacgtc agcagaccga    14880
gaccagttcc cagttccagg ggaaggcttc aaggcccctg gcccttccac ccacctttgc    14940
cctcagtatg cagacctcgt ccatttgcac caggttctgc cttcactcca ccaagtcttt    15000
gaaatttgtt tcctttcctt tgaagtcaca ttttctttta aaattttttg ttttgcatcc    15060
gaaaccgaaa gaaataaagc ggggggaggc agggccattg tgttg                    15105
```

<210> SEQ ID NO 6
<211> LENGTH: 23806
<212> TYPE: DNA
<213> ORGANISM: Mus musculus
<220> FEATURE:
<221> NAME/KEY: modified_base
<222> LOCATION: (4293)..(4312)
<223> OTHER INFORMATION: a, c, g, t, unknown or other
<220> FEATURE:
<221> NAME/KEY: modified_base
<222> LOCATION: (6219)..(7065)
<223> OTHER INFORMATION: a, c, g, t, unknown or other

<400> SEQUENCE: 6

```
aacatgcagg atgccgccac ccacttgttg gtcctcgggt tgtacttctc tatggagttg      60
aggctggagc tgccgtcatt gccccccacg gcgtagagcc agccgtccat ggccaccagg     120
tcatgtgtgc tcctggggag ttggataggc aagagtaagc ccaaggggca agccaagaga     180
caggccaaat gagtggggca cagagggagt aaccataggg acaggcaacg aaaggagcc     240 ccctatgccc ggggggaacc caaggacctg ccgtactgtt gaggtgctgt gtgcacaacc     300
cctgggctta cactcctgga ataaaccaga tgtagtggca gaaccactca ccacccgccc     360
ctggccttat acacctgcgg atattcatgg gtgccacact ctcccaggca ccagccttgg     420
tgctatatct ctccactgag ttgaggcagc ttgtgccatc attgccccct gcgacataca     480
gggcaccctc cagcactgct actcctgctg agctgcgccg gctcagcatg gaagctacag     540
gtgtccatga attcacctgt agagacaata ggacaggctg gaggcagacc caccaagggc     600
cccccaaccc tgccaccaca tagactctac tcttggttgg gtatctgagg gtcaggggtg     660
ggatatagaa agcagacccc ttgggtggca cagatggcca gaatctggga ttatgcccca     720 tccccccag cactttagag gaggacattg tgatggggtg cgctatgcac ctggggctca     780
tacttctcca cggtggccag gtgtgacgag ctgtcataac cacccacggc gtacaggttc     840
ccatctgtgg gaaggcaata tacccacgaa gctcctgcag ggtgtaggag ttttggggggt     900 gggtgggaag gggagaggca ggaaagcggg taccacggga agcctgtcac ccaccaagtg     960
```

```
tggccacacg cacatatcgc ctccgggtgc tcatggcagc aatggatgtc catgttcccg    1020
tcagtgggtc atatcgttca gcactgtgga caccagaatg atgccgacgt tcagttacaa    1080
cagttaagtc atccttgccc aggctctgtc ccctcactcc ccccaaagct acggctgaaa    1140
tcccgggcat cacagactct atgaatagag agcaaggtgt gctgggcgga tactggctgc    1200
tggctgcttg gactgagggg agggcccctc caggaggaga atggtgccaa ggccctgcgg    1260
atgctgtgcc ctgaggtaag gaagccttga ggacccagta gcctggatta ggccctcatt    1320
ctcttagcca gatgtgactt catagttaag ccagccttag ctgctgctgc tgagccgacc    1380
ctgcaaagcc actggggccc taacccaaac tactacctgt tgaggcagga agccccatcg    1440
tagccaccag ctgcatacag gagcccatgc agagcagcta cacctaggca gctccgcctt    1500
gtgcccatgg agacctcggg ctgccatgtg tttgtcacag ggtcatagga ctccaccgta    1560
gccaggtctg aggttccatc gtagctagga gaagagtccg ctactgacca aggatggccc    1620
ggcaggcttg tgacaaacct ttcagcctac atggccagct tctatgctta cccgcccaca    1680
gcatacagtc ggttcccgac ggcagcaact cctacacgag cccgacgtgt agacatggag    1740
gccaccacat gccaacggtc agtccgcgtg tcatacgctt cacagtctcc gtggatcgcg    1800
aacaggctcc caccacctag agatgggtaa ctataaataa aggggctcaa ggctgggcag    1860
aggactctag tgtgacccaa gtacaaagac atgaaggctc caggggtggg aagagataga    1920
gactgggaca cactagtggg ccccatccta tagggtctct gagacacaca ggtctaagta    1980
taatgggttg ggtttatagt ctgagttggg gtggatggcc tagggcaaaa tgggaaggag    2040
aaggggttta gcataccgac agcaaagagc acagggccag cgccctcaca tcgacggggt    2100
ctcgtgcggc tggttcccag aacacctctc tgctcaggca gcaggtggaa cttaagggcc    2160
tcgatgagca gatccttgca gtcagggtga tgcctcacaa ggctttcggc atccacgtgg    2220
cccaggagga agtctcggct cagcagaggc agccgtacac acttcatcaa ctagggcagg    2280
aagcgccatg taaggcaaaa ccctgggcgt acttggccca gggctaagac ccactcaggt    2340
gcctatagca cctgtgagat tgggtcttga gacaggtggc tcaaccactc caaaggagtc    2400
cctggatgga agatgctaag gacttgaaga agtaagctta taccgcagcc acctgcattc    2460
ccttctgaca gcacgggagc tccaggacct ggcctcaccc ttggtacatg ctgcctccga    2520
gtgtctacgt catgtttgac ccagctcagg actgcacggt acacatcttc ctctgagggc    2580
acgttcaggc tatcactaga gaccaattcc agcacctggg ggcgagaggt cctcagacct    2640
gacatctggg taggggaggg cccagagaac cctgaacgtg tctgagagta tcagacagag    2700
ggcatgtgcg tgtccatgca caaacacgca cacttaacgt tcttagagtg aagaaccaag    2760
cagagtcaag attcacagat tttgttccca gtagaggggt gaggggtgtc caaggtccta    2820
agtagtctcg ggtacataga atcagagact gggaaatcat ggccctagaa tgcggtaaag    2880
acaggcatct aagacaaatg attgggtgac atgaagaagat ggaaacaggg ttgggaggag    2940
atggccaggg aatgaatcat agggtgaaac tcgcaccaga aacttgaaat gaggattgca    3000
gaacactggc tgcaagggtc tgggcttggg caatacatgg tggggctggg gcccaaactg    3060
gcatgttacc tgcttcagtg gttacctgct tcagtggcaa cagcatgaac tcctcagtct    3120
tggccacatc cacgaagtgc tgcagcacgt acctgtgtgc tgccttgagc aggtcactgc    3180
atgagtgtgt gtctgcaaat cctcgaatgc ccaggcagtt ggaagggtcc agctggctca    3240
ggaggaactt gcagcaggca tctcgaacac cattcaactg tagaaggctg gcagctggga    3300
gcagagtctg gggcatgaag atgggtgagg caggagggtt ccagaagagc acagagtgac    3360
```

```
tggatattgg ggagaggcat gggggggggg cagggcacac agatctgggc tggagatctc    3420
aggggacgtg ggtatgggaa tggtaggcct cacctgaacg ttgccctcgc ccaccacgat    3480
ctcagctgtg tatgcaaact gcaccagctg gtctaaggct tgcgggtcaa tgtcatgcag    3540
tgtcacatgt gtctggcggc tctcactcat ctcatctgtg aaaacagtgg attaggcggc    3600
ctacccgggg agatctgcgg agattccccc tagggctgcc cagactgttg tatgtggtac    3660
ttgcttgtga acatggcgtg gaagtagggg ctacaggagg ccaacaccac cttatgagcc    3720
cggatctcct tggcagccac atgcaggacg atgtcgcaca ggaggccacg ctgccgcatg    3780
cggctcatag ccacaaaagc atcatggtag tgccgctttg agttgtgtgc cacactgtga    3840
ccctctctgc tcaacagctg catcgcacct tccatcgggg ctgcaggccg ggcctgccgg    3900
ggccgagctc gctctgcctc ggggctgcag gccgcaggac taggtcaggg tttgtacccct   3960 gtagagggcc actcacccgc ctttgagaac tcccagcaca gccaaggcag ctgcggtcta    4020
tgcccaggag ttcgttcagt catcaggcac caaagcccat ggaggaccag cctgtcactc    4080
actgccactt tccagggctc tagatctctc tccggtccag gaacctcgct ggagccggag    4140
cagattcttt cataaatgta agcctgctct acctgtcccc cttcctctgc tgactacctc    4200
tcctggggct ccgagcccct catctagtgc ccaggccact catggggagg aagttggcaa    4260
acgttgtcct ctgaatcccc agatcccagt cannnnnnnn nnnnnnnnnn nnccccgccct   4320 cccgcccgcc ctcccactca cgccggcggc tggggcggcg gtggcgcctc aggcccgggc    4380
cccgggctgc tgtgctcggg actctgcgtc ctgcccgccg gccgctcgcc acggggctgc    4440
ataactccag ccgccaaagc cgcgaccctg atggacggat tgggacgcgg gtgcccgccc    4500
ggccgctcgc tccactcggg cgctcgcccg tcgccgcaga ccctgtttct cggcgccgcc    4560
cgccctgccg cacgcaaggt tgcaggagcc gctgccaccc gcgtccccgc tctcctccca    4620
ggagcgcctt ccttcgtgtg cgcgcctaggt tagcttcaca tcccagcgcc ccggttctca    4680
cctgctagag cttgctgtga ctgacaaagc tccatagcac gggggtagag cgggacactt    4740
gcaagtgtgt gtccccccccc ttaccctcag gcctcctgtg cacaagcgcg tgcaaaggtt    4800
cagcgcccct atacatgcat atttgagcat gaggcggacg ggggctgcta gcgtctgaga    4860
ggtgcaatta tctattgaca tggacgcagc attcttgtca cacccaggct cgccaaggaa    4920
ttgggtgtcc tttgacttaa aaaaaaaaat atatatatat gtttatatat atatattata    4980
tatatatata cccgtacaca taatatatat atatatatat atacatacac acatatatat    5040
atatatatat ttttttttatg tgtacgggtg ttttgcctac ttgtgtacta tataaattac    5100
gtgtgtgcag tgcctacgga aaccagaaga gagcatcaga cctcctggga caacattggt    5160
gatccacttc gtagaccctg ggaattggac cccagtcctc tggaagagca gcttagtgct    5220
tttaagtccc ggccatctct atgcagccct tgcttgctcg gtcggtcggt ctgctgcctg    5280
cctacaattt atcatctatc aatccatcca tctatccctt tatctgcttt tttcctggaa    5340
tttgctctgt atggactgat ctcagagaca gcacagagcg agctcgcttg tctctgagcg    5400
cggagataaa aggcgtgcgg tcgggacagc cctttacttt ttaaaaaaaa aaagatatt    5460 tttcccccctc caccctccgg gcgtggtagg caggctgttc agatttccag ccttgtttcc    5520
cgggtgcgag cggtcgttcc aggcggggct ttgagctgtg agagcctgag ccgagctcgc    5580
cgccctcccg cccggggacc gcggccgcgg cggctcgaga acccgaaagc cagcagcagg    5640
ggtggcatgg gcggggctcg cgggaggaag tcggagggcg caaggcattc gtgggcccgg    5700
aagtgcggcg cacgcggctg ggcgcgccat ggctgcgtct cgcgctcccc gcaggtgagt    5760
```

```
ggcctgggcg ggcgcgcgga cccgggcggg cgcctggtcg cggggtccgt tccgatcctg    5820
acgcggtgtc actggcaggc gcctggagga cctcagtgtg gacgagttcc tggcttccgg    5880
cttcgagtcc ggatccgagt cggagctgga gggcgccgcg gaggcggcgg cggaggagcg    5940
cagggcgcga ggagccgcgt ggaaccggga gcggcggggc gcgcgcacct ccccgggccc    6000
cgcaggacgg tacgcggggc tccagaaagt cttttttgcaa aacgggcagc tgtcgtgggc   6060
tggagcagcg ggttgagctt aaggaacaca cgacgggggc ctcgggtcc gagcgatggg    6120 aagggttgca aggttggaaa tgaggagag cttggagggg gaagcgcacg cgtggttggg     6180 aggggaagc gcacgcgtgg ttgggagggg gaagcgcann nnnnnnnnn nnnnnnnnnn      6240 nnnnnnnnnn nnnnnnnnnn nnnnnnnnnn nnnnnnnnnn nnnnnnnnnn nnnnnnnnnn    6300
nnnnnnnnnn nnnnnnnnnn nnnnnnnnnn nnnnnnnnnn nnnnnnnnnn nnnnnnnnnn    6360
nnnnnnnnnn nnnnnnnnnn nnnnnnnnnn nnnnnnnnnn nnnnnnnnnn nnnnnnnnnn    6420
nnnnnnnnnn nnnnnnnnnn nnnnnnnnnn nnnnnnnnnn nnnnnnnnnn nnnnnnnnnn    6480
nnnnnnnnnn nnnnnnnnnn nnnnnnnnnn nnnnnnnnnn nnnnnnnnnn nnnnnnnnnn    6540
nnnnnnnnnn nnnnnnnnnn nnnnnnnnnn nnnnnnnnnn nnnnnnnnnn nnnnnnnnnn    6600
nnnnnnnnnn nnnnnnnnnn nnnnnnnnnn nnnnnnnnnn nnnnnnnnnn nnnnnnnnnn    6660
nnnnnnnnnn nnnnnnnnnn nnnnnnnnnn nnnnnnnnnn nnnnnnnnnn nnnnnnnnnn    6720
nnnnnnnnnn nnnnnnnnnn nnnnnnnnnn nnnnnnnnnn nnnnnnnnnn nnnnnnnnnn    6780
nnnnnnnnnn nnnnnnnnnn nnnnnnnnnn nnnnnnnnnn nnnnnnnnnn nnnnnnnnnn    6840
nnnnnnnnnn nnnnnnnnnn nnnnnnnnnn nnnnnnnnnn nnnnnnnnnn nnnnnnnnnn    6900
nnnnnnnnnn nnnnnnnnnn nnnnnnnnnn nnnnnnnnnn nnnnnnnnnn nnnnnnnnnn    6960
nnnnnnnnnn nnnnnnnnnn nnnnnnnnnn nnnnnnnnnn nnnnnnnnnn nnnnnnnnnn    7020
nnnnnnnnnn nnnnnnnnnn nnnnnnnnnn nnnnnnnnnn nnnnnagggg gaagcgcacg    7080 cgtggtttggg aggggaagc gcacgcgtgg cttggagggg gaagtgcacg cgtggtttggg   7140 aggggaagc gcacgcgtgg ttgggagggg gaagtccacg cgtggtttggg aggggaagc     7200 gcacgcgtgg ttgggagggg gaagcgcacg cgtggcttgg aggggaagt ccacgcgtgg     7260 ttgggagggg gaagcgcacg cgtggcttgg aggggaagt gcacgcgtgg tttggaggtg     7320
ctgttggagg agagctgagg acggtctgtt ttacagcaat gaggcgagca tggtgggtgg    7380
ggtcacagct gctctgggc cgggaggcg ctcagcgggt gctgagtttg agatggttgt      7440
gttggaacaa tgtcagaggt gctgtgcgtg tgacgatgga ggagaggcaa gcccgatggt    7500
catcgatccc acagtgaagg gaataaacta acatggcctc acggaggcga caaccagatt    7560
ggctgtgtag ggtcgaaaaa ctccgtcccc cgacccgaca cccgtttttct cagcccgcgt   7620 aagggccgcg cctctgagca caaagaccag ctctctcggc tgaaggacag agaccccgag    7680
ttctacaagt tcctgcagga gaatgaccgg agcctactgg acttcagtga ctcggacagc    7740 tctgcgaag aagaagagcc attccactcc ctgccagaca cgctggaggt gaaacccggc     7800
agacctgggc gtgggggcac ctgtggttc tatacaccgt cccagccttg tccttctgta     7860
tctggtccag gaagctagcg aaacagagga agacggagga gaggacagtg acgcgttgcc    7920
cagagggctg aggagcaaga agaatgagcc tgtacccgtg accctcgcca tggtggaaag    7980
gtggaggcag ggctccaggg taagaagcag tataagctgg gtggctgcat ctccacaggc    8040
gggagactct ggcctcgcct cgtttgaggc gtctgagaca gcaggtgaaa agactgtgtt    8100
tctgggaagc gcacaatgga ggtctttcca agtgccaggg tcctccagct acgtctcctt    8160
```

```
atttgtagtg catagtcctg cctgcttcct cacactctct atcagggttc tgacccttgt   8220
ggggtggttg tagagtttgt ttcatttctg ttaacaggat accacagacg gggcaatttg   8280
tttttttgttg ttgacttact cacctgcata taggttggtg taccgtatgc aagttcatag  8340
ttaaccgatg gttgtgagcc actgtgtggg tgctgggagt caaacctgga tcgtctggaa   8400
gaacagtcag tactcttaac taccaagcca tcttccagc tccagactag ttaatttgga    8460
aagaaattta actggctcac attgctggag gtaggcaggt caaaaagtac ggtgatgtct   8520
ttgttaaagg ccttgtgttg tgatccttgt tcagttacat cttttgaatt gttagaaatc   8580
aagcccagga cttgtacatt gtaggtaatc acactgtcct gagccctgag ccttttcgtt   8640
tggtttagtt tggtttggtt tttgagacag ggtttctctg tgcagccctg gctgtcctgg   8700
aactcactct gtagaccagg ctggcctcga actcagaaat ctgcctgcct ctgccttcca   8760
agtgctggga ttaaaggcat gtgccaccac tgcccggatg tttcatgtga tcttcattac   8820
tttccaaagg ctttatttcc aaataccacc aaataaactt ggatattaaa tttctactac   8880
ataagccttt gggctatagt caggcttagc attatttctt cactggggag tgggaaatga   8940
agtcagtgtc ctttgaataa tttcacactt aacttagagg ttttgggatt tttttttttt   9000
tttttttaca gttggagatc actatgtaaa tcaccctggt ggctaacttt gaactctatg   9060
tagagtagtt tggcctcaaa acttgctgta gtctccttgc ctttgctttc ccagtgctgg   9120
cgtagccatc agctatcatg cttggctttc actttggttt ctttagggaa gggagtgaaa   9180
agggagattc ccatacactt tctggagcaa gtttgtaatg cagtattctc tcccctttct   9240
tctgggactc ttgacacagg ctctgcctgt ccaggtgtgc gcaataccta ttttgttgtt   9300
ggctcatggt ccagtgatct tagccccaca gttgctctgg ccctgagatt gtgggttaga   9360
ttagcacctt ttcaacttgg agcaggttcc tagagccagg tactgtgaac tactctttta   9420
gtgatcttga tctcttgccc cttcagcacc accttagtcc caggctgttc catgaagttg   9480
tacaggcgtt ccgagcagct gtagccacca cccaaggaga gcaggaagct gctgagactt   9540
gcaggttcca ggttgcagat agtgctggtg agctggggac tggggacctg tgccaggctt   9600
cagtgtgaca cctgtgtgcc ctatataggt gaatgacact ttggttcctt gcagtgttca   9660
atgctctggt tactttctgc attcgagacc tctgtggttg ccttcagaag ctgctgtttg   9720
gaaagacacc aaaggatagc aataggtaag gtatggtcag gggttttgtc attaaggtag   9780
aggaggtcac aaagtcttaa ggaagcacag aaagcagcta ataaatacag atgagtcatg   9840
gtggggctgg gagtagacat agccatgtgt cttgagatag cagatgcaga agagcaaccc   9900
taaccctaac ctgaaggaga agatggtggc agttggttga tgcactgaca ggatgagtac   9960
atctagaggc agcagagagt gaggagagca agaaaaccca acaggtggag agggcagaaa  10020
ataagccagg tgatatgaca gaagcctaag tgaatggcta acacacccag aatctgggga  10080
gcagttgtca tgaagggaca agtgagattt tagaaacagg gttgccctct gaattgcata  10140
caatgcttga ggtgtcacac agatgagata tgttggtct aggtatctgg aaggttagac   10200
agtgggggtgc cttaaatggg ctttggtttt tgttcttggt acagttcaat agatcttggt  10260
aaacacctac tatgttgcca ggtgttcatg gttatacggc ttgtgctcgt gcaggcttgt  10320
gtctgaattt cggaatgggg tgggtgtatt ccctgcaggc tgctgccatc cagtagccca  10380
ctgtggggga agctccgtgt ggatgtcaag acatacctaa gtgcggtggt gcaggtacag  10440
aatcccagga gacctggtca tgtctgatag tctggtgctc tcttacaccc cagattccag  10500
tgactttctc ttcttctta gctggtagcc tgtctagcgg aagccacggt gtctgcagct   10560
```

```
gtcctgcagc atatcagcag cttggttcct tactacctga cattccctaa gcagtgccga    10620
atgttgctca aggtacgtta gcttgtcctt gtcctactcc tggctagaat agaggcagca    10680
tttgtgccta tacttgctct gctcctactg tgtcctctac tcagcaaggg tccccagtct    10740
cagatggtcc cccgtccttt caggacagcg tggcttagta atgtgagact aggctccact    10800
gaggcatgcg tgctagccat ggagggttct aggccaggaa aggcagcgat gtatcttttt    10860
tcagaggatg gtggttctgt ggagcacggg tgaagaatct ctgcgggtcc tggccttcct    10920
ggtactcatc agagtctgcc ggcacaagaa ggaagccttc cttggtccca ttctgaaggt    10980
agcgtgagtc ttctatttgt tcattaaggt ctgtgttggg aattgtggtt gatggtcctt    11040
acgaggactt gacaccaaac tctgatcata gttttcttac caagaaaatt gggtgatggt    11100
gggaacagga acccatggtc ttgtgggtat tggtggtgat ggtgggaggg gctcttttcc    11160
tctgggtacg agaacgttat acctagaaaa taggaacgtg tctgaggcca ccaccaagat    11220
cagatcctgc tgtgtagctc caggcctgga gtggcatcac ctggactcct gctgtacaga    11280
cctagctcga agtagagcgt ctctacttcc ttcctcggcc ttcggtccag tccctgccta    11340
gtcctcatct tacccttctc ttgtacacct tcctctcttc tgcatatctt agattatttg    11400
tggtgggtac aagtgtgtag gctgagaaac atcagagttc ttgagtgctg gaaccattc    11460 aggaattgag tctgcagctc tttcagacgg cagttctaat ggaaacccct aggtgtgggc    11520
aggtggcttg gaactgaaca gtcgttgctc aggtggctct taattttggt ttgtcagcaa    11580
atgtacatca tgtatgtgag aaactgcaag ttcacctccc ccagtaccct ccccctcata    11640
agcttcatgc aacggacact gactgaaatg cttgccttgg accccagcgt ctcctatcag    11700
cacgccttcc tctacatccg acagcttgcc gtccacctgc ggaatgctat gaccgcaggc    11760
aagaaggtag gaggaggtca gacccttcga agccagtagc cccacccggg ccttagggtg    11820
gctagaagcc actctttaat gggggaggct gctcagcgct gagggaggct ttgggtggtt    11880
ctggcaggga agaacgggcc taggatgtgg actcactctc cccaggagac acaccagtct    11940
gtgtacaact ggcagtatgt gcactgcctc tacctgtggt gtcgagtcct gagtaccctt    12000
ggttccagtg agatcctgca gccgctactc taccctctct cacagatcat cattggctgt    12060
atcaagtgag ttcagggaca gggctatgtt agattagcct aggggttggg ggcagcaagt    12120
tcctcttggt atagggcaga agttcctgat ttgctagctt ctgtgaatta cattatacaa    12180
agaattttct cgggtggcca caccttaaat cttagctttt gtggctatag tctctgagga    12240
agggcctgag aagatgaact ggatgtggat ttcaggcagc tgggcttcgc agtcagcctc    12300
agcttaggta aataggttag gtgtccacag tgtagcacct atatggaccc ggctcgggcc    12360
cttgtgctat tggagggcaa tcagatgtag ttctaagtgc ttttgatagt ctgcgaatgt    12420
gctgtgccta cctcttttggc taggagggggc ctctgtgtcc tctcgagctt tctcctgaca    12480
ctggagactg agctaggaag gggaagaggc aggtggtaca agaaaacaag gcagcaggtg    12540
gtgaggaaag gaggcaggag tgaatgaact aagctaaagt tggatgagcg cctttcagtc    12600
tcgcagctga gcagtggggc accaaggcca agcattttgg ttgtccctgt tggttttgct    12660
gactgtttaa attactattc cccatgggtg ctatgagtac ccaccctgta ggagtggcca    12720
gggtctcctg gagttggagc ttgtgaacgg ggaggagtca gaggcagcgg gcagttaact    12780
gatgtttggg cctggctacc tgactgggct ccgctcctct tttctccagg ttgttgccca    12840
ctgctcgatt ttatccattg cgcatgcatt gtgtacgtgc cctgacactg ctgtcccaga    12900
ccatcggcac cttcatacct gtcctgccct tcattctcga ggtgactgtg ctgggcacaa    12960
```

```
ctcgtgttgg acttagaaat gtctttagga aaccacacct ccgtctctgc gtctgccagt   13020
gctaacttct aacaatgacc ccgtgacccc cctctctttg cagtccttac agatctgcat   13080
tgagtctctc caagtctcac agttactatg acacctttct cgtttccctt attgtacctc   13140
taccttgagt cgctgtccct gccctcgggc ttcctatcag gtgcagattc cttgagaaag   13200
tgaagcacaa gggtgaatcc aagcccctgc taacaccgac accgcccttt ctttagtcta   13260
tggcgaggat aaaggtggat attgataacc agctctatat attagttagc atcctttgct   13320
cagagaaagg actttcccta cctccaattt attaatcact gtagctggtt caccttctag   13380
caacatgtta cgtaagttct cttatcaggg cttccctata gaacctcccc tctctatgct   13440
tctgtgtgta ccttgtgcct ccttggttta cctgttctgt gtgggcatc ctcggaccaa    13500 gaggttaggc taggctccga tttccctctt aggaaggcca aagtgtatat agagcctgca   13560
aggtttgttg ggtgtggaaa acacagtctc ccttctgtct ttctttattg gtggttttgt   13620
ccatagtgcc tgggatgcgt gaggcccaga tccgtatcta aaggcggtta agtgtatgca   13680
ggcgtcctta tggttatctg tcaagggct cagggctctg gaaggcctgg tcttggggga    13740
tctctttggc tcgggcttac actctgtggg tagattttcc agcaggtgga cttcaatagg   13800
cggccaggtc gcatgagctc caagcccatc aacttctctg tgatcttgaa gctgtccagc   13860
accaacctgc aggagaaggc gtaccgggtg aggctgaact caaggccttc tgggaaaggc   13920
ctggggctat gttttagttg gttacaagg acttaataag gccgttgata tacaagggag    13980
ggattcccat tgtggaccat tgtggttttc ttttgagaca agatctctct attatattgc   14040
tcttgctgtc ctggaacttg ctatattgat caggctagcc ttgaactcac agagttccac   14100
ttttcaaatg ctaagattga ggttttgta gtcatggagc aatgactcct taatctcagt    14160
tcccgtgaag ctgggtgtgg cttgggggg tctgtgcgta ctgttttata gccctggtct    14220
tggagattga gcagagttgg ggtgaaatgt aagaaaatgg gctactgggc ttcatcatct   14280
gatgaggttg ggcctgcccc ccaggacggg ctgctggaac agctgtgtga ccttactctg   14340
gaatacctgc acagccaggc ccacagcatc gctttcccag agttggtgtt gcctactgtt   14400
ctacaggtat gtactcatca tctgacttcc tttccctggc cagaccttgg cgtcctcctt   14460
gtggctatct tggacaatct tttagtaggt ttgtcgtccc cttatgttct agtcctggac   14520
cagtagcaac accgtgttta tccagttacc aatgggctgc cagatccatt ggcgccagtg   14580
cagggagaga gcgatcattt gccttgatag cttaaggaac tttctctagg gactgtggaa   14640
ttaacttgta aaggattatc ggcctctgct gaagttgggc tggggctggg taacttaatc   14700
aggatctcag gaatttgcag acccttcccc agtctgactg gagcctacca tcaactatgg   14760
aagtctaaag cctgggttgg tctggtgccc gttttgtttt tccgtgtggt catggtctct   14820
ctgtgcccct tctgagaatc tgtttgctct cagctcagct attttccatc taggtccttc   14880
tcataggagg gggctggtgc tgtctctttt ctggtactgg tagggattaa gatccattgc   14940
tcacagactt gtcgtggtgt tgctcatacc tgagctatgc ctgggtcagg ctcctatggg   15000
cacaggtgta tgtgtgacgt tacatgtata gctgtgcaca cggctgtgtc gcggttggtt   15060
gcataatgtg gcattggctt cccctgtgt cctcttggct gatgatgtca ggtagtcagg    15120 ataccttag ttttaggctc agcattttag gtgtatggat gtgtggatct agagtagaag    15180
ttagcagatg tgtttcagtt aaaataaaag tagcaaaaaa aaaaaagaa acttttaagg    15240 tttatgtctt gtcacagctc ttcatctgct tacctctcgg gctgcgggga caagcatggt   15300
cttatgcctg tgagacctaa gagattgaca gcaggtcctt gtgattgtca catggctttt   15360
```

```
cactgcttgg acccctcgag ggtgaggaat ggaactgtca ctggagctgt actgagtctt   15420
tcctttctgc agctgaaatc ttttctccgg gagtgcaaag tggctaacta ctgccggcag   15480
gtgcgccagc tgctggagaa agtgcaagag aatgcacgac acatccaaag tcttcgacag   15540
agcgcgacct tcagcgtgtc tgaccggacg gcagtggtgg gttggacttg gcatctgcac   15600
tggaatggtg ctgcctgggg tcacctgtta gggtgtggtg gatgtttaag ggttttccag   15660
aatgatcatg gtcctgaatt tacttcaatc cttaggatgc gtgggagaag caggttcgtg   15720
aagaggggac cccactcacc agatactacg gccactggaa gaagctgagg gaccgtgaga   15780
tccagctgga aatcagtggc aaagagcggg tatggctggg gtctgtgaag atggcctagt   15840
agaaagtggc caagcaggtt atttgtaaag gggttgggc tgaggggag aagttggaaa    15900 aggaaacgaa atcaggaggg aagaaagaaa ggtgagtttg agtgaaccct gtaagtttct   15960
gtttacctgc tgggcagctg gtccccggta ttgatataga tggttcccga ggcgcagctg   16020
ggccagttct ctcggcctct ccctaccctc acttgttgtt ctgtttcttg gtccttgaag   16080
ctagaagacc tgaacttccc agagatcaaa aggcggaagg tggaagacag gaaggatgaa   16140
gacaggaaag aattaaagga cctgtttgag ttggacagtt ctgagggcga ggacagcacc   16200
gacttctttg agagaggtga ggcctgagct ggagtggttg agagctgtgt gtgtctgggg   16260
cattcatgtc tggctagtgg gcagacctgg tttgttgttt ttaattttta tgtctgtgtg   16320
ttttggctac atgtctgtct gtatccagat ccctgagac tggagttaga gacacttgtg    16380
agcctcagtg tgggcactgg gatcaaaccc atgtccttga accactgagc catctctcta   16440
gcctccagat ctgtttttt tttttttt taaagattta tttatttatt atatgtaagt     16500
acactgtagc tgtcttcaga cactccagaa gagggcgtca gatcttgtta cagatggttg   16560
tgacccacca tgtggttgct gggatttgaa ctcaggacct ttggaagagc agtcgggtgc   16620
tcttacccac tgagccatct caccagccct agatctgttt cttataccac tcattggccc   16680
cttatgtttg agctggggac tcagtattgg taattgtcac catgctgggg cctctatagg   16740
tggcagagag ggctagtggc cctgttgcta ctgctgagac ctggggccct gttgcatgtc   16800
cagagccagc cctcctgtgt agctactcat tgctttgtta tttcacccgg tgtgtgtgtg   16860
tgtctgtgtg tgtgtctgtg tgtgtctgtg tgtgtgtgtg acgaccgttc ttcatttgca   16920
ggagtaccta ggctcccgga agctcaccaa ggactgaaag aagatcagga agaagaagat   16980
aaagaagaag gtgacagcga ttcagagggt aagtggtttc tatatgaaat agattggccc   17040
tggagtctgt ctggaggcca gaccatggga agacagagct ctacgccagg cttctgcccc   17100 tccctgggt gccaggccag ctgctctgta ctctttagca accagctata gcatgctgat   17160
aaatttaatt aatgctgcaa ttaattagtg atgagtaact tctaaagctg gcttttcat    17220 gatatagcag aatttattta tgtggcctct tccttctctg tagatggaga cacagacacg   17280
ggagtggatc tgagcgaact gtggcagctg gctcagggac cacaagatga gctggaggat   17340
cttcagctct cagaagagga ctgagggcct cctgctgcct cctggaggcc tcgacagcaa   17400
ctgtgcggcg agaggacagc agagcgtaaa caggctttta ttgttacagc acagcagaac   17460
aagtgtacta ggagccattt tgaccctgaa agggagggaa ctgtttctgc agagccttct   17520
gctgccggaa gccgaaggct gaccctgatg ttgtcccagt tcagtgggg gagggcggct   17580 ccatggcctc tcctctccac tttgtctttg gtttgtctgc agagcactgc agttacctct   17640
agaagataaa cccattactt tgtttgttt gtttgtttgt ttgtttgttt gtttgttttt   17700
tcgagacagg gtttctctgt gtagccctgg ctgtcctgga actcactctg tagaccaggc   17760
```

```
tggcctcgaa ctcagaaatc cgcctgcctc tgcctcccga gtgctgggat taaaggtgtg    17820
cgccacctct gcccagctca ttgcttttct tcttaagcct tatgttttcc ttttaaaaat    17880
actctcggca tttttgcatc taaaaagggg aaatacctg ggggcggagt gaggttagca    17940
atttgactgg gaatcacgga gtatgacggt tgcctgccgg atcattggag aagctgggaa    18000
gggtctgggg cacctgaaag cagagctatg gtccctgacc cattctcctg cttgggtgag    18060
gcttgtcctg tgggcaggtg ggtcccttca tacggggagg tggtggttgc tggcgacaga    18120
ggttgatgtc ctgggctgag ctcaggtgct gcaggcttg gtggctgcag cggcagggcc     18180
acagggaagc tggccatgta aagacacgg cccaggcgct tggccaccta caagagacg      18240 aagctgggtg aatacctgct aggtaaaggc gcctagggaa acaactccag gtacagagaa    18300
tcctaaaacc ctctctagag tggtgaaaac actggacaaa cttacttgtg ccctgatctt    18360
gagggcaggc cctagcttca gtcccatggt gttcagaagg tgctcttctg tcagtagagg    18420
caaagtctct ccgtctattc cttgttctct gaatacctgg ggacaaggtg ggcccataga    18480
gtagagttgt agagcttgca tggaaaaata acaaaaggaa agttcttttt tgtgggagac    18540
cgggacattg tccagaactg gccagaacc ctagggacct gccactcccc tcaccctggc     18600
atactcgcca cagccagaaa ggccccccac gaagttgcag acatcatcta cagtccactt    18660
gttgacatcc tcaaggggttg tggtctcctc atcagtgaag agccccccca tggtacctgg    18720
agatagaaag gatgtcacta gggcttgggc tttcccattt cttgcctcc ttccccactg     18780 gctgaccttt ctctgaattg gtaaagtctt tggcttaatg acaaatgatt tttctcccca    18840
cgggatcccc tatcagtggg tgactaaggc tgcccacctg tgtggaagta ggggctcact    18900
gccccgcaag ggaatcccag gggcagtgga gggcagtg tggaccctga tagaagcccc     18960
cttccttctg ctctggtccc tcctgctggg acttggctgg gagtggaggt cccttccctg    19020
gcagctgctg tctcggggtc ctctccatct gagtccttgg atggctcctc agagacttct    19080
tgagcccaga ggccagcccc tgtcgtctcc ttgggttggc tgggctggac accaaggctc    19140
cccttttcgg accggcttcg agcagactcc ttgggtggga taggggtcc tgggcctggg    19200 ggtccctggg gtggcagggc cagtagtggt gctgagctgt gtttcaaaac cagcatggag    19260
ccacgtcgct gcagttcgtc gggaccctcg gggatatgca aggccacctc tggtgccggt    19320
agcagtggcc ggtgaacact gcccagttct ttctgcctaa gcaactctga catttccagc    19380
ctggaccaaa aggacagacg agtcagcctg ggcacgctta gaactgctcc cgctggcctt    19440
gcagtcgctt accgagccag gctctgcttc cgtagaagtt cctgctgccg agctaacatc    19500
tcagcctggg cggagggtag gaagctgaaa cctgggatag aagaaaaggc tgctgaagcc    19560
ggatgctctt cactactttt atctatctgc ctaaagagag cctcatagga acacaaacgg    19620
cttacatacc cgactttctc acctgggtc tgacacacag ctgtgggcat ccccagaaaa     19680
ggaggcggga gatgggagct cattgtgatg tgggcggcat tctggggtga cagcaaaggg    19740
ggtggctgtg acatttccct gtggacagca gaatagtgag cacatgccta ggtccgtctg    19800
tgcacacccc ctctttcctg tcatcacctc tgggtgcacc cctgctaacc cttctagttg    19860
ccgacccctc aagtggccgt tggttttcctg attatggctt gcttgtgtac acacacacac    19920
acacacacac accccgcgcg caagtctcct tgtcagcaca gaggcaatgg ccccatggcc    19980
cacactgcgt cagtaattac cggggtgggg gataccctctc atcctgagca gtgaggggag    20040
gggtgcagga cagggcaatt agccccaatt tgtagatgtg gcagatgctg cagtctgcca    20100
ggatcagggt gagataggat gtgtttggga aacccgggga ccctgcctaa tgctctcctt    20160
```

```
ggcttaactc gtctgccgcg gagactactg tgagcatgat gtctctggag tttatagcag   20220
ggtagggatg gagggggcgt atgtccttca ctctgaatcc tctgtggttg ctttctcctt   20280
gccttcctca acatcccacc accaccacct gtgaggggag ggcctctgct ctcggggcag   20340
ctctactagg ctggaatagt cagagttgct tgacaagaaa attgtatttg gcattcttgc   20400
cagggagtgg gcatttctgc atattttgcc ccccaaattg agtctttgca gtagttttag   20460
gagcttcctg cagtggacct tgaacgtggt gaatgcatta tgcatatatg tgatggaaga   20520
ctcaagggaa agaaagaatt ggccttctca agtaacaagc atagcatgtg gggccttgct   20580
gaagcacgtc ttaataccct tcagagaaag atgtggcagc agctggaacc gccccttccc   20640
ggcgctgaac taggccttgc ttccgtcgat ggtctgctgt agacgagggc aggtgaactt   20700
ccaagccact gggacccctc agtgttgcag ttgctacttc ctggcgtacc ctaagcagat   20760
ctgagaaggg aggtgatagc gggccccccct gataagctcc cgtaggattt cccctttcca   20820
tcttggtgag cagggcattg gcccggtgaa ggtatgaaca gagtgggagg aggagactct   20880
cacatgtcct gagcctgctt ttgtgtcaca ggctagagga tcagcaggga aggcactttg   20940 cttaacacc tacatgctgt agccaggcaa gtgaacttga aaaggaatgt gaataagtag    21000
gtcatcgaaa ctggagaaga aaggctccaa catgtagagt attagtgcta atttggtttg   21060
aatattcaca aggtcagagg tggaagggca tagggctgct ccaagtaggt gagtgggaca   21120
agagtctatg gattaggagg ggacctcaaa cagaagcctg cccaggtaac tcctttctag   21180
acaggagaca agaacaggaa ggacttgccg tccctataaa gcgattcata gcatacatgg   21240
ttataatagc agataccact gactagcagc aacacacaat cacagacctg catggttgtg   21300
cccccattgc atttaggaag agcggaggct ccgagcccct ttaatccacc tgctcaagct   21360
ccacttctct accgctctgc ctgtttataa atcacgtagc tgaaaagggg acgtgggcct   21420
agctagggct tgaagccaaa tcccagaccc taataagccc aggccacccc agtcatgcgc   21480
cacgcaatgg tgattgacag ccagcttgct tgcacagtct cctgcacagg ccagcagagc   21540
tgggtaagca attaaaaaga aagatttttta aattattaac atttagtgaa ttattcaggc   21600
tctcggtgcc tgagctgctg ccctagggaa cagcgccttc tgcaagaatc aggaatcctt   21660
ttcccttctc tgagccccccg tccacttctg ccagaaaaga caagatttgt ccggtgctgt   21720
agcagcacag ggtgtctcac aagtcctcgg tagcaaggac ggtgcctcaa ggcttggctt   21780
ccctcaagca acctggggtg catcctgact gtgacgcagg ttcctatttt tgccatgccc   21840
tcctccctgt gtatcaacaa aacctgaaaa gtctgacaca gcatcaacac gaccacagat   21900
tcacgtattg cactgaccac tctgggagaa actagcacag gccagaggcc acatctcttc   21960
aacaaagaac aggtgaacaa actcttctgt cccaccctca cctgggctcc tcggggacgc   22020
acagtagagg actgaggcca gtgaggctgc atcactaccc ggaagcccct ctatgtattc   22080
aatcctggtc ttggtgttga cctccaagca tccagatctt tttcttgggg ttggcttagt   22140
ggggtggaaa ggtaagagag atttggctca cttgaagtct gagcgccggc cgtgggggtg   22200
gcacataccg tggctgggga tacccaagtg gtagagacgt tgagtttcct caaaggaact   22260
ggcctcactc agggccgaca taagctgatg gtagtggtcc tcaggggcca ttgtagactc   22320
tagcttggga agcagcgaag tcgctgttgg acagagcaca tggtgaggac cacggggaaa   22380
gtcaaggctt cttatggttt ccacccaagg tctggggagc ccttcaggac ccagttgctc   22440 cccccccttcc ctgtgacctg catccttttc cagagtcggg ctttcacctt ggggggtcctt   22500 gcttctggcc ttcttctctg aagagcagtg actggtgatg caggggcagc tcagcctctt   22560
```

-continued

```
gcccaacagg tcgcctgtag aggatagagt gagccccacc cagtgtctca tggcttcgag   22620
agaaagccat ctctgcctta gctcagtctg gagccccaat caccactatg ttctccctgg   22680
cagttaaaga ccttgtccga tctggtgtcc caggctagag agcacgatga caggtagatg   22740
gagagtgcag taaagacaaa gcgatcctga cgctggcctt gggcacgtaa gtaacagtga   22800
gagctctgca tcagtgtttc cccagtcagt ctcctgtaag ctccttgcct ctcccctcgg   22860
tgcatttgcc catctgcata tccaggtctg ggttcttaat gggactccta agcatttcac   22920
tccatagtgc acagtctata tgtgctatgc ttttatgagg ccaggccaga cactgcttac   22980
aatatcccca gagataatac atgccgaatc tcaggcatta attgacccaa ttccagactg   23040
gcctgaacac tgctgcctaa cttcctcctg agctcctgcc ctgaggctag ggcctttgct   23100
gaacagccca tgacatcgcc atcatggctt caagctaagg ttcctgtctc tgccctcctt   23160
atcctcacca gctaggggag tgtggaggaa caattccgtg ggtgattcaa aatctccata   23220
atgcccaata aggggctgct tctacttgtg tgcccaccct ccctcaaagc tggtggtgtc   23280
agcgccagga ctgaattcca tttaaaaaaa attccttaat ttgtcatttt tatcagattg   23340
gggaagtgtg gcagcaaaaa cgctgatcaa tctccacgtt atggctgaca gaatggtgct   23400
aataacttat tgatctcaac tacctcactg ctgttagtct agcaggccat ctcagcctcc   23460
gccccagaga aagagacagc gcctactgtc tggacaaggg ctccacccat aatatctcaa   23520
ggcagatggg tccagcagac agataatggg tatctggctt cacttggtgc caccaatagt   23580
ttatcagaga ccagtaggca gaagaggcag cagctggagt agacaggaag gagggtccct   23640
caggtctgtg tggcctggtc tcactcactt tgtacctgtt attcttgtcc caacccacag   23700 atcccctttta aggactaggc aagggctctt ttcacagcag tctattctca ctttaaaagt   23760
ggctaccccc aaaggagagg gggagggaga gagggagaaa aggagg               23806
```

<210> SEQ ID NO 7
<211> LENGTH: 163
<212> TYPE: PRT
<213> ORGANISM: Artificial Sequence
<220> FEATURE:
<223> OTHER INFORMATION: Description of Artificial Sequence: Synthetic construct

<400> SEQUENCE: 7

```
Met His His His His His His Gly Met Ala Ser Glu Phe Gly Ser Ala
  1               5                  10                  15

Gly Ser Arg Lys Arg Arg Leu Ala Glu Leu Thr Val Asp Glu Phe Leu
             20                  25                  30

Ala Ser Gly Phe Asp Ser Glu Ser Glu Ser Glu Ser Glu Asn Ser Pro
         35                  40                  45

Gln Ala Glu Thr Arg Glu Ala Arg Glu Ala Ala Arg Ser Pro Asp Lys
     50                  55                  60

Pro Gly Gly Ser Pro Ser Ala Ser Arg Arg Lys Gly Arg Ala Ser Glu
 65                  70                  75                  80

His Lys Asp Gln Leu Ser Arg Leu Lys Asp Arg Asp Pro Glu Phe Tyr
                 85                  90                  95

Lys Phe Leu Gln Glu Asn Asp Gln Ser Leu Leu Asn Phe Ser Asp Ser
            100                 105                 110

Asp Ser Ser Glu Glu Glu Glu Gly Pro Phe His Ser Leu Pro Asp Val
        115                 120                 125

Leu Glu Glu Ala Ser Glu Glu Glu Asp Gly Ala Glu Glu Gly Glu Asp
    130                 135                 140
```

```
Gly Asp Arg Val Pro Arg Gly Leu Lys Gly Lys Lys Asn Ser Val Pro
145                 150                 155                 160

Ser Thr Ile

<210> SEQ ID NO 8
<211> LENGTH: 176
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 8

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Glu Gly Thr Pro Leu Thr Leu Tyr Tyr Ser His
        35                  40                  45

Trp Arg Lys Leu Arg Asp Arg Glu Ile Gln Leu Glu Ile Ser Gly Lys
    50                  55                  60

Glu Arg Leu Glu Asp Leu Asn Phe Pro Glu Ile Lys Arg Arg Lys Met
65                  70                  75                  80

Ala Asp Arg Lys Asp Glu Asp Arg Lys Gln Phe Lys Asp Leu Phe Asp
                85                  90                  95

Leu Asn Ser Ser Glu Glu Asp Asp Thr Glu Gly Phe Ser Glu Arg Gly
            100                 105                 110

Ile Leu Arg Pro Leu Ser Thr Arg His Gly Val Glu Asp Asp Glu Glu
        115                 120                 125

Asp Glu Glu Glu Gly Glu Glu Asp Ser Ser Asn Ser Glu Asp Gly Asp
    130                 135                 140

Pro Asp Ala Glu Ala Gly Leu Ala Pro Gly Glu Leu Gln Gln Leu Ala
145                 150                 155                 160

Gln Gly Pro Glu Asp Glu Leu Glu Asp Leu Gln Leu Ser Glu Asp Asp
                165                 170                 175

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ile Arg Asp Leu Ile
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gln Asn Leu Leu
1               5

<210> SEQ ID NO 11
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Ala Phe Leu Val
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Thr Glu Leu Leu
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Ile Gly Cys Ile
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Pro Phe Ile Leu
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ile Leu Arg Pro Leu
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Leu Arg Val Leu Ala Phe Leu Val Leu
```

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Arg Arg Lys Met Ala Asp Arg Lys Asp Glu Asp Arg Lys Gln Phe
 1               5                  10                  15

Lys

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Pro Leu Ala Gln Val Ile Ile Gly Cys Ile Lys Leu Ile Pro
 1               5                  10

<210> SEQ ID NO 19
<211> LENGTH: 39
<212> TYPE: DNA
<213> ORGANISM: Homo sapiens
<220> FEATURE:
<221> NAME/KEY: CDS
<222> LOCATION: (1)..(39)

<400> SEQUENCE: 19 gag tct ctg cgg gtg ctg gct ttc ctg gtc ctc agc aga           39
Glu Ser Leu Arg Val Leu Ala Phe Leu Val Leu Ser Arg
 1               5                  10

<210> SEQ ID NO 20
<211> LENGTH: 13
<212> TYPE: PRT
<213> ORGANISM: Homo sapiens

<400> SEQUENCE: 20

Glu Ser Leu Arg Val Leu Ala Phe Leu Val Leu Ser Arg
 1               5                  10

<210> SEQ ID NO 21
<211> LENGTH: 36
<212> TYPE: DNA
<213> ORGANISM: Homo sapiens

<400> SEQUENCE: 21
tctagacggg tggcggcttt cgaagtcgcc agcaga                       36

<210> SEQ ID NO 22
<211> LENGTH: 51
<212> TYPE: DNA
<213> ORGANISM: Homo sapiens
<220> FEATURE:
<221> NAME/KEY: CDS
<222> LOCATION: (1)..(51)

<400> SEQUENCE: 22 aaa cga agg aag atg gct gac agg aag gat gag gac agg aag caa ttt     48

```
Lys Arg Arg Lys Met Ala Asp Arg Lys Asp Glu Asp Arg Lys Gln Phe
 1               5                  10                  15 aaa                                                                    51
Lys

<210> SEQ ID NO 23
<211> LENGTH: 17
<212> TYPE: PRT
<213> ORGANISM: Homo sapiens

<400> SEQUENCE: 23

Lys Arg Arg Lys Met Ala Asp Arg Lys Asp Glu Asp Arg Lys Gln Phe
 1               5                  10                  15

Lys

<210> SEQ ID NO 24
<211> LENGTH: 15
<212> TYPE: DNA
<213> ORGANISM: Homo sapiens
<220> FEATURE:
<221> NAME/KEY: CDS
<222> LOCATION: (1)..(12)

<400> SEQUENCE: 24 cgt ctc gag gcg atg                                                    15
Arg Leu Glu Ala
 1

<210> SEQ ID NO 25
<211> LENGTH: 4
<212> TYPE: PRT
<213> ORGANISM: Homo sapiens

<400> SEQUENCE: 25

Arg Leu Glu Ala
 1

<210> SEQ ID NO 26
<211> LENGTH: 15
<212> TYPE: DNA
<213> ORGANISM: Homo sapiens

<400> SEQUENCE: 26
gatatccaat ttgaa                                                       15

<210> SEQ ID NO 27
<211> LENGTH: 701
<212> TYPE: PRT
<213> ORGANISM: Drosophila melanogaster

<400> SEQUENCE: 27

Asp Ala Ile Arg Lys Thr Lys Pro Gln Thr Thr Ser Glu Thr Lys Val
 1               5                  10                  15

Thr Pro Arg Asn Pro Lys Gln Lys Val Ala Glu Pro Val Lys Asn Gly
                20                  25                  30

Lys Thr Thr Lys Lys Gly Phe Lys Ser His Lys Glu Glu Leu Glu
            35                  40                  45

Gly Leu Lys Asp Ile Asp Pro Glu Phe Tyr Asp Phe Leu Lys Asn Asn
         50                  55                  60

Asp Lys Lys Leu Leu Asp Phe Asn Asp Thr Asp Asp Asp Glu
 65                  70                  75                  80

Glu Gly Asp Glu Glu Asp Lys Glu Asp Thr Val Thr Lys Glu Ser Lys
                 85                  90                  95
```

-continued

```
Asp Asp Glu Asp Asp Glu Glu Lys Tyr His Lys Pro Ser Lys Asp Leu
            100                 105                 110
Glu Val Ala Ser Asp Glu Ser Gln Lys Ile Thr Leu Asn Leu Leu His
        115                 120                 125
Gln Trp Glu Gln Gln Leu Gln Ala Asn Ile Ser Ile Asp Ile Val Arg
    130                 135                 140
Lys Val Ile Gln Ala Phe Asn Ser Ala Leu Ala Ser Ile Ser Gly Gly
145                 150                 155                 160
Glu Asn Lys His Asn Ala Ala Ala Phe Lys Val Val Gly Ala Ala Ala
                165                 170                 175
Phe Asn Gly Val Ile Gln Leu Cys Val Ile His Leu Gln Pro Ala Ile
            180                 185                 190
Ile Arg Leu Leu Gly Val Arg Pro Asn Ser Ser Leu Pro Leu His Lys
        195                 200                 205
His Lys Lys Trp Val Lys Val Arg Gly Cys Leu Arg Tyr Tyr Leu Thr
    210                 215                 220
Asp Leu Ile Arg Leu Val Glu Gln Val Ser Ser Pro Asn Ile Leu Gly
225                 230                 235                 240
Val Leu Leu Lys His Leu His Gln Met Ala Gly Met Val Val Pro Phe
                245                 250                 255
Ser Ala Leu Gly Lys Thr Ile Leu Lys Arg Leu Val Val Leu Trp Ser
            260                 265                 270
Thr Gly Asp Glu Thr Val Arg Val Leu Ala Phe Leu Cys Ile Leu Lys
        275                 280                 285
Ile Thr Arg Lys Gln Gln Ala Thr Met Leu Asn His Val Leu Lys Ala
    290                 295                 300
Met Tyr Leu Ala Tyr Val Arg Asn Ser Lys Phe Val Ser Pro Asn Thr
305                 310                 315                 320
Leu Pro Gly Ile Asn Phe Met Arg Arg Ser Leu Val Glu Met Phe Ala
                325                 330                 335
Leu Asp Leu Asn Val Ser Tyr Gln His Val Phe Leu Tyr Ile Arg Gln
            340                 345                 350
Leu Ala Ile His Leu Arg Asn Ala Val Ile Leu Lys Lys Lys Asp Ser
        355                 360                 365
Phe Gln Ala Val Tyr Asn Trp Gln Phe Ile Asn Ser Leu Arg Leu Trp
    370                 375                 380
Ala Asp Leu Leu Gly Ala Ser Ala Asn Lys Pro Gln Leu Gln Pro Leu
385                 390                 395                 400
Ile Tyr Pro Leu Val Thr Ile Ala Thr Gly Val Ile Arg Leu Ile Pro
                405                 410                 415
Thr Ala Gln Tyr Phe Pro Leu Arg Phe His Cys Leu Gln Thr Leu Ile
            420                 425                 430
Ser Leu Ala Lys Glu Thr Asn Thr Tyr Val Pro Val Leu Pro Leu Ile
        435                 440                 445
Val Glu Val Leu Lys Ser Asn Thr Phe Asn Arg Lys His Ser Ala Val
    450                 455                 460
Ser Met Lys Pro Val Gln Phe Thr Cys Val Leu Arg Leu Asn Lys Gly
465                 470                 475                 480
Gln Leu Ala Glu Asn Gly Phe Arg Asp Glu Val Ile Glu Gln Val Cys
                485                 490                 495
Gly Leu Leu Leu Glu Tyr Leu Ala His Glu Ser Thr Ser Leu Ala Phe
            500                 505                 510
Ser Asp Leu Val Val Pro Thr Val Met Ala Ile Lys Thr Tyr Leu Lys
```

```
                    515                 520                 525
Glu Cys Arg Asn Ala Asn Tyr Ala Arg Lys Leu Lys Gln Leu Leu Glu
            530                 535                 540

Lys Ile Gln Glu Ser Ala Arg Phe Ile Glu Gln Gln Arg Gly Lys Ser
545                 550                 555                 560

Thr Phe Asp Ile Lys Asp Ala Gln Ala Val Ala Ala Trp Glu Gln Gln
                565                 570                 575

Leu Arg Leu Lys Arg Thr Pro Leu Asp Val Tyr Tyr Ala Ser Trp Leu
            580                 585                 590

Lys Thr His Glu Thr Lys Lys Arg Arg Gln Ala Ala His Thr Asp Glu
595                 600                 605

Ile Ala Asp Tyr Asp Val Pro Lys Leu Lys Lys Leu Pro Val Thr Gly
        610                 615                 620

Val Pro Val Arg Asn Glu Asn Gly Glu Val Glu Leu Phe Pro Ser Asp
625                 630                 635                 640

Ser Glu Asp Glu Gly Asp Asp Gly Leu His Leu Gly Ser Asp Asp Asp
                645                 650                 655

Asp Asp Glu Asp Val Gln Glu Glu Glu Glu Val Glu Val Glu His Pro
            660                 665                 670

Lys Ala Lys Lys Ala Ala Thr Val Glu Asp Asp Tyr Asp Glu Ala Gly
        675                 680                 685

Gly Ala Val Asp Ile Val Lys Asp Leu Asp Leu Asn Glu
    690                 695                 700

<210> SEQ ID NO 28
<211> LENGTH: 632
<212> TYPE: PRT
<213> ORGANISM: Saccharomyces cerevisiae

<400> SEQUENCE: 28

Ala Ala Gly Thr Arg Glu Gln Gln Gln Leu Lys Asp Met Ser Val Glu
1               5                   10                  15

Thr Phe Phe Glu Lys Gly Ile Glu Ile Pro Lys Glu Asn Lys Lys Leu
            20                  25                  30

Lys Lys Lys Thr Thr Lys Glu Gln Ser Asp Glu Asp Ser Ser Ser Ser
        35                  40                  45

Glu Glu Glu Glu Asp Met Gly Gln Ser Met Ala Lys Leu Ala Glu Lys
    50                  55                  60

Asp Pro Glu Phe Tyr Lys Tyr Leu Glu Glu Asn Asp Lys Asp Leu Leu
65                  70                  75                  80

Asp Phe Ala Gly Thr Asn Pro Leu Ser Gln Asp Glu Gly Glu Asp Ala
                85                  90                  95

Glu Arg Asn Ser Asn Ile Glu Glu Lys Ser Glu Gln Met Glu Leu Glu
            100                 105                 110

Lys Glu Lys Ile Glu Leu Ser Leu Lys Leu Val Arg Lys Trp Lys Lys
        115                 120                 125

Gln Leu His Asp Ser Pro Ser Leu Lys Leu Leu Arg Asn Ile Ile Ser
    130                 135                 140

Ala Phe Lys Val Ala Val Asn Leu Asn Lys Glu Glu Asn Ile Glu Asp
145                 150                 155                 160

Tyr Lys Tyr Ala Ile Thr Asp Glu Lys Ala Phe His Glu Leu Met Phe
                165                 170                 175

Met Val Leu Lys Asp Val Pro Gln Ala Ile Gln Lys Met Ala Pro Tyr
            180                 185                 190

Lys Ile Val Lys Gly Ala Arg Thr Leu Pro Asn Gly Gly Asn Val Ser
```

```
              195                 200                 205
Arg Val Ser Ser Ile Val Lys Ser His Ala Gly Ser Leu Leu Ile Leu
    210                 215                 220

Leu Asn Asp Ile Thr Asn Thr Glu Thr Ala Ala Leu Val Leu His Ser
225                 230                 235                 240

Val Asn Glu Leu Met Pro Tyr Leu Leu Ser Tyr Arg Arg Ile Leu Lys
                245                 250                 255

Glu Leu Ile Lys Ser Ile Val Gly Val Trp Ser Thr Thr Arg Glu Leu
            260                 265                 270

Thr Gln Ile Ala Ser Phe Ala Phe Leu Ile Asn Thr Thr Lys Glu Phe
        275                 280                 285

Lys Lys Ser Met Leu Glu Thr Thr Leu Lys Thr Thr Tyr Ser Thr Phe
    290                 295                 300

Ile Lys Ser Cys Arg Lys Thr Asn Met Arg Ser Met Pro Leu Ile Asn
305                 310                 315                 320

Phe Gln Lys Asn Ser Ala Ala Glu Leu Phe Gly Ile Asp Glu Val Leu
                325                 330                 335

Gly Tyr Gln Val Gly Phe Glu Tyr Ile Arg Gln Leu Ala Ile His Leu
            340                 345                 350

Arg Asn Thr Met Asn Ala Asn Ser Ala Glu Ala Tyr Lys Ile Val Tyr
        355                 360                 365

Asn Trp Gln Phe Cys His Ser Leu Asp Phe Trp Ser Arg Val Leu Ser
    370                 375                 380

Phe Ala Gly Ser Glu Ser Pro Leu Arg Gln Leu Ile Tyr Pro Leu Val
385                 390                 395                 400

Gln Val Thr Leu Gly Val Ile Arg Leu Ile Pro Thr Pro Gln Phe Phe
                405                 410                 415

Pro Leu Arg Phe Tyr Leu Ile Lys Ser Leu Ile Arg Leu Ser Gln Asn
            420                 425                 430

Ser Gly Val Phe Ile Pro Ile Tyr Pro Leu Leu Ser Glu Ile Leu Thr
        435                 440                 445

Ser Thr Ala Phe Thr Lys Ala Pro Lys Lys Pro Asn Leu Ala Ala Phe
450                 455                 460

Asp Phe Glu His Asn Ile Lys Cys Thr Gln Ala Tyr Leu Asn Thr Lys
465                 470                 475                 480

Ile Tyr Gln Glu Gly Leu Ser Glu Gln Phe Val Asp Leu Leu Gly Asp
                485                 490                 495

Tyr Phe Ala Leu Tyr Cys Lys Asn Ile Ala Phe Pro Glu Leu Val Thr
            500                 505                 510

Pro Val Ile Ile Ser Leu Arg Arg Tyr Ile Lys Thr Ser Thr Asn Val
        515                 520                 525

Lys Leu Asn Lys Arg Leu Ser Thr Val Val Glu Lys Leu Asn Gln Asn
    530                 535                 540

Ser Thr Phe Ile Gln Glu Lys Arg Ser Asp Val Glu Phe Gly Pro Thr
545                 550                 555                 560

Asn Lys Ser Glu Val Ser Arg Phe Leu Asn Asp Val Ala Trp Asn Lys
                565                 570                 575

Thr Pro Leu Gly Ser Tyr Val Ala Val Gln Arg Glu Val Lys Glu Glu
            580                 585                 590

Lys Ala Arg Leu Met Arg Glu Ser Met Glu Gln Asp Lys Glu Arg
        595                 600                 605

Glu Thr Glu Glu Ala Lys Leu Leu Asn Ser Leu Glu Ser Asp Asp Asp
    610                 615                 620
```

```
Asn Glu Asp Val Glu Met Ser Asp
625                 630
```

<210> SEQ ID NO 29
<211> LENGTH: 687
<212> TYPE: PRT
<213> ORGANISM: Caenorhabditis elegans

<400> SEQUENCE: 29

```
Ala Gly Leu Lys Lys Arg Lys Val Ile Ser Lys Arg Ile Lys Ile Glu
 1               5                  10                  15

Lys Lys Pro Ser Ser Glu Asp Glu Gly Ser Ser Asp Glu Glu Val Pro
            20                  25                  30

Lys Leu Asp Gly Glu Gly Ser Leu Asp Gly Ser Glu Asp Glu Asp Asp
        35                  40                  45

Gly Thr Val Thr Val Glu Lys Gly Gly Val Lys Lys His Lys Leu Asp
 50                  55                  60

Leu Glu Lys Leu Lys Gln Ser Asp Pro Glu Phe Phe Lys Phe Leu Gln
 65                  70                  75                  80

Gln Glu Asp Ala Asp Leu Leu Asn Met Glu Asp Asp Gly Asp Asp Asp
                85                  90                  95

Glu Asp Asp Asp Glu Asp Asp Glu Glu Glu Glu Glu Ser Asp
            100                 105                 110

Asp Asp Glu Asp Glu Glu Asp Asp Lys Arg Lys Pro Lys Ile
            115                 120                 125

Lys Ser Asp Asn Ser Gly Arg Leu Ile Val Asp Ser Asn Val Tyr Ser
        130                 135                 140

Tyr Leu Gln Gln Val Leu Ser Thr Pro Thr Asn Pro Ser Asp Val Arg
145                 150                 155                 160

Met Ala Val Asp Val Phe Val Ala Cys Val Ala Arg Val Gly Ala Asp
                165                 170                 175

Ile Glu Ala Pro Lys Tyr Val Ile Asn Glu Gln Ser Ile Phe Glu Ala
            180                 185                 190

Val Val Arg Met Cys Phe Gln Ala Met Pro Asp Ile Leu Lys Arg Leu
        195                 200                 205

Leu Lys Ala Lys Pro Glu Gly Asp Lys Val Leu Phe Ser Lys Thr Ala
    210                 215                 220

Ile Lys Lys Tyr Gln Thr Tyr Val Arg Thr Tyr Leu His Ala Met Ile
225                 230                 235                 240

Val Phe Leu Asn Glu Val Gln Thr Thr Glu Val Leu Ile Ala Thr Ile
                245                 250                 255

Lys Ala Met Thr Arg Leu Val Asp Leu Tyr Ala His Phe Ser Arg Met
            260                 265                 270

Ser Lys Leu Leu Ile Lys Ala Val Val Arg Ile Trp Ser Arg Lys Thr
        275                 280                 285

Leu Glu Cys Arg Leu Pro Ala Phe Val Cys Met Asn Leu Leu Val Lys
    290                 295                 300

Asn Tyr Pro Gln His Phe Val Pro Leu Tyr Lys Thr Ala Tyr Val Ala
305                 310                 315                 320

Phe Val Ala Asn Ser Lys Ile Val Thr Asn Glu Thr Trp Pro Leu Leu
                325                 330                 335

Gln Phe Met His Arg Thr Phe Ala Glu Leu Thr Ile Leu Asn Pro Glu
            340                 345                 350

Gln Ala Tyr Lys Tyr Ala Phe Val Tyr Ile Arg Gln Thr Ala Val His
        355                 360                 365
```

Leu Arg Asn Ala Met Ile Ser Gly Arg Lys Asp Leu Ile Phe Ser Ile
            370                 375                 380

Tyr Asn Trp Gln Met Met Gln Cys Met Tyr Met Trp Val Arg Val Ile
385                 390                 395                 400

Ala Lys Ala His Ser Ala Glu Gln Ile Gly Glu Leu Val Tyr Pro Leu
                405                 410                 415

Ile Gln Val Ile Val Gly Ile Phe Lys Leu Cys Asn Ala Pro Thr Phe
            420                 425                 430

Leu Pro Leu Arg Leu His Cys Cys Gln Leu Leu Ile Gln Leu Gln Ala
                435                 440                 445

Ser Cys Thr Asn Tyr Ile Pro Ile Leu Gln Val Ser Cys Asp Cys Leu
450                 455                 460

Glu Glu Leu Lys Ser Lys Pro Lys Pro Val Lys Gly Ala Val Lys Leu
465                 470                 475                 480

Pro Asp Ile Glu Cys Thr Leu Lys Cys Ser Ser Gln Phe Ser Asp Leu
                485                 490                 495

Pro Gln Trp Arg Lys Val Ile Ser Glu His Val Phe Arg Thr Met Met
                500                 505                 510

Gln Ser Ala His Leu Leu Ala Ser Gln Ala Ala Phe Pro Asp Val Val
            515                 520                 525

Leu Pro Ile Asn His Arg Ile Ser Ala Ile Leu Glu Thr Met Lys Asn
530                 535                 540

Gly Asp His Ala His Leu Phe Arg Gly Phe Gln Thr Lys Leu Lys Glu
545                 550                 555                 560

His Ser Arg Phe Val Leu Asp Val Leu Ala Arg Lys Ser Val Asp Ile
                565                 570                 575

Asn Asp Glu Met Gln Val Arg Ala Val Arg Phe Asp Leu Asn Asn His
            580                 585                 590

Asp Ser Pro Ile Lys Thr Phe Tyr Arg Gln Trp Glu Lys Val Trp Lys
            595                 600                 605

Met Lys Glu Arg Ser Ala Val Glu Asn Ser Lys Lys Asp Asp Lys Lys
            610                 615                 620

Lys Lys Lys Glu Glu Glu Ala Ala Ala Lys Lys Arg Lys Pro Asn
625                 630                 635                 640

Glu Thr Val Glu Asp Glu Asp Val Lys Pro Glu Val Ser Lys Ala
                645                 650                 655

Lys Arg Lys Arg Ile Lys Ile Gly Ala Ala Lys Lys Ala Asp Ala
                660                 665                 670

Ser Val Pro Asp Gln Phe Ala Asp Met Ser Met Trp Ser Asp Glu
            675                 680                 685

<210> SEQ ID NO 30
<211> LENGTH: 717
<212> TYPE: PRT
<213> ORGANISM: Arabidopsis thaliana

<400> SEQUENCE: 30

Met Gly Ala Lys Glu Leu Lys Gly Phe Glu Ile Asp Lys His Phe Lys
1               5                   10                  15

Ser Asn Val Asp Asp Lys Lys Arg Val Lys Lys Leu Lys Ser Lys Lys
            20                  25                  30

Leu Glu Ala Glu Glu Glu Leu Asn Asn Val Gln Glu Ile Asp Ala Met
            35                  40                  45

Glu Gln Lys Ser Asp Lys Lys Arg Gly Lys Lys Val Lys Ser Lys Lys
        50                  55                  60

```
Ala Glu Ala Glu Glu His Glu Glu Leu Lys Arg Leu Gln Glu Lys
 65                  70                  75                  80

Asp Pro Asp Phe Phe Gln Tyr Met Lys Glu His Asp Ala Glu Leu Leu
                 85                  90                  95

Lys Phe Asp Ala Thr Glu Ile Glu Asp Ala Asp Val Glu Pro Asp
                100                 105                 110

Thr Asp Leu Glu Asp Thr Glu Lys Glu Gly Asp Glu Ala Thr Lys
            115                 120                 125

Met Glu Ile Ala Lys Lys Val His Val Gln Lys Thr Ile Thr Ala Ser
130                 135                 140

Met Val Asp Ala Trp Ser Lys Ser Ile Glu Asp Glu Ala Lys Leu Gly
145                 150                 155                 160

Gly Val Arg Ser Ile Leu Arg Ala Tyr Arg Thr Ala Cys His Tyr Gly
                165                 170                 175

Asp Asp Thr Gly Asp Asp Gln Ser Thr Lys Phe Ser Val Met Ser Ser
                180                 185                 190

Glu Val Phe Asn Lys Ile Met Ile Tyr Val Leu Ser Glu Met Asp Gly
                195                 200                 205

Ile Leu Arg Lys Leu Leu Arg Phe Pro Glu Gly Thr Lys Glu Thr Ile
210                 215                 220

Leu Glu Leu Thr Asn Thr Arg Pro Trp Lys Asn Tyr Asn His Leu Val
225                 230                 235                 240

Lys Ser Tyr Leu Gly Asn Ser Leu His Val Leu Asn Gln Met Thr Asp
                245                 250                 255

Thr Glu Met Ile Thr Phe Thr Leu Arg Arg Leu Lys His Ser Ser Val
                260                 265                 270

Phe Leu Ala Ala Phe Pro Ser Leu Leu Arg Lys Tyr Ile Lys Val Ala
                275                 280                 285

Leu His Phe Trp Gly Thr Gly Ser Gly Ala Leu Pro Val Val Ser Leu
                290                 295                 300

Leu Phe Leu Arg Asp Leu Cys Ile Arg Leu Gly Ser Asp Cys Val Asp
305                 310                 315                 320

Asp Cys Phe Lys Gly Met Tyr Lys Ala Tyr Val Leu Asn Cys Gln Phe
                325                 330                 335

Val Asn Ala Asp Lys Leu Lys His Ile Ser Phe Leu Gly Asn Cys Phe
                340                 345                 350

Ile Glu Leu Leu Gly Thr Asp Ile Ser Ala Ala Tyr Gln His Ala Phe
                355                 360                 365

Val Phe Ile Arg Gln Leu Ala Met Ile Leu Arg Glu Ala Leu Asn Thr
                370                 375                 380

Lys Thr Lys Glu Ala Phe Arg Lys Val Tyr Gln Trp Lys Phe Ile His
385                 390                 395                 400

Cys Leu Glu Leu Trp Thr Gly Ala Val Cys Ala Tyr Ser Ser Gln Ser
                405                 410                 415

Glu Leu Arg Pro Val Ala Tyr Pro Leu Ala Gln Ile Ile Thr Gly Val
                420                 425                 430

Ala Arg Leu Val Pro Thr Ala Arg Tyr Thr Pro Leu Arg Leu Arg Cys
                435                 440                 445

Val Arg Met Leu Asn Arg Leu Ala Ala Ala Thr Gly Thr Phe Ile Pro
450                 455                 460

Val Ser Met Leu Leu Val Asp Met Leu Glu Met Lys Glu Leu Asn Arg
465                 470                 475                 480

Pro Pro Thr Gly Gly Val Gly Lys Gly Val Asp Leu Arg Thr Leu Leu
                485                 490                 495
```

```
Lys Val Ser Lys Pro Ala Val Lys Thr Arg Ala Phe Gln Glu Ala Cys
                500             505                 510

Val Tyr Thr Val Val Glu Glu Leu Val Glu His Leu Ser Gln Trp Ser
            515             520                 525

Cys Ser Val Ala Phe Phe Glu Leu Ser Phe Ile Pro Thr Ile Arg Leu
    530             535                 540

Arg Ser Phe Cys Lys Ser Thr Lys Ala Glu Arg Phe Arg Lys Glu Met
545             550                 555                 560

Lys Gln Leu Ile Ser Gln Ile Glu Ala Asn Ser Glu Phe Val Asn Lys
                565                 570                 575

Lys Arg Ala Leu Ile Lys Phe Leu Pro Asn Asp Leu Ala Ala Glu Ser
                580                 585                 590

Phe Leu Glu Asp Glu Lys Lys Ala Gly Lys Thr Pro Leu Leu Gln Tyr
            595                 600                 605

Ala Glu Ile Ile Arg Gln Arg Ala Gln Gln Arg Asn Glu Ser Leu Val
            610                 615                 620

Glu Ser Asp Val Ile Val Gly Glu Asn Ser Ala Val Phe Gly Lys Asn
625                 630                 635                 640

Ala Pro Ser Ser Asp Asp Glu Asp Asp Glu Arg Met Glu Lys Gly
                645                 650                 655

Ala Ala Ala Phe Asn Ser Ser Trp Leu Pro Gly Ser Asp Ser Lys Glu
            660                 665                 670

Lys Glu Pro Glu Glu Glu Lys Thr Lys Lys Lys Arg Lys Arg Gly
                675             680                 685

Gly Lys Ser Lys Thr Glu Lys Lys Gln Asp Glu Gln Gly Leu Gly Glu
            690                 695                 700

Asp Asp Val Val Glu Asp Phe Val Leu Ser Ser Asp Glu
705                 710                 715

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 31

His His His His His His
  1               5
```

REPRESSOR OF SKELETAL MUSCLE DIFFERENTIATION, NUCLEIC ACIDS CODING THEREFOR AND THE USE THEREOF IN DIAGNOSIS AND THERAPY

The present invention relates to a novel corepressor whose function has been substantially elucidated. Various possible uses of this corepressor are disclosed.

The designation GRIM1 which has been chosen for the corepressor of the invention represents the abbreviation of the designation "Global Repressor Involved in Myogenic Differentiation". This name was chosen because the cloned factor plays an important part in particular during skeletal muscle differentiation.

In recent years a large number of molecules which prove to be responsible for direct transcriptional regulation has been found. Besides the DNA-binding factors (in the narrower sense referred to as transcription factors), there are regulatory molecules which, as coactivators, facilitate gene expression or which, as corepressors, actively bring about transcriptional repression. Cofactors are promiscuous and can be recruited in various combinations by various DNA-binding partners. The alternation between associated coactivator and corepressor complexes is an important regulatory step within cellular differentiation processes.

For the example of skeletal muscle differentiation, over the course of years a cascade of transcription factors which are necessary for myogenesis has been found. Besides other transcription factors, the bHLH proteins MyoD, myf5, MRF4 and myogenin bring about execution, in a proliferating myoblast precursor cell, of the genetic program which results in a terminally differentiated functional skeletal muscle cell. During the course of this phylogenesis, the cell passes through a cell cycle arrest, and it fuses with other committed muscle cells to give multinuclear myoblasts and expresses skeletal muscle-specific structural and metabolic enzymes.

The associated cofactors acting within this process have been investigated only in recent years. Positively regulated expression of myogenically specific genes takes place for example through a functional association of MyoD with the coactivator protein p300. Acetylated MyoD has far greater transcriptional activity than unmodified protein.

On the other hand, there are certain corepressors which actively prevent targeted repression of the expression of muscle-specific genes in proliferating cells. Thus, for example, a functional association between MyoD and the corepressor N-CoR has been described, and in this way revealed a new field of activity for the cofactors which had previously been assigned only to nuclear hormone receptors. In addition, members of the histone deacetylase (HDAC) family have been described as being involved in skeletal muscle differentiation (C2C12 cell culture model) and showing a subcellular relocalization during the first steps of differentiation.

Association of HDACs with active repression is regarded as one of the basic requirements for negative transcriptional regulation, because the reaction catalyzed by the HDACs is transmitted directly to the chromatin and provides a mechanistic explanation for the observed effects.

The data shown in this application describe GRIM1 as a novel "bona fide" transcriptional repressor with a novel mechanism of repression. GRIM1 is not associated with an HDAC activity, and the GRIM1-mediated repression cannot be influenced by specific HDAC inhibitors. GRIM1 is able to inhibit directly, via acidic domains in the N and C termini, the acetylation of histone N termini (one of the preconditions for directed transcriptional activation). Repression domains which have not to date been characterized in detail within GRIM1 likewise have high potential for repression of transcription activity. GRIM1 has the potential in transient transfections for dose-dependent repression of both complex and synthetic minimal promoters. Based on these data, the newly cloned factor has been designated GRIM1 (Global Repressor Involved in Myogenic differentiation).

GRIM1 shows relocalization during skeletal muscle differentiation, although at a distinctly later time than previously described for the HDACs 4, 5 and 7 in connection with MEF2-specific transcription. The available data suggest that the repression potential of GRIM1 must not be switched off until later times during skeletal muscle differentiation so that terminal differentiation of the myotubes is possible. In addition, GRIM1 likewise shows a subcellular change of localization during preadipocyte differentiation.

One function of GRIM1 is involvement as repressor in regulating the differentiation of skeletal muscle cells. The data show that GRIM1 shows a distinctly different role than the involved factors previously described. Elucidation of the in vivo role of GRIM1 takes place via GRIM1 knockout animals and transgenic mice. In the transgenic animals, GRIM1 mutants will express under skeletal muscle-specific promoters which can no longer reach the nucleus or which can no longer be transported out of the nucleus. The phenotype of the mice which results from the generated atypical localization of GRIM1 will contribute further to understanding the function of GRIM1 within differentiation processes.

Application of the present invention is particularly in the area of degenerative muscle disorders or in controlling muscle atrophy in the aging man. The therapeutic modification of the function of GRIM1 may in such cases counteract premature muscle degeneration or actively intervene in processes which build up muscle.

The present invention therefore relates firstly to polypeptides having a sequence of at least 20 consecutive amino acids from the sequence of hsGRIM1 (hs=*homo sapiens*) having the sequence ID No. 3.

The polypeptides of the invention preferably have a sequence of at least 40 consecutive amino acids.

The polypeptides more preferably have a sequence of at least 80 consecutive amino acids, even more preferably a sequence of at least 120 consecutive amino acids and most preferably the polypeptides of the invention have a sequence of at least 200 consecutive amino acids from Seq. ID No. 3.

The invention further relates to polypeptides which have a sequence of at least 20 consecutive amino acids from the mmGRIM sequence (mm=*mus musculus*) having the Seq. ID No. 4.

These polypeptides more preferably have a sequence of at least 40 consecutive amino acids, even more preferably a sequence of at least 120 consecutive amino acids and very particularly preferably a sequence of at least 200 consecutive amino acids of Seq. ID No. 4.

The present invention further relates to antibodies which bind specifically to an epitope of a polypeptide of the invention. The antibodies of the invention can be prepared by customary standard methods. Either the polypeptides coding for GRIM1 can be used to immunize suitable laboratory animals such as, for example, rabbits or goats, and it is possible in this way to prepare suitable polyclonal antibodies. The antibodies of the invention may be directed against epitopes such as conformational epitopes, but also against peptides of the invention.

As an alternative to this it is possible to prepare suitable monoclonal antibodies by methods which have been well known since the publication by Köhler and Milstein in 1975 and belong to the standard repertoire of an average molecular biologist.

Antibodies of this type can be employed in therapy. However, to do this, it is usually necessary to prepare humanized antibodies, because antibodies having constituents derived from animals may cause unwanted side effects. If the binding regions of a suitable antibody have been sequenced, these sequences can be incorporated into a human basic antibody structure, and an antibody of this type can be used in therapy.

An alternative area of use of antibodies of this type is in diagnosis. It is perfectly possible for simple polyclonal antibodies, with which qualitative and/or quantitative detection of the presence of GRIM1 polypeptides in the cells or cell compartments of interest is possible, to suffice for this purpose. The average skilled worker can carry out suitable diagnostic methods with antibodies of this type. The present invention further relates to medicaments which comprise a polypeptide of the invention.

These medicaments are preferably employed for the treatment of disturbances of skeletal muscle differentiation and for the treatment of disturbances of fat cell differentiation.

The medicaments of the invention may comprise a polypeptide having the complete GRIM1 sequence or a suitable part of the sequence. The medicaments are administered in a suitable form to the patients to be treated. Oral or preferably parenteral pharmaceutical formulations are suitable in this connection.

The mechanism of action of the medicaments of the invention relies on modulation of the function of GRIM1. During skeletal muscle differentiation, GRIM1 is transported from the nucleus into the cytoplasm. The medicaments of the invention can intervene in this differentiation process by either specifically blocking importation or else blocking exportation. This can be achieved by incorporating the suitable segments of the polypeptides into appropriate formulations so that the target site of interest can be reached.

It has also been found within the scope of the present invention that GRIM1 is involved in further differentiation processes. GRIM1 shows a subnuclear relocalization during adipocyte differentiation. Involvement of GRIM1 in various other regulatory processes emerges from the findings of the present invention, in particular from the experimental data which show that GRIM1 shows a repression of a wide variety of complexes and synthetic promoters, and expression of GRIM1 is ubiquitous.

The present invention further relates to a method for identifying substances which influence the biological function of a polypeptide of the invention. This entails the substance to be identified being brought into contact with the polypeptide in a test system. It is possible with this test system to identify substances which interact with the GRIM1 polypeptide and inhibit or enhance the biological function of GRIM1.

The systems used according to the invention are preferably cellular differentiation systems which make use in particular of myogenic C2C12 cells or rapidly and inducibly differentiating $10T_{1/2}$ MyoD-ER cells. Detection of GRIM1 or the GRIM1 localization is possible for example immunohistologically. Suitable methods are, inter alia, the use of fluorescence-coupled or enzyme-coupled antibodies in a direct coloring step.

It is also possible to provide suitable cell lines which comprise an appropriate genetic construct with a GRIM1 gene. The substances to be investigated can then be brought into contact with the cells, and the effect of the substance to be investigated can be determined by appropriate comparative tests.

It is possible in a further embodiment to introduce suitable genetic constructs into laboratory animals and to use a transgenic animal for the test methods.

It is possible in a further embodiment of the invention to incubate recombinantly produced GRIM1 fragments in cell-free test systems with substances to be tested, and to obtain the desired result of the test by use of a suitable reporter molecule.

A further aspect of the invention is represented by the cDNA which codes for hsGRIM1 (*homo sapiens*) and which has a sequence of at least 1200 consecutive nucleotides from Seq. ID No. 1.

Another aspect of the invention is represented by the cDNA which codes for mmGRIM1 (*mus musculus*) and which has a sequence of at least 1200 consecutive nucleotides from Seq. ID No. 2.

The cDNAs of the invention can be employed in transfection vectors which have a cDNA of the invention. A preferred possibility in this connection is an adenoviral vector.

These transfection vectors are used to produce cells which have been transfected with such a vector.

BRIEF DESCRIPTION OF THE DRAWINGS

FIG. 1: The cDNA sequence (SEQ ID NO: 1) of human GRIM1.

FIG. 2: The full-length cDNA sequence (SEQ ID NO: 2) of mouse GRIM1.

FIG. 3: A comparative demonstration of homology between human and mouse GRIM1 at the cDNA and at the protein level including conserved sequence motifs.

FIG. 4: A comparison of the amino acids and establishment of a consensus sequence between GRIM1 of human, mouse, *D. melanogaster, S. cerevisiae, C. elegans*, and *A. thaliana*. SEQ ID NOS 4, 3 & 27-30 are disclosed respectively in order of appearance.

FIG. 5: The genomic sequence of hsGRIM1 (NCBI Human Genome Server, Chromosome 1 map view, build 27, December 2001). Exons have a shaded background, and the putative poly-A site is underlined. The sequence corresponds to Seq. ID No. 5.

FIG. 6: The genomic sequence of mmGRIM1 including 5.5 kb flanking sequences (established from the public NCBI mouse genome db and the commercial Celera mouse genome gb). The exons have a shaded background, and intronic sequences are depicted in pale. Exon/intron junctions are depicted in bold. The putative poly-A site and the putative transcription start are underlined. As yet incompletely assembled sequence fragments are depicted by "N". The genomic mouse sequence has the Seq. ID No. 6.

FIG. 7: A UNIGENE database analysis on EST expression selected in homology to mm/hsGRIM1 protein. The accession numbers of the IMAGE clone or of the sequences which are unknown in some cases, and the tissue type from which the cDNAs were isolated, are indicated. GRIM1 appears to be expressed ubiquitously also at the protein level. In total, 308 ESTs were found, and those which show an unambiguous tissue assignment are listed.

FIG. 21: The GRIM1 AR interaction domain is located between aa460-609. Regions of the protein depicted in white have not yet been expressed recombinantly.

DETAILED DESCRIPTION OF THE INVENTION

Figure 8:
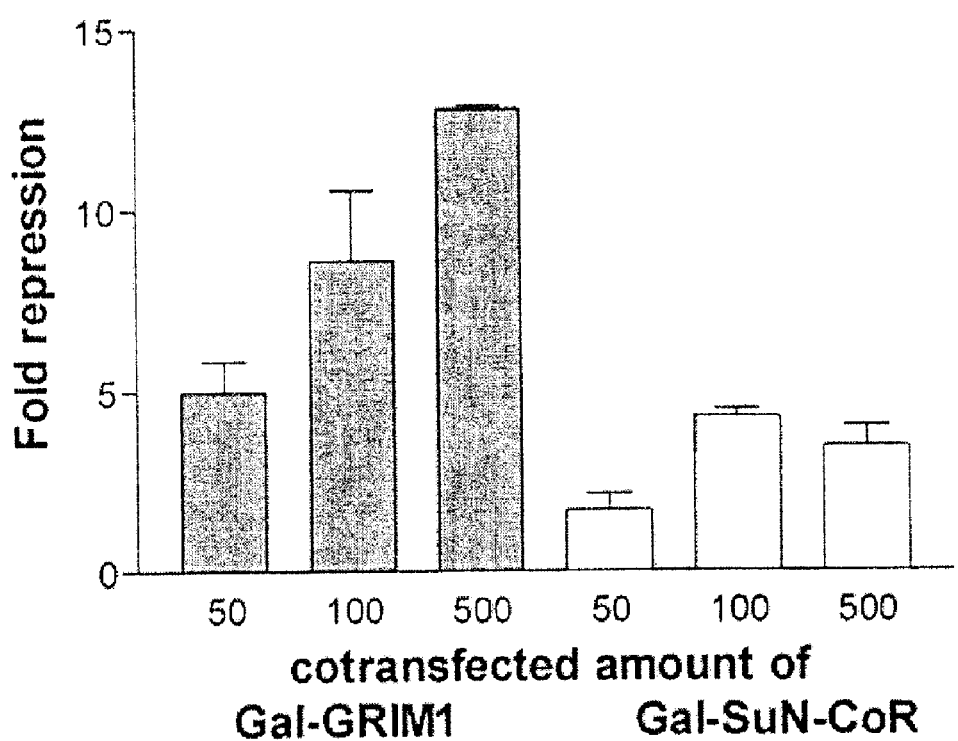
FIG. 8: Gal-GRIM1 is a stronger repressor than Gal-SuNCoR. 293 cells were cotransfected with G5E1bTATA-LUC reporter and the stated amounts of corepressors. The same effect can be observed on testing complex promoters ($Gal4_{3x}$-tk-LUC).

In the examples which are described in detail below, besides customary standard methods, the following methods were preferably used, and the underlined sections of the methods are explained in more detail hereinafter:

Method 1 (Transient and Stable Transfection of Cell Culture Cells):

The cells were cultured in the media recommended by the ATCC on 15 cm cell culture dishes under sterile conditions. Cells are subcultured in a ratio of 1:5 to 1:20 every two to three days and kept at a maximum of 60% confluence. Old medium is removed, and the cells are washed with PBS buffer and treated with trypsin/EDTA solution (0.25% trypsin, 0.04% EDTA in PBS buffer) until they are detached from the culture dish. The cells are isolated in fresh medium and subcultured on new subculture dishes.

PBS buffer: 137 mM NaCl; 2.7 mM KCl; 8 mM $Na_2HPO_4$; 1.8 mM $KH_2PO_4$

Media used: DMEM (Gibco BRL), 100 IU penicillin G/ml, 100 μg/ml streptomycin, 2 mM glutamine, 10% fetal calf serum. As differentiation medium for C2C12 and L6 cells, 10% FCS was replaced by 2% horse serum. 10T1/2 MyoD-ER cells were cultured in hormone-free serum, and 1 μM estradiol, 10 μg/ml insulin and 10 μg/ml transferrin were supplemented as differentiation medium.

To determine the transcriptional properties of hsGRIM1 proteins in eukaryotic cells, pCMX-hsGRIM1 expression plasmids were cotransfected with luciferase (LUC) reporter plasmids. Expression of the particular hsGRIM1 protein in a pCMX expression plasmid is under the control of the cytomegalovirus promoter. Luciferase expression in the LUC reporter plasmids used is controlled either by the thymidine kinase (TK) promoter, an E1b minimal promoter (TATA box), or by the respectively indicated complex promoters.

Transfection takes place by the calcium phosphate method or by the DOTAP liposomes method (Roche Diagnostics, product information). Unless otherwise indicated, $10^5$ cells/well were seeded in 1 ml of culture medium in 12-well dishes. In the $CaPO_4$ method, the plasmid DNA to be transfected is coprecipitated with calcium phosphate, and the precipitate is distributed to the cells capable of division. The calcium phosphate precipitate is prepared by preparing the mixture indicated below for duplicates in 12-well dishes:

| | |
|---|---|
| Reporter plasmid | 1 μg |
| hsGRIM1 expression plasmid | 20-400 ng |
| Carrier DNA (pUC18) | ad 8 μg |
| $CaCl_2$ solution (2.5M) | 20 μl |
| $ddH_2O$ | ad 80 μl |

While agitating (vortexing), 80 μl of 2xBES buffer are slowly and uniformly added dropwise to this mixture. The precipitate is incubated at RT for 10 min and distributed uniformly to the cells (80 μl per well) and, after 8 hours, removed by washing with PBS. The cells are incubated in fresh culture medium for a further 18 to 24 h.

BES buffer (2×): 50 mM N,N-bis[2hydroxyethyl]-2-aminoethanesulfonic acid; 280 mM NaCl; 1.5 mM $Na_2HPO_4.2H_2O$; pH 6.95

Stable transfection of cell culture cells is carried out with the pcDNA6-His system supplied by Invitrogen. Cells are transfected as described above, and stable integration of the plasmids used is detected by the selection antibiotic blasticidin S. Individual clones are picked, expanded and tested by Western blotting and immunodetection for stable expression.
Method 2 (Protein-Protein Interactions):

Yeast two-hybrid interaction assays, mammalian THS, pull-down analyses, immunoprecipitation of cellular proteins followed by immunodetection or in combination with in vitro translated $^{35}$S-methionine-labeled interactants, Phast gel system.

Glutathione S-Transferase Pulldown

A protein is expressed as GST fusion protein in *E. coli*, immobilized on a GST-binding carrier material, and incubated with the potential interactant which is usually radiolabeled. In the subsequent washing steps, proteins which interact only weakly or not at all are washed off the carrier material or the carrier material-bound GST fusion protein. The amount of associated interactant can be determined by fractionation of the proteins by SDS-PAGE and subsequent autoradiography. To check the specificity of interaction between potential interactant and GST fusion protein, the interaction with GST alone is examined.

Aliquots of GST-GRIM1 fragments or GST-containing *E. coli* crude lysate are mixed in each case with 30 µl of glutathione(GSH)-Sepharose and incubated on a bohemian wheel at 4° C. for 1 h. The GSH-Sepharose is pelleted by centrifugation (1' at 2000 rpm) and washed twice in pulldown buffer. The pellet is then resuspended in 500 µl of pulldown buffer and incubated with the in vitro translated, $^{32}$S-methionine-labeled potential interactant at 4° C. on the bohemian wheel for 1 h. After washing three times with pulldown buffer, the GSH-Sepharose pellet is boiled in 30 µl of SDS sample buffer, the proteins are fractionated by SDS-PAGE, and the gel is dried and then subjected to autoradiography.
Pulldown buffer: 20 mM HEPES (pH 7.7); 150 mM KCl; 0.1 mM EDTA; 25 mM MgCl$_2$; 10 mM DTT; 0.15% (v/v) NP40.

Immunoprecipitation

If two proteins interact in solution, the stable complex of the two proteins can be precipitated with an antibody which is directed against only one of the two interactants. In this case, the protein-antibody complex is isolated from the solution with the aid of an antibody-binding carrier material (γ-bind G Sepharose, Pharmacia). To investigate interactions between GRIM1 and putative interactants, either native cell extracts or GRIM1-containing cell extracts are mixed with in vitro translated, $^{35}$S-methionine-labeled target proteins in 500 µl of IP buffer. 5 µg portions of anti-GRIM1 or nonspecific antibodies (rabbit IgG$_1$) are mixed with 30 µl of preequilibrated γ-bind G Sepharose, and the mixture is incubated on a bohemian wheel at 4° C. for 60 min. The G-Sepharose is then pelleted at 2000 rpm for 1' and washed three times with 300 µl each time of ice-cold IP buffer and finally the pellet is boiled in 30 µl of SDS sample buffer. The samples were finally separated by SDS-PAGE, and interaction was detected either by Western blotting or, in the case of the proteins translated in vitro in the presence of $^{35}$S-methionine, by autoradiography.
IP buffer: 20 mM TrisHCl (pH 8.0), 300 mM NaCl, 5 mM EDTA, 0.3% (v/v) NP40, 0.5 mM Pefablock
Cell lysis buffer: 50 mM TrisHCl (pH 8.0), 170 mM NaCl, 0.1% NP40, 50 mM NaF, 2 mM NaO$_3$V$_4$, 0.2 mM DTT, 0.1 mM Pefablock, 1 µg/ml aprotinin, 10% glycerol Method 3 (Detection of Intracellular Localization):

Indirect immunofluorescence, cell fractionation followed by immunodetection.

Indirect Immunofluorescence (IIF)

Cells are seeded in the desired cell density on autoclaved slides and fixed on the support with 5% paraformaldehyde for 10'. Cell membranes are made permeable for antibodies by incubation in 0.2% TritonX100 for 10'. Before the incubation with the primary antibodies, the cells are blocked in 0.2% gelatin (in PBS) at RT for 1 h. Anti-hsGRIM1 antibodies are diluted 1:500 in 0.2% strength gelatin solution and incubated at RT for 1 h. After washing three times with PBS for 5' each time, the respective fluorochrome-coupled secondary antibody is added 1:2000 in 0.2% gelatin solution and incubated in the dark at RT for 30'. After the washing steps, the nucleus is counterstained with DAPI (1 µg/ml PBS, Roche Diagnostics) and the cells are finally washed twice in 0.1% TritonX100 in order to minimize autofluorescences. The slides are preserved in Fluoromount M (Southern Biotechnology Associates) and analyzed using a fluorescence microscope.

Cell Fractionation

Intact nuclei can be isolated and lyzed separately by hypotonic lysis of the cell membrane. Cells are harvested in ice-cold PBS, pelleted and swollen in hypotonic lysis buffer (LB). The cell membrane is permeated by adding NP40 ad 0.1%, and the cytoplasmic constituents are released by gentle shaking and incubation on ice for 15'. Intact nuclei are pelleted by centrifugation at 14 000 rpm for 15', the CP fraction is removed quantitatively, and the protein concentration is determined. Nuclei are lyzed by incubation in nuclear lysis buffer (NLB) while vortexing for 15'. Debris is pelleted and the soluble nuclear preparation is removed. The quality of the preparation is examined by Western blotting and immunodetection with nucleus-specific (e.g. TIF2) and cytoplasmic (e.g. RasGAP) markers.
LB: 10 mM HEPES (pH 7.9), 1.5 mM MgCl$_2$, 10 mM KCl, 0.5 mM DTT, 0.5 mM Pefablock
NLB: 20 mM HEPES (pH 7.9), 420 mM NaCl, 1.5 mM MgCl$_2$, 0.2 mM EDTA, 0.5 mM DTT, 0.5 mM Pefablock, 10% glycerol Method 4 (Detection of Enzymatic Activities):

HDAC assay, INHAT assay, luciferase assays.

HDAC Assay

The histone deacetylation reactions which were carried out were carried out within the framework of a kit obtained from Upstate Biotechnology ($^3$H-labeled histone H3N-terminus as substrate). Alternative substrates used were histones $^{14}$C-acetyl-labeled with p300 or in vivo labeled histones (kindly provided by Dr Martin Göttlicher, Kernforschungszentrum Karlsruhe).

INHAT Assays

INHAT assays were carried out as described by Eckner et al. and by Seo et al. (Eckner et al., 1996, Genes and Development 10 (19), pp 2478-2490, Seo et al., 2001, Cell 104 (1), pp 119-130). Histones or histone mixtures are preincubated with the appropriate peptides in a total of 50 µl of HAT buffer, then mixed with bacterially expressed p300 HAT domains and 0.5 µCi of $^{14}$C-acetyl-coenzyme A, and incubated at 30° C. and 1000 rpm for 2 h. Reactions are stopped by adding SDS Laemmli buffer. Proteins are fractionated in denaturing SDS-PAGE, and the gels are incubated in Amplify (NEN) for 1 h. Acetylations are detected in autoradiographies.

Luciferase Assays

Transiently transfected cells are washed once with PBS and lyzed by adding 50 µl of reporter lysis buffer (Promega) and further disrupted by freezing at −80° C. Cell lysates are transferred into Eppendorf reaction vessels, and cell detritus is pelleted at 14 000 rpm for 2'. 10 µl portions of the lysates are pipetted into 96-well microtiter plates to determine the luciferase activity. The luciferase assay took place in an EG&G Berthold Microluminomat. 40 µl of luciferase assay buffer are injected into the 10 µl of cell lysate, and the resulting chemiluminescence is determined in a time integral of 10". The measured values for the luciferase activity are related to the amount of protein present in the cell lysate. For this purpose, 3 μl portions of the lysates are mixed in 96-well microtiter plates with 100 μl of Bradford assay reagent (Bio-Rad) diluted 1:5 with $H_2O$, and the absorption of the solution is determined at 595 nm. Relative luciferase activities are found from the ratio of the luciferase activity to the protein absorption.

Luciferase assay buffer: 200 mM tricine; 1.07 mM ($MgCO_3$) .4$Mg(OH)_2$; 0.1 M $MgSO_4$, 10 mM EDTA (pH 8.0); 33 mM DTT; 0.5 M ATP; 270 mM acetyl-coenzyme A; 470 mM glowworm luciferin.

The invention is explained in more detail by the following examples:

Example 1

The cloned human GRIM1 gene includes 2250 base pairs and codes for 749 amino acids. The cloned human GRIM1 sequence obtained by sequencing was deposited for the first time as unknown cDNA in 1999 under the accession number AL050019 (protein DKFZp564C186) as part of a "Random EST sequencing" project of the DKFZ in Heidelberg. A sequence which had been revised further was deposited in March 2001 (Wiemann et al., 2001). The function of the protein DKFZp564c186 has not previously been described. The cDNA of the invention is depicted in FIG. 1. The sequence has Seq. ID No. 1.

Example 2

It was possible to calculate from mouse EST databases by comparative analysis with the hsGRIM1 aa sequence from independent ESTs a full-length protein which has a total of 750 amino acids and a total of 60% identical and more than 85% homologous residues to the known hsGRIM1 sequence. Analysis of mouse cDNA libraries and mouse genomic libraries (Celera) have confirmed the calculated and expected mmGRIM1 aa sequence. It was possible to confirm the putative cDNA by RT-PCR analyses. The full-length cDNA of mmGRIM1 has not yet been described or deposited. The sequence having Seq. ID No. 2 is depicted in FIG. 2.

Seq. ID No. 2 was obtained by screening mmEST dbs with the hsGRIM1 aa sequence. The resulting data were compared with mm cDNA dbs and mouse genomic dbs and the virtual mmGRIM1 cDNA was constructed. The sequence was confirmed by RT-PCR and genomic sequencing, and by a direct sequence comparison with the mouse genomic database of Celera Inc.

Example 3

Figure 3:
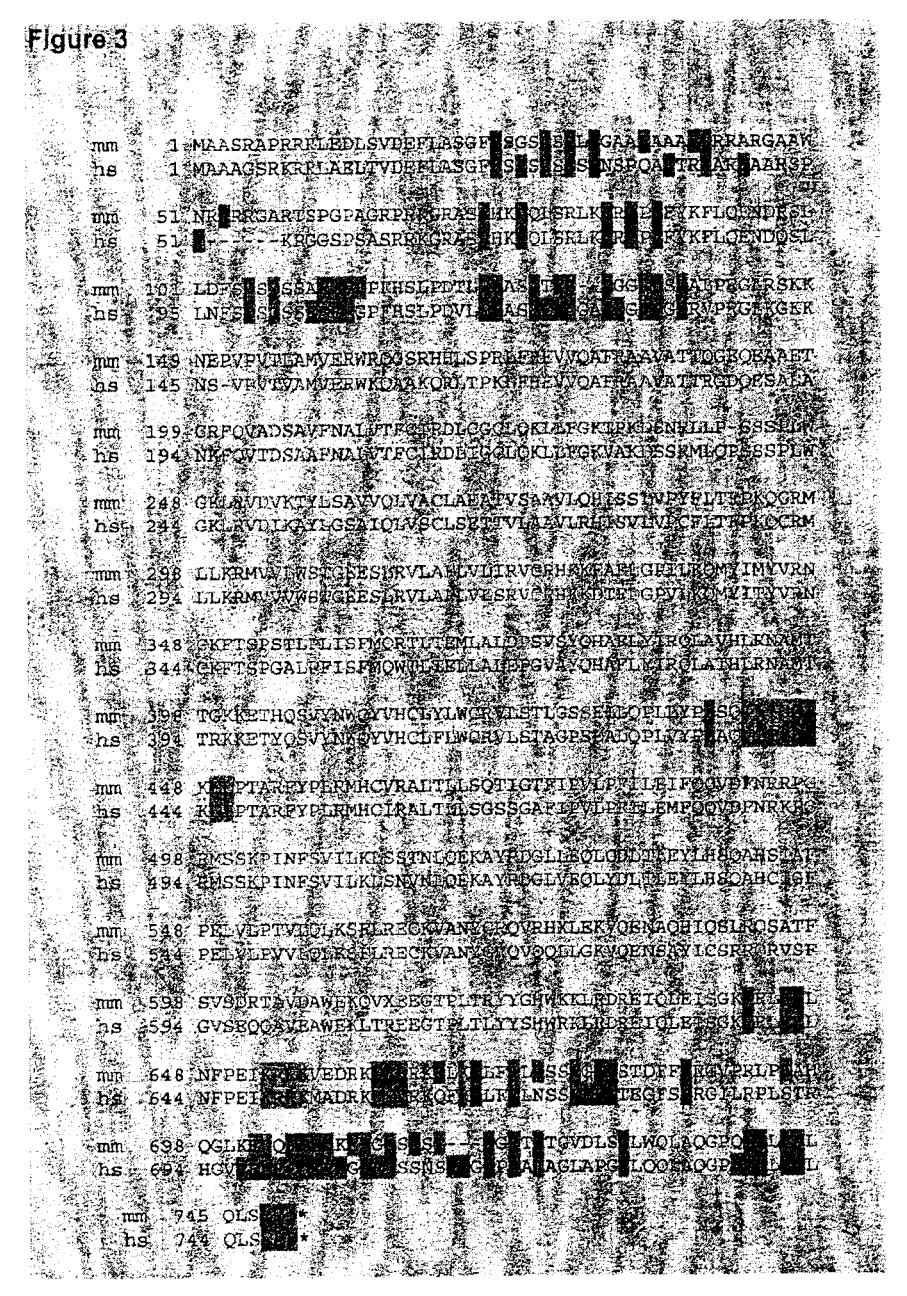

Demonstration of homology between hs and mmGRIM1 at the cDNA and at the protein level is shown in FIG. 3. FIG. 3 depicts a comparative demonstration of the homology of the mmGRIM1 and hsGRIM1 amino acid sequences including conserved sequence motifs.

The amino acid sequence of mmGRIM1 (mouse) is Seq. ID No. 4 and the amino acid sequence of hsGRIM1 (human) is Seq. ID No. 3.

All the functional and potentially interesting sequence motifs described in detail below are sequence-identically conserved in the mouse and the human protein (nuclear localization sequence NLS, nuclear export signal NES, so-called CoRNR box with which corepressors with their associated transcription factors are able to interact). Further motifs are HMG box-like domains within the C terminus and N terminus of GRIM1 of both species, which may possibly bring about contact with DNA and/or histones. In addition, in total 5 so-called LXXLL or related motifs are present within the primary hsGRIM1 aa sequence, an alpha-helical structure which has been reported to be responsible solely for contact of cofactors with their associated transcription factors. Within the mmGRIM1 primary sequence, only 2 of these motifs are conserved vis-à-vis the human sequence. No functional data are available on these motifs as yet. According to calculations, hsGRIM1 mainly has an alpha-helical structure (Columbia University PHD predict program) and is non-globular (GLOBE of the Columbia University PredictProtein server). GRIM1 is localized in the nuclei of proliferating cells, while GRIM1 is relocated from the nucleus to the cytoplasm within cellular differentiation systems (e.g. in C2C12, L6, 10T1/2 and 3T3-L1 cells).

Example 4

For the purposes of the present invention, only hsGRIM1 was used on the basis of cDNA. However, it is assumed that corresponding results will be obtained on use of mouse cDNA. Various constructs were produced by deletion- and sequence-specific point mutagenesis from the human GRIM1 for detailed functional characterization and are compiled in the following tables.

TABLE 1 hsGRIM1 point mutants used

| Name | aa positions | Constructs used |
|---|---|---|
| ΔNES I | L309K, L312A | FLAG, His. Xpress. GFP |
| ΔNES II | L309R, L312A, L315Q, L317A | FLAG, His. Xpress. GFP |
| ΔNLS I | K649A, R650L, R651E, K652A | FLAG, His. Xpress. GFP |
| ΔNLS II | K649A, R650L, R651E, K652A, R661D, K662I, K665E | FLAG, His. Xpress. GFP |
| ΔCoRNR | I439A, I440S, I443A | FLAG |

TABLE 2 hsGRIM1 deletion mutants used

| Name | aa positions | Constructs used |
|---|---|---|
| GRIM1 | 1-749 | jcdcs |
| mut A | 3-609 | Gal4-DBD, FLAG, GFP, GST, His |
| mut B | 3-487 | Gal4-DBD, GST, His |
| mut C | 3-423 | Gal4-DBD, GST, His |
| mut D | 3-245 | Gal4-DBD, GST, His |
| mut E | 3-147 | Gal4-DBD, GST, His |
| mut F | 145-749 | Gal4-DBD, GST, His |
| mut G | 246-749 | Gal4-DBD, GST, His |
| mut H | 485-749 | Gal4-DBD, GST, His |
| mut H | 609-749 | Gal4-DBD, GST, His |
| mut I | 145-609 | Gal4-DBD, FLAG, GFP, GST, His |
| mut J | 468-749 | Gal4-DBD, His |
| mut M | 246-609 | GST |
| mut N | 246-485 | Gal4-DBD |
| mut O | 485-609 | Gal4-DBD |
| mut P | 246-423 | Gal4-DBD |
| mut Q | 423-485 | Gal4-DBD |
| mut R | 145-245 | Gal4-DBD, GST |
| mut S | 246-334 | Gal4-DBD |
| 246-334 | 3-245 | FLAG, GFP |
| Δ 246-334 | 335-749 | FLAG, GFP |

Many of the mutants used carry specific tags such as the Gal4 DNA-binding domain of the yeast GAL4 transcription factor [Gal4-DBD], green-fluorescent protein [GFP], herpes simplex virus transactivator protein 16 [VP16], the antibody-specific signal sequences FLAG tag [FLAG], Xpress tag [XPRESS], c-myc tag [MYC], nickel-binding epitope His tag [His], maltose-binding epitopes [MBP], glutathione-binding portions of glutathione S-transferase [GST]. The use of proteins modified in this way is identified through use of the epitope name in the GRIM1 construct employed. The function of the individual regions of the polypeptides of the invention was investigated by these experiments.

Example 5

Database analyses have shown that hsGRIM1-homologous proteins are to be found in a large number of species. Homologous sequences are to be found in *Shizosaccharomyces pombe, Saccharomyces cerevisiae, Rattus* spec., *Bos bovis, Mus musculus, Drosophila melanogaster, Caenorhabditis elegans, Danio rerio* and also in *Arabidopsis thaliana*. A summarizing overview is obtained from the databases UNIGENE (National Center for Biotechnological Information, NCBI) and of the PredictProtein server of Columbia University and is shown in Table 3 below:

TABLE 3

Representation of the UNIGENE maximally homologous proteins from mouse, rat, *Arabidopsis*, threadworm, fruit fly and baker's yeast. The Swissprot accession numbers, UNIGENE accession numbers, investigated region and maximum homology are indicated (mouse Q9WV70 is not the full-length clone; compare with the described mouse clone described under Seq. ID No. 4).
SELECTED MODEL ORGANISMS IN A PROTEIN-SIMILARITY REPRESENTATION
Organism, protein, percent identity and length of the compared region.

| | |
|---|---|
| *H. sapiens*: | sp: Q9Y3T9 - YU20_HUMAN HYPOTHETICAL 84.9 KDA PROTEIN DKFZP564C186 100% over 753 amino acids (according to the invention) |
| *M. musculus*: | sp: Q9WV70 - YU20 MOUSE HYPOTHETICAL PROTEIN 73% over 267 Aa |
| *R. norvegicus*: | sp: - -\|Segment 1 of 2\| COLLAGEN ALPHA 1 (I) CHAIN 29% over 328 AA |
| *A. thaliana*: | sp: Q9ZPV5 - YU20 ARATH HYPOTHETICAL PROTEIN T30D6.27 IN CHROMOSOME II 27% over 722 AA |
| *C. elegans*: | sp: O17580 - YTB2_CAEEL HYPOTHETICAL 82.0 KDA PROTEIN C07E3.2 IN CHROMOSOME II 27% over 656 AA |
| *D. melanogaster*: | sp: Q9VIF0 - YU20 DROME HYPOTHETICAL PROTEIN CG9246 37% over 681 AA |
| *S. cerevisiae*: | sp. P39744 - YO26_YEAST HYPOTHETICAL 81.6 KDA PROTEIN IN DEDI-RETI INTERGENIC REGION 29% over 674 AA |

FIG. 4 shows a comparison of the amino acids and establishment of a consensus sequence. SEQ ID NOS 4, 3 & 27-30 are disclosed respectively in order of appearance.

Example 6

Genomic Organization

The characteristics of the genomic sequences of mmGRIM1 and hsGRIM1 are compared in Table 4 below. The genomic sequence of both species, including the detailed exon-intron boundaries, is indicated in FIGS. 5 and 6.

TABLE 4

Genomic organization comparison of mm (mouse) versus hsGRIM1 (human).

| | hsGRIM1 | mmGRIM1 |
|---|---|---|
| Number of exons | 19 | 19 |
| Location | Chr. 1p33.36 | Chr. 4p |
| Pseudogenes | Chr. 2 NT_022127.3 Chr. 2 NT_022140.3 Chr. 11 | not known |
| STS | WI-15347 | not available |
| Accession # | GenBank AF276983.1 revised version under NCBI NT_021903 UniGene Hs.134200 Swissprot YU_20 human ENSG00000077716 LokusLink 26155 GenBank AL050019.1 | Accession to the complete sequence is not available. Individual exons are present in EST dbs. |
| OMIM entries | No muscle- or fat-related phenotype. 1p33 is a highly mutated locus and is associated with breast, prostate and brain tumors | No muscle- or fat-related phenotype. |
| Spliced isoforms | nothing known fragmentary ESTs present in various dbs. Northern analyses show only one isoform (exception: heart, 3 isoforms). | nothing known |
| Size of the locus | 14.24 kb (Ensembl) | 12.36 kb (Celera) |
| Quality of the contigs | Chromosome 1 build 27 no longer has any gaps; ordered structure | Ordered up to 5.5 kb 5' - and 3' -flanking, only a small gap between exons 2 and 3 (see annex 2). |

FIG. 5 depicts the genomic sequence of hsGRIM1 (NCBI Human Genome Server, Chromosome 1 map view, build 27, December 2001). Exons have a shaded background, and the putative poly-A site is underlined. The sequence corresponds to Seq. ID No. 5.

FIG. 6 depicts the genomic sequence of mmGRIM1 including 5.5 kb flanking sequences (established from the public NCBI mouse genome db and the commercial Celera mouse genome gb). The exons have a shaded background, and intronic sequences are depicted in pale. Exon/intron junctions are depicted in bold. The putative poly-A site and the putative transcription start are underlined. As yet incompletely assembled sequence fragments are depicted by "N". The genomic mouse sequence has the Seq. ID No. 6.

Example 7

Expression of Recombinant GRIM1 Protein

Many different strategies and expression systems were tested for expression of recombinant hsGRIM1 protein, but only expression of short protein fragments either in the $His_{6x}$ (SEQ ID NO: 31) or in the GST context was successful. The following lists briefly summarize the results and the methods used.

a) Expression systems and brief description of the characteristics for expression of full-length hsGRIM1

Bacterial systems: all the systems used employ *Escherichia coli* safety strains which were purchased from Stratagene.

BL21 (DE3)lysGOLD His-fused: Expression in the pRSET system or in a modified pRSET vector with unique hexahistidine tag, purification on a nickel affinity matrix (TALON, Clontech). Coexpression with GroESL and hspHJK chaperones.

BL21(DE3)lysGOLD GST-fused: Expression in the pGEX4 or 6 systems from Pharmacia, purification on GSH affinity columns, expression inducible by IPTG. Coexpression with GroESL and hspHJK chaperones.

BL21(DE3)lysGOLD NusA-fused: Increase in solubility of the target protein via the NusA content, purification by GPC (Stratagene, Novagen)

BL21(DE3)lysGOLD MBP-fused: periplasmic expression, and thus reduced cytotoxicity (Stratagene, New England Biolabs pMAL system)

BL21(DE3)lysRIL: Codon-optimized BL21 strain (Stratagene). Both hexahistidine- and GST-fused protein expression.

ABLE C: Safety strain which downregulates endogenous plasmid copy numbers by a factor of 4× (Stratagene). Both hexahistidine- and GST-fused protein expression.

ABLE K: Safety strain which downregulates endogenous plasmid copy numbers by a factor of 10× (Stratagene). Both hexahistidine- and GST-fused protein expression.

Plant Systems:

*Physcomitrella patens* moss: stable integration of a CaMV-driven expression plasmid for GST-hsGRIM1 (pRT99/35S-GST-hsGRIM1) via non-homologous recombination, triple selection via two different selection antibiotics and multiple seedings (in cooperation with Prof. Ralf Reski, Plant Biotechnology Institute of Freiburg University).

Cellular Systems: Expression of GST fusion protein in eukaryotic cell culture cells under the control of a constitutively active CMV promoter.

b) Expression of hsGRIM1 Peptide Fragments

Short hsGRIM1 protein fragments were obtained both as hexahistidine- and as GST-fusion proteins only in BL21 (DE3)lysGOLD without coexpression of chaperones. The following table summarizes the expression results obtained; unlisted fragments (compare table of the hsGRIM1 constructs used) could not be expressed:

TABLE 5

| Bacterially expressed hsGRIM1 fragments | |
|---|---|
| His-E (aa 3-147) | +++ |
| His-I (aa 609-749) | +++ |
| His-H (aa 485-749) | ++ |
| GST-E (aa 3-147) | +++ |
| GST-I (aa 609-749) | +++ |
| GST-H (aa 485-749) | ++ |
| GST-M (aa 468-749) | + |
| GST-R (aa 423-485) | ++ |

+++very soluble, readily inducible
++readily inducible, low yield
+solubility poor in some cases, low yield Example 8

Generation and Description of the α-GRIM1 Antibodies Used

To produce hsGRIM1-specific antibodies, two hexahistidine-fused hsGRIM1 protein fragments were expressed in *E. coli*, purified and used to immunize rabbits. Amino acids 3-147 and 609-749 of hsGRIM1 served as epitopes for the antibody.

TABLE 6

N-terminal His$_{6x}$-hsGRIM1 peptide (6x His tag disclosed as SEQ ID NO: 31) (aa 3-147) which was used to immunize rabbits, peptide "E" (Seq. ID No. 7). The antibodies 2719 and 2720 resulted therefrom.

N terminus

MHHHHHHGMASEFGSAGSRKRRLAELTVDEFLASGFDSESESENGPQAETREAREAAPSFDKPGGS

PSASRRKGRASEHMDQLSALKDRDPEFYKFLQENDQSLLNFSDSDSSEEEEGPFMSLPDVLSEASEEE

DGAEEGEDGDRVPRGLKGKKNSVPSTI*C-terminus

TABLE 7

C-terminal His$_{6x}$-hsGRIM1 peptide (6x His tag disclosed as SEQ ID NO: 31) (aa 609-749) which was used to immunize rabbits, peptide "I" (Seq. ID No. 8). The antibodies 2910 and 2911 resulted therefrom.

N terminus

MRGSHHHHHHGMASMTGGQQMGKDLYDDDDKDRWGSEEGTFLTLYYSMWRKLRDREIQLEISGKERLE

DLNFFEIKRRKMADRKDEDRKQFKDLFDLNSSEEDDTEGFSERGIDRPLSTRHGVEDDREDEEEGEED

SSNSEDGDPDAEAGLAFGELQQLAQGPEDELEDLQLSEDD* C-terminus

These regions correspond to the putative INHAT domains of hsGRIM1 and are distinguished in particular by acidic (polyE/polyD) clusters). The corresponding regions of the hsGRIM1 cDNA sequence were generated by restriction digestion with endogenous EcoRI (aa147) and XmaI (aa609) cleavage sites, and the products were cloned into the vector pRSET-B (Invitrogen) (aa 609-749) or pRSET-N⁺/H based on the pRSET-B with the difference that further tags have been deleted and the protein is expressed only with hexahistidine tag) (aa 3-147). The hexahistidine-fused hsGRIM1 protein fragments (aa 3-147 "E", aa 609-749 "I") were overexpressed in *E. coli* BL21(DE3)lysGOLD and, after disruption of the bacteria, purified by TALON affinity chromatography. After isolation and purification from *E. coli*, both polypeptides had an estimated purity of about 80-90%. Rabbits were immunized with the polypeptides, and the raised antiserum was purified. The purified monospecific antibodies against aa 3-147 (2719, 2720) and against aa 609-749 (2910 and 2911) were functionally characterized.

The antibodies obtained in this way were employed in various immunological test methods that made it possible to detect expression of GRIM1. The two antibodies directed against the N terminus show exclusively nuclear localization of GRIM1 in subnuclear compartments which are generally referred to as "speckles". The number and size of the nuclear speckles varies from cell line to cell line, only the exclusively nuclear localization of GRIM1 being common to proliferating cells. The two antibodies directed against the C terminus recognize exclusively nuclear GRIM1 in proliferating cells, but not in speckles, rather in a pan-nuclear localization in the entire nucleoplasm.

Example 9

Expression of GRIM1 mRNA and Protein
cDNA/mRNA Expression of hsGRIM1 and mmGRIM1 hsGRIM1 cDNA expression is ubiquitous according to the report of the Unigene database (UniGene Cluster Hs. 134200, *Homo sapiens* DKFZP564C186/DKFZP564C186 protein with the cDNA library 2334BT0407 used). Expression was detected:
Cervix, Pancreas, nion normal bone, bone, bone marrow, brain, breast, cervix, colon, colon_est, colon_ins, denis_drash, ear, epid_tumor, esophagus, eye, genitourinary tract, germ cell, head_neck, heart, kidney, kidney_tumor, liver, lung, lung_normal, lung_tumor, lymph, muscle, nervous_normal, ovary, pancreas, placenta, pool, pooled, pooled brain, lung, testis, pooled colon, kidney, stomach, pooled lung and spleen, prostate, prostate_tumor, salivary gland, skin, small intestine, stomach, testis, testis-cell line, thymus pooled, tonsil, uterus, uterus_tumor, whole embryo The expression pattern of hsGRIM1 was visualized by Northern blot analysis (CLONTECH hsMTN I and hsMTN II, probe: both full-length hGRIM1 cDNA and N- and C-terminal fragments). The hsGRIM1 transcript size is about 3.3 kb (consistent with the deposited full-length mRNA under Acc. # AL 050019):

heart (1), brain (2), placenta (3), lung (4), liver (5), skeletal muscle (6), kidney (7), pancreas (8), spleen (9), thymus (10), prostate (11), testis (12), ovaries (13), small bowel (14), large bowel (15), peripheral lympocytes (15

The expression of mmGRIM1 in various tissues of the adult mouse (4-6 weeks) was determined by RT-PCR. The following tissues and organs were classified as mmGRIM1-positive:

breast, breast of suckling animals, placenta, testis, ovaries, fat, skin, bone, cartilage, spleen, lung, adrenergic gland, kidney, liver, small bowel, stomach, pituitary, thymus, tongue, skeletal muscle, heart, eye, spinal cord, cerebellum, medulla, hypothalamus, cerebral cortex, whole brain Expression of mmGRIM1 mRNA in embryonic development was determined via RT-PCR with complete embryo mRNA. A distinct mmGRIM1 signal is detected at all times, and no large change in mmGRIM1 mRNA expression during development is observable.

FIG. 7 depicts a UNIGENE database analysis on EST expression selected in homology to mm/hsGRIM1 protein. The accession numbers of the IMAGE clone or of the sequences which are unknown in some cases, and the tissue type from which the cDNAs were isolated, are indicated. GRIM1 appears to be expressed ubiquitously also at the protein level. In total, 308 ESTs were found, and those which show an unambiguous tissue assignment are listed in FIG. 7.

Example 10

Protein Expression

Since various experiments cannot be carried out directly on humans, cell culture and animal experiments which, however, also have validity for the human situation were carried out.
a) The expression of mmGRIM1 protein in primary cells and tissues is indicated below (all the listed cells are classified as GRIM1-positive in a Western blot (86 kD), and for cells the expression was also checked in IIF). Signals are obtained with both antibodies (N- and C-terminal epitope):
    Mouse embryonic fibroblasts
    Human cardiac tissue (DCM patients and normal heart)
    Mouse smooth muscle cells (differentiated, undifferentiated and proliferating)
    Mouse organs: testis, ovaries, spleen, thymus and in a small amount also in prostate and stomach (depicted in the following figure), brain, lung, liver.
b) It was possible to detect expression of mmGRIM1 protein by in situ immunohistochemistry on sagittal sections of E10.5 mouse embryos. mmGRIM1 is expressed in epithelial structures, in the dermomyotome of the rear extremities, in the inner epithelial regions of the neural tube and in other cell populations which are not determined in detail. Concentrated expression is detectable only in the dermomyotome; only a few mmGRIM1-positive cells are detectable in the remaining areas. Ubiquitous expression of GRIM1 was found in mRNA and EST analyses. It was possible to show by in situ immunohistochemical analyses of E10.5 mouse embryos that although there is mmGRIM1 expression in every tissue type, it is far from being in every cell, but rather in specialized cell populations. mmGRIM1 is not expressed in every cell type but distributed over the entire organism in specialized cell types.
c) The expression of rnGRIM1 (rn=rat) in the rat brain was detected by in situ immunohistochemistry in sagittal sections through the brain of a Sprague-Dawley rat (*Rattus norvegicus* ssp).

rnGRIM1 is expressed in Purkinje cells of the cerebellum (nuclear and in some cases also cytoplasmic; strong immunoreactivity in 1-2 subnuclear structures), in bipolar cells of the mitral layer of the olfactory lobe (nuclear and in some cases also cytoplasmic; strong immunoreactivity in 1-2 subnuclear structures), in all cells of the choroid plexus (nuclear and in some cases also cytoplasmic; strong immunoreactivity in 2 subnuclear structures in most cases), in cells which have not yet been determined in detail in the whole region of the cortex (nuclear and in some cases also cytoplasmic; strong immunoreactivity in 1-2 subnuclear structures). rnGRIM1 is not expressed in every cell type, but distributed over the entire brain area in specialized cell types.

d) Expression of GRIM1 protein in cell culture cells. All the stated lines are classified as GRIM1-positive in Western blot analyses (species-inclusive size of about 86 kD) and by indirect immunofluorescence (IIF). Both assays were carried out with all the available α-GRIM1 antibodies. In the proliferative state, GRIM1 is detectable in every cell line in so-called speckle structures (as also described in the literature for many corepressors):

Mouse: NIH3T3 fibroblasts, NIH3T3-L1 preadipocytes, NIH3T3-L1 adipocytes, C2C12 undifferentiated skeletal muscle cells, C2C12 differentiated skeletal muscle cells, N2a neural cells, P19 teratocarcinoma cells, $10T_H$, fibroblasts, Monc-1 neural crest cells Human: HL1 myocardial cells, 293 embryonic kidney cells, LnCaP prostate carcinoma cells, PC3 prostate carcinoma cells Monkey: COS-7 and CV1 kidney cell lines Rat: L6 skeletal muscle cells Hamster: BHK fetal kidney cells e) *Drosophila melanogaster* GRIM1

Expression of an hsGRIM1-like protein in *Drosophila melanogaster* was investigated by Western blotting and whole-fly in situ hybridizations.

No specific signal was detected with the anti-hsGRIM1-specific antibodies (resolution from 36 to 210 kD) either in whole-larva lysate or in whole-cell extracts from fly heads. Likewise, no specific dmGRIM1 (dm=*Drosophila melanogaster*) signal was detectable with the available GRIM1 antibodies in in situ hybridizations with various larval stages.

Example 11 hGRIM1 Interactants

In the protein-protein interaction studies carried out to date, the following potential mm/hsGRIM1 interactants were investigated for direct or indirect interaction with the following methods:

| METHOD for detecting protein-protein interaction | Symbol |
|---|---|
| Co-IP from cell extracts of transfected cells | tfIP |
| Co-IP from cell extracts of untransfected cells | utfIP |
| Co-IP with in vitro translated proteins | ivIP |
| Yeast THS | yTHS |
| Mammalian THS | mTHS |
| Pulldown analyses (direct interaction) | PD |
| Transcriptional studies (transient transfections) | tT |

The underlined factors showed an interaction with hs/mm/maGRIM1 and are described separately at the end of the list (ma=mesocricetus aureus, BHK cells).

Nuclear Hormone Receptors hsAR(PD, utfIP, tfIP, yTHS, tT), hsERα (utfIP, tfIP), hsERβ, rnGR (tT, tfIP), hsMR (tT), hsPR (tT), PPARγ (tT), hsRARα (tfIP), rnTRα (tT), hsTRβ-2 (tT), mmERR1 (tfIP, tT), mmGCNF (PD, ivIP, tfIP, tT), hsRevErbA (tT), mmRVR (tT, tfIP), mmSF1 (tT).

Transcription Factors

Myogenin (ivIP, tT), MEF2A (ivIP), MEF2B (ivIP), MEF2C (ivIP, tT), eHand (ivIP), dHand (ivIP), E47 (ivIP), E12 (ivIP), GATA4 (ivIP), MyoD (ivIP, tT), SEF (ivIP, tT), MRF4 (ivIP, tT), Myf5 (ivIP), Sp1 (tT), CBF (tT).

Transcriptional Corepressors

N-CoR (ivIP, tfIP, utfIP, PD), Sin3A (ivIP, tfIP, utfIP), Sin3B (tfIP, utfIP), SuN-CoR (ivIP, tT), SMRT (ivIP, tfIP, utfIP), HDAC1 (tfIP, utfIP), HDAC2 (tfIP, utfIP), RIP140 (ivIP).

Transcriptional Coactivators:

P300 (tT), FHL2 (ivIP, PD), FHL3 (PD), TIF2 (ivIP), RIP140 (ivIP)

Further factors: Histones H3, H4, H2A, $H_2B$ (PD)

It has been possible to date to show a strong direct interaction between hsGRIM1/mmGRIM1 only with the androgen receptor (hsAR) (detected by tfIP in both directions, utfIP in both directions, yTHS, PD and tT). The interaction with the androgen receptor is ligand-independent and cannot be influenced by the presence of antagonists (Casodex, hydroxyflutamide, cyproterone acetate). GRIM1 interacts both with the "normal" AR having 17 glutamines and with AR isoforms which are associated with Kennedy's disease and comprise polyglutamine-rich insertions (17, 44 and 77 Q), likewise ligand-independently. The PD analyses were carried out with the GRIM1 fragments GST-I/E/H/M, and all the tested fragments apart from GRIM1 "E" (aa 3-147) interacted with the AR, in the sequence M≧H>>I. The physiological relevance of the AR-GRIM1 interaction is described in detail in a separate section.

Weak interactions were detected between hsGRIM1 and the nuclear orphan receptors Germ Cell Nuclear Factor (mmGCNF) and Estrogen receptor Related Receptor 1 (mmERR1) (only ivIP, tfIP and PD), and a weak interaction with the estrogen receptor α (hsERα; interaction was detected only in tfIP and proved to be ligand-independent both in the presence of agonists (estradiol), of antagonists (raloxifene, tamoxifen, ICI) and in the absence of a ligand). The physiological relevance, in vivo colocalization or in vivo interaction is very substantially unclear. It was not possible to show any direct association between GRIM1 and mmGCNF, mmERR1 or hsERα in transient transfections.

GRIM1 shows a strong interaction with the core histones H4, $H_2B$, H2A and H3 in GST pulldown analyses. Recombinantly expressed GST-GRIM1 fusion proteins (GST-aa 3-147 and GST-aa 609-749) show a marked interaction with all four core histones, providing further support for the observed INHAT activity of the N- and C-terminal GRIM1 domains.

Potential mm/hsGRIM1 interactants can be identified by conventional methods. These methods include yeast two-hybrid screen with various cDNA libraries and direct protein biochemical methods such as Co-IP of GRIM1 and associated proteins, fractionation by 2-dimensional gel electrophoresis, mass spectrometric analysis and microspray sequencing of the potentially interacting proteins from various cell culture cell lines (C2C12 differentiated, C2C12 undifferentiated, 3T3L1 differentiated, 3T3L1 undifferentiated, BHK and many more).

Example 12

Physiological Function of GRIM1: Analysis of Repression Potential of hsGRIM1 in Transient Transfections All the described data were obtained with the hsGRIM1 clone. GRIM1 is a potent transcriptional repressor when used as Gal4-DBD fusion protein in transient transfections. Gal-GRIM1 represses expression of reporter genes both of Gal4-RE-controlled complex and synthetic minimal reporter constructs. The repression potential of GRIM1 is distinctly greater for example compared with the corepressor Gal-SuN-CoR. In these experiments, the appropriate corepressors are transiently expressed as heterologous Gal4-DBD fusion proteins in cells. The repression capacity on various synthetic promoter-reporter constructs compared with equal quantities of transfected wild-type Gal4-DBD is determined by luciferase reporter gene expression (FIG. 8).

Figure 9:
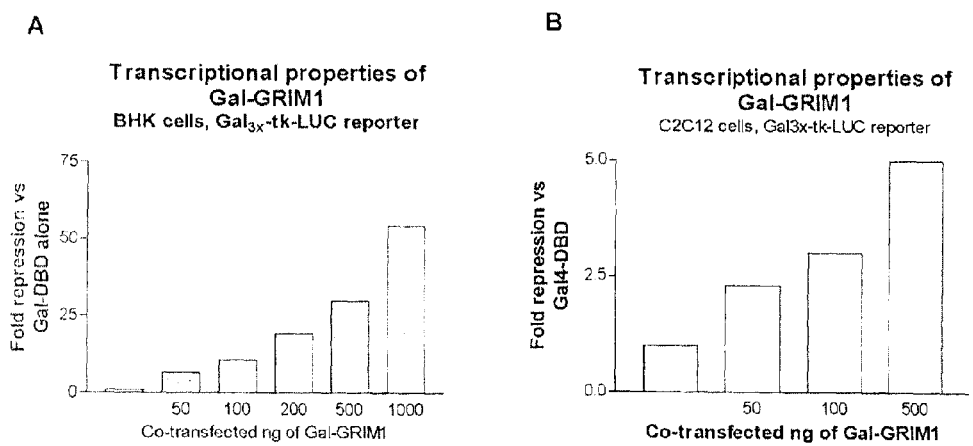
FIG. 9: A. Gal-GRIM1 acts as a transcriptional repressor in BHK cells. B. Gal-GRIM1 acts as a transcriptional repressor in C2C12 cells.

Gal-GRIM1 is equally strong as a repressor as a large number of described corepressors such as, for example, Gal-HDAC1-10, Gal-CBF1, Gal-Alien and represses only insignificantly weaker than Gal-N-CoR-RD or Gal-SMRT-RD. The repression potential of Gal-GRIM1 was investigated in conjunction with the complex Gal4$_{3x}$-tk-LUC and Gal-MMTV-LUC promoter/reporter constructs and in conjunction with the minimal promoter/reporter constructs Gal$_{5x}$-E1b-TATA-box and Gal$_{3x}$-βglobin-TATA-LUC. In addition, the repression capacity of Gal-GRIM1 was investigated on an autonomous VP16 transactivation domain bound to DNA by means of LexA-DBD, via a LexA$_{8x}$-Gal$_{5x}$-LUC reporter (provided by Dr S. Khochbhin). The data obtained on Gal-GRIM1 has been tested experimentally in the following cell lines: A7r5, C2C12, CV1, BHK, 293, N2a, COS-7. FIG. 9 shows representative results for BHK and C2C12 cells.

Figure 10:
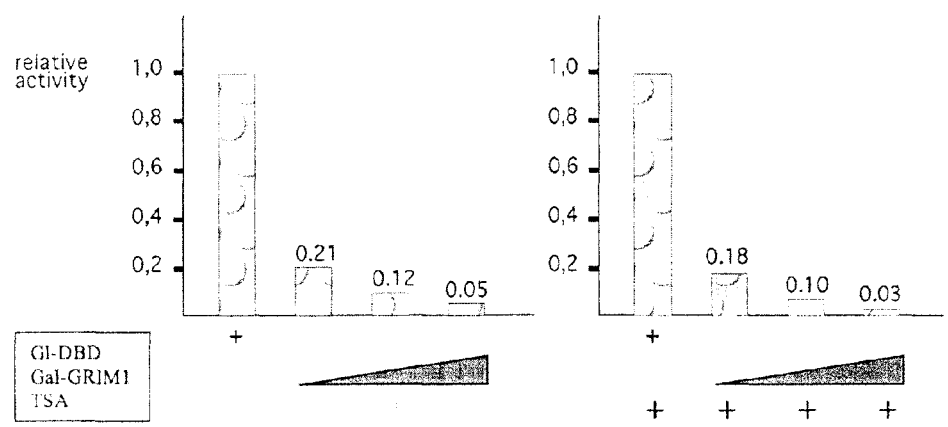
FIG. 10: The repression capacity of Gal-GRIM1 is not influenced by addition of the HDAC inhibitor trichostatin A (TSA). Transient transfections were carried out in BHK cells with a Gal4-tk-LUC reporter plasmid.

The Gal-GRIM1 repression is not impaired by addition of the specific histone deacetylase (HDAC) inhibitors trichostatin A (TSA, 300 nM) and of sodium butyrate (Na-But, 5 mM), suggesting that the mechanism of repression is fundamentally different from that described for other corepressors. Comparable cases have been described for other repressors, although no explanation of the method is described. In addition, the described factors show no involvement in skeletal muscle differentiation or adipogenesis. Data on the independence of HDACs in transient transfections are depicted in FIG. 10 for the example of BHK cells. The transcriptional activity of Gal-GRIM1 is uninfluenced by TSA in any cell line already tested.

To determine the GRIM1 domains involved in repression, a total of 11 deletion mutants of GRIM1 were constructed and all were tested in the Gal4-DBD context for their repression potential in all the reporter systems already described. All the GRIM1 domains used show transcriptional repression in the range from 2× (Gal-E and Gal-I) to 15-20× (full-length Gal-GRIM1). All the tested deletion mutants proved to be insensitive to HDAC inhibitors.

In summary, it was possible to show that GRIM1 has at least 5 independent repression domains, with the 3 main repression domains being located in the hydrophobic core region of the protein (mutQ, mutR, mutP). However, every analyzed deletion mutant shows a repression capacity which is significantly above the background in the Gal4-DBD context.

TABLE 8

Summarizing list of all hsGRIM1 deletion mutants used as Gal4-DBD fusion in transient transfections to investigate their repression potential.

| | aa |
|---|---|
| C-terminal deletion mutants | |
| mut A | 3-609 |
| mut B | 3-487 |
| mut C | 3-423 |
| mut D | 3-245 |
| mut E | 3-147 |
| N-terminal deletion mutants | |
| mut F | 145-749 |
| mut G | 246-749 |
| mut H | 485-749 |
| mut I | 609-749 |

TABLE 8-continued

Summarizing list of all hsGRIM1 deletion mutants used as Gal4-DBD fusion in transient transfections to investigate their repression potential.

| | aa |
|---|---|
| Intermediate deletion mutants | |
| mut J | 145-609 |
| mut N | 246-609 |
| mut O | 246-485 |
| mut P | 485-609 |
| mut Q | 246-423 |
| mut R | 423-485 |
| mut S | 145-245 |

Figure 11:
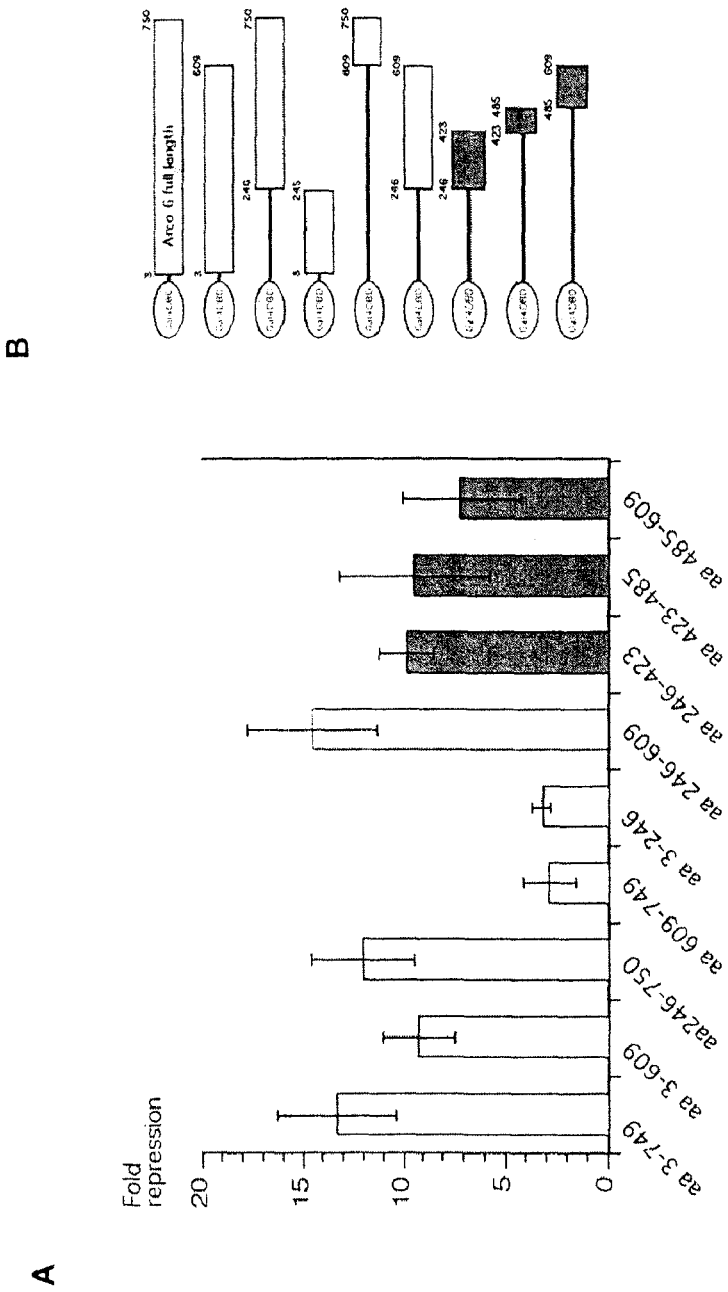
FIG. 11: Determination of the GRIM1 repressor domains by deletion analysis. A. Gal-GRIM1 deletion mutants were investigated for their repression potential in transient transfections. The central GRIM1 repressor domain is located in the region between aa 246-609 (depicted in white). The central RD can be divided further by further deletion studies into a total of three independent domains (depicted with dark shading). B. Schematic representation of Gal-GRIM1 deletion mutants.

The GRIM1 subdomains "E" and "I" described in the section "INHAT activity" show the smallest repressive effect as Gal4-DBD fusions in the transcriptional assays, but are involved in preventing histone acetylation by p300. No further information on the Q, P and R domains is available, and it was not possible to prove a direct involvement in the recruitment of additional corepressors by the interaction studies cited above. At the moment there is only speculation about the mechanism of repression used by GRIM1, although involvement of HDACs can be ruled out, and it appears that at least two different mechanisms are used (E and I in contrast to Q, R and P) (FIG. 11).

Results with the LexA$_{8x}$Gal$_{5x}$ system confirm these results but show a different relative repression of the individual fragments investigated (data not shown).

Full-length GRIM1 is able to repress both complex naturally occurring and synthetic minimal promoters.

Figure 12:
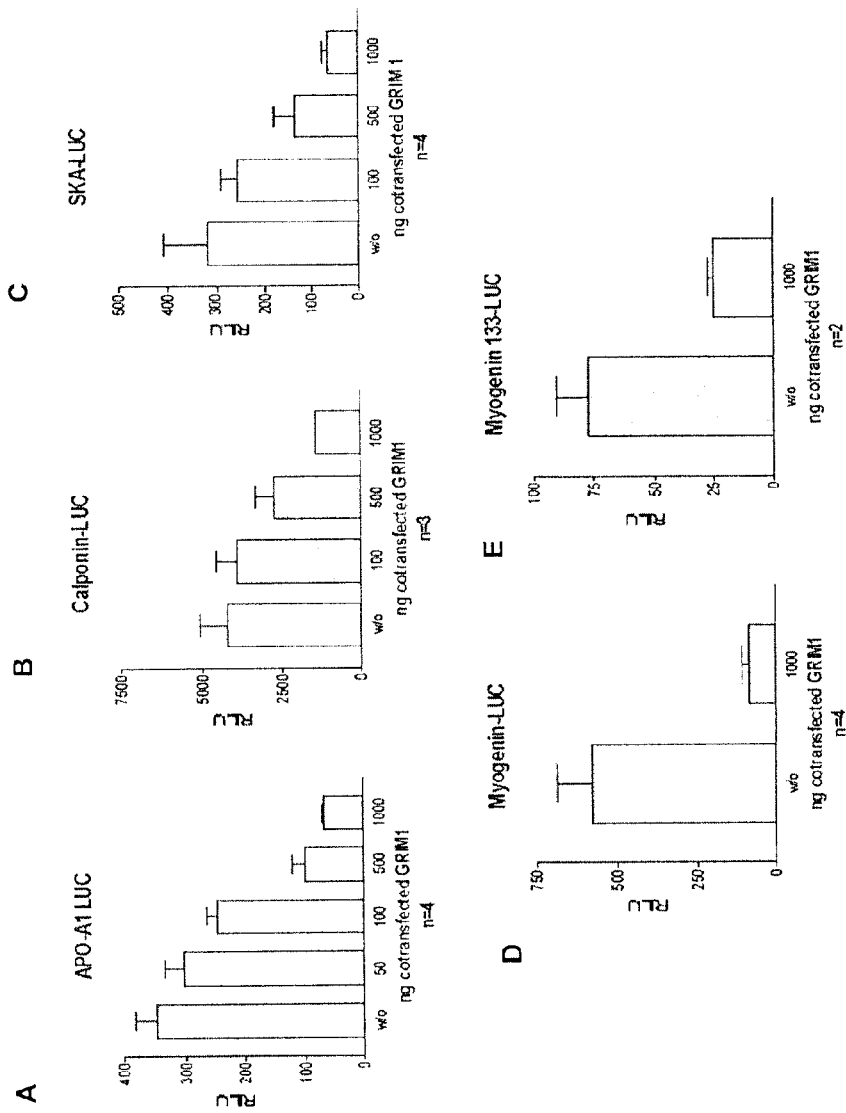
FIG. 12: GRIM1 represses various natural promoters in BHK cells. GRIM1 dose-dependently represses A. the ApoA1 promoter, B. the calponin (−3000) promoter, C. the SKA promoter, D. the myogenin promoter, and E. the myogenin promoter's proximal element (myogenin 133-LUC).
Figure 13:
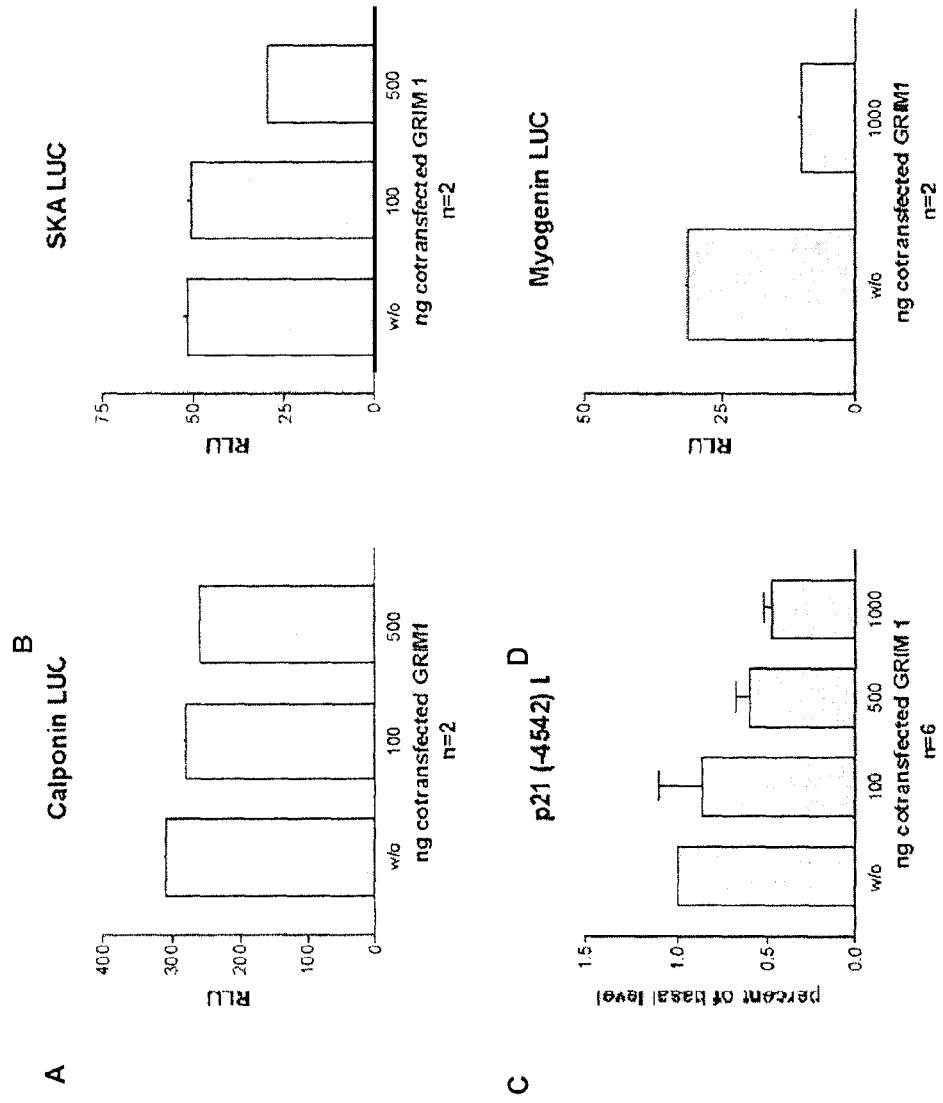
FIG. 13: GRIM1 represses various natural promoters in C2C12 cells. GRIM1 dose-dependently represses A. the calponin (−3000) promoter, B. the SKA promoter, C. the p21 (−4542) and D. the myogenin promoter.

The following systems have been tested in transient transfections: GRIM1 and complex promoters (p21 (−4542)LUC, SKA-LUC, calponin-LUC, myogenin-LUC, myogenin proximal promoter-LUC, thymidine kinase-LUC, probasin-LUC, MMTV-LUC and many more) (FIGS. 12 & 13).

Figure 14:
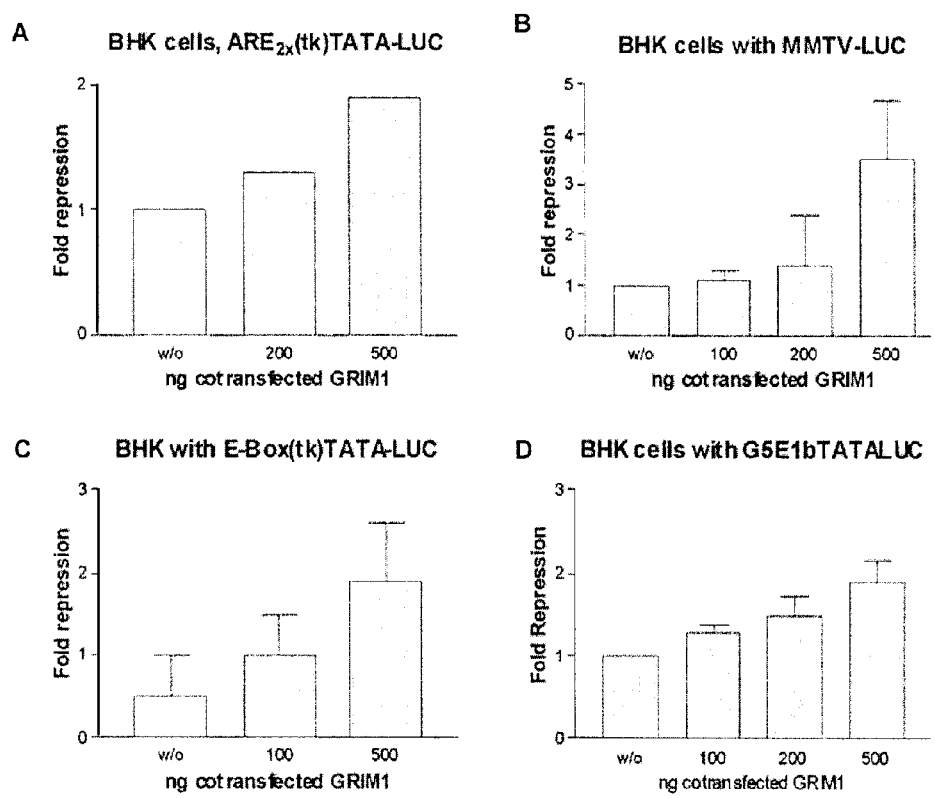
FIG. 14: GRIM1 represses minimal and complex promoters. 500 ng of reporter construct were used in transient transfections of BHK cells. A. ARE2x(tk)TATA-LUC is a minimal construct with 2 copies of an AR binding site in front of a thymidine kinase TATA box. B. MMTV-Luc is the complex Moloney mouse tumor virus promoter. C. E-Box(tk)TATA-LUC includes a binding site for the bHLH transcription factor SEF in the same context. D. G5E1bTATA-LUC is an adenovirus E1b TATA box-containing minimal construct with 5 Gal4 binding sites.

Cotransfections of GRIM1 and E1b-TATA-box-containing minimal promoters with synthetic TF binding sites (AR, Gal4 and SEF binding sites) or with the complex MMTV promoter leads to repression of basal transcriptional activity (all transfections shown were carried out in BBK cells) (FIG. 14). Repression of GRIM1 with minimal promoters without synthetic TF binding sites cannot be demonstrated more accurately owing to the low basal value of the constructs used.

Figure 15A:
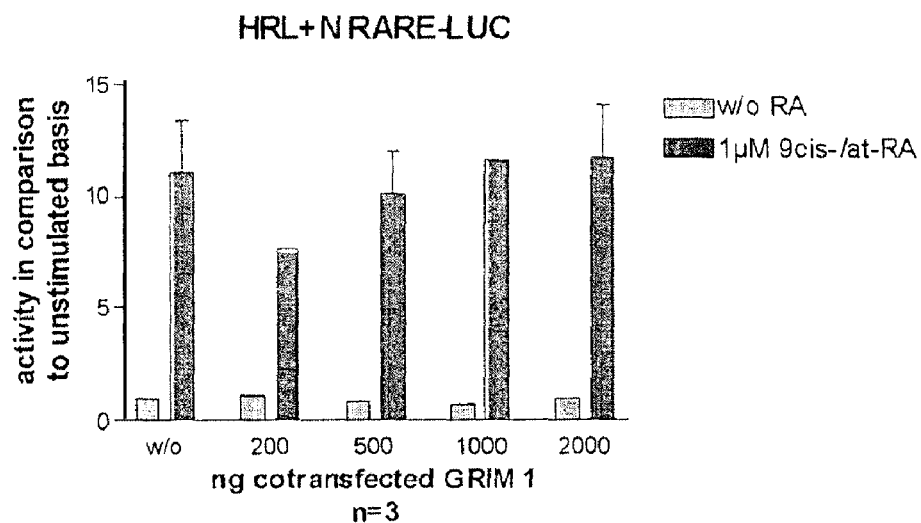
FIG. 15: GRIM1 does not repress any stably integrated luciferase reporter genes. A. HRL+N cells with stably integrated retinoic acid-inducible promoter. B. NIH3T3 cells with stably integrated CycA promoter-LUC. C. 293 cells with TPA-inducible NFkB promoter.
Figure 15B:
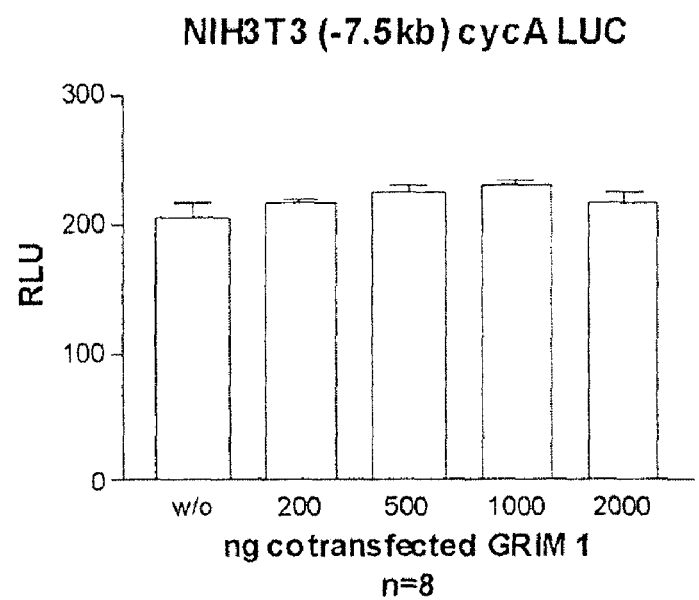
Figure 15C:
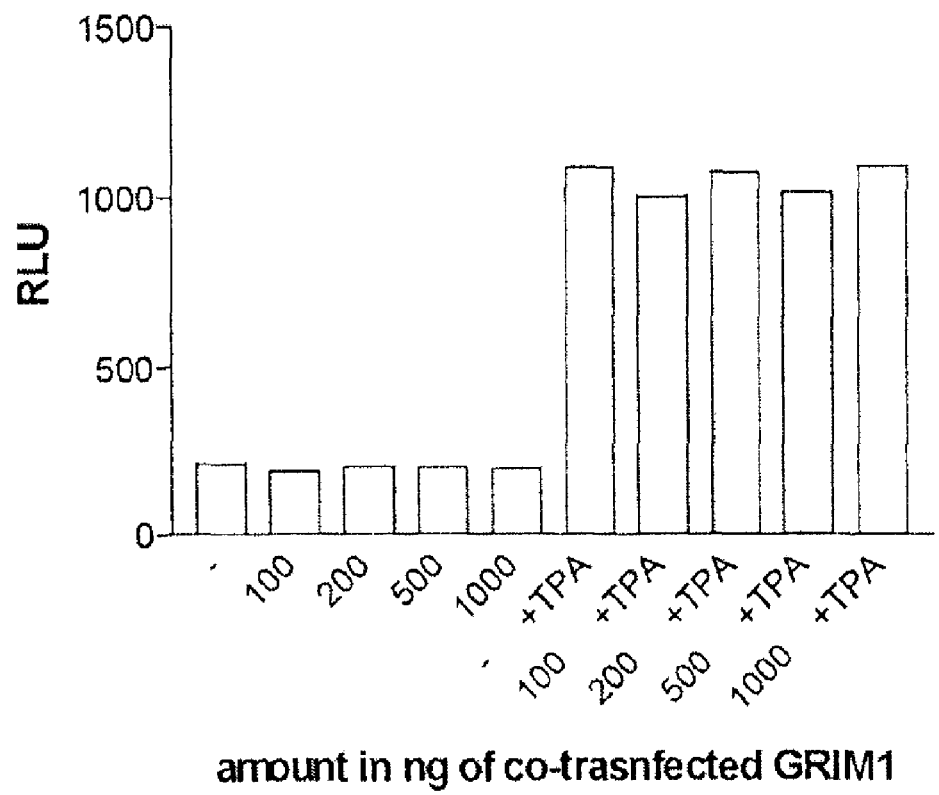

The repression potential of GRIM1 on promoter-luciferase-reporter constructs which have been stably integrated into the genome of the particular cell line (HRL+N with RARE$_{3x}$-LUC, NIH3T3 with cycA-LUC, 293 with NFkB-RE$_{4x}$-LUC) is summarized in FIG. 15. Transfection of the cells with GRIM1 shows no effect on reporter gene transcription in the induced and in the basal state.

In addition, direct effects of GRIM1 on various transcription factors were investigated in transient transfections (compare also Example 11). Besides the AR, in particular mmGCNF, mmERR1 and mmRVR were analyzed experimentally as full-length proteins with the corresponding reporter constructs for a functional interaction with GRIM1. No significant effect was observable in any of the transfections.

Interactions of GRIM1 with further transcription factors or cofactors was investigated in the Gal4-DBD-based context, with the respective Gal4-DBD-fused factor being cotransfected in constant amount with an increasing amount of wild-type GRIM1. Factors investigated in this system are: Gal4- p300, Gal4-DBD, Gal-Sp1-4, Gal4-CBF). Once again, no significant effect was observed in any of the transfections.

Example 13

Mechanism of GRIM1 Repression
a) HDAC Activity

Figure 16:
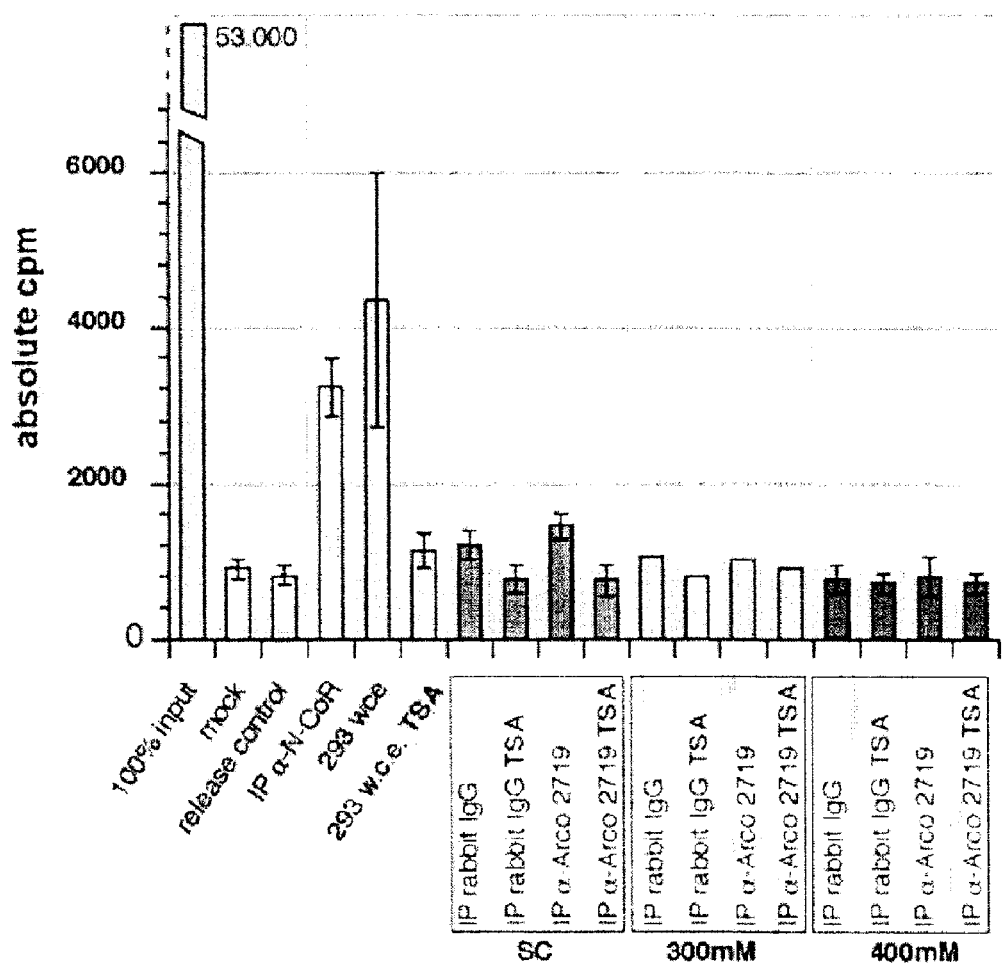
FIG. 16: GRIM1 has no endogenous or associated HDAC activity. Released radioactivity above the background of 850 cpm is assessed as HDAC activity. Samples were washed either 3 times physiologically (SC) or with increasing amounts of NaCl (300 and 400 mM). At 400 mM salt, it is assumed that no associated proteins were coprecipitated (confirmed by Western blotting and Ponceau stains). The figure summarizes 5 HDAC assays which were carried out independently. The name Arco which is used refers to the GRIM1 protein.

The mechanism of repression by recruitment of histone deacetylases (HDACs), which is the most widespread to date, appears not to be involved with GRIM1. The repression potential of Gal4-DBD-GRIM1 in transient transfections is not impaired by application of specific HDAC inhibitors in a concentration of up to 5-fold above the $K_D$ (final concentration of trichostatin A 300 nM, of sodium butyrate 5 mM). Immunoaffinity-purified and high-stringency-washed GRIM1 shows no endogenous HDAC activity. Nor do associated complexes which have been coimmunoprecipitated with GRIM1 by mild washing conditions show any HDAC activity. In addition, direct involvement in HDAC/N-CoR/SMRT complexes have been ruled out by Co-IP studies (FIG. 16).

b) INHAT Activity

A further possibility for transcriptional repression consists of direct masking of the histone N termini to prevent acetylation and thus loss of cohesion of the chromatin in the affected region. It was found by database analysis that the N terminus (aa 25-135) and the absolute C terminus (aa 638-749) of hsGRIM1 has acidic domains which display homology with a described INHAT domain of the Set protein. INHAT is an acronym for protein domains/proteins able to bind lysines and thus prevent histone acetylation.

It was possible to show in GST pulldown analyses that the N- and C-terminal fragments of hsGRIM1 can associate directly with histones in vitro. In addition, it can be shown in in vitro acetylation assays that recombinantly expressed GRIM1 aa 3-147 and aa 609-749 efficiently blocks acetylation of all four core histones (H3, H2A, $H_2B$ and H4) by p300. It was possible thereby to show that a possible mechanism of the GRIM1-mediated repression might be ensured by histone masking.

There are differences in the efficiency of inhibition of acetylation of individual histones by GRIM1. As yet, only blockage of acetylation of H2A and $H_2B$ have been unambiguously demonstrable.

c) Further Mechanisms of Repression
Lysine Methylation of Histones

Methylation of specific lysines in the free histone N termini (H3K9, H3K4) ensure compaction of the chromatin structure by preventing acetylation of the lysines which are important for regulation and thus preventing a loss of cohesion of the chromatin. In addition, methylated lysines represent a high-affinity binding site for the HP1 protein (heterochromatic protein 1). HP1 may subsequently recruit DNA methylases, MeCPs and also HDACs and lead to a targeted formation of transient or constitutive heterochromatin and thus repress transcriptional processes. Examples of HMTases described to date are Suv39h1, Suv39h2 and PRMT1.

Homology analyses show that no conserved SET domain responsible for histone methyltransferase (HMTase) activity is present in the GRIM1 sequence. It is therefore assumed that GRIM1 has no endogenous HMTase activity.

Recruitment of Chromatin-Reorganizing Complexes

A further possibility for specific repression would be targeted recruitment of chromatin-reorganizing complexes (e.g. ERG, SWI/SNF, CHRAC, ARC, RSC etc.). Promoter regions of the genes to be repressed can be wrapped up in compact chromatin by active chromatin reorganization in such a way that transcriptional initiation is distinctly impeded.

It is not possible to rule out a functional interaction of GRIM1 with one of the components of one of the remodeling complexes.

Blocking PIC Formation/Impeding the Initiation Reaction/Impeding Elongation

A further form of repression is impeding or preventing the formation of the preinitiation complex (PIC) at the start of transcription. Successful initiation is possible only if the TATA box-binding portion of TFIID can recruit the polymerase holocomplex at the starting point of transcription and if all the basal transcription factors involved are available in sufficient quantity. A further prerequisite for successful transcription is the need for the C terminus of RNAPII to be phosphorylated so that leaving of the initiation site is possible.

It is possible in an experiment familiar to the skilled worker to find whether GRIM1 directly interacts with one of the basal transcription factors or elongation factors and thus blocks efficient transcription (yeast two-hybrid system, pulldown analyses). No phosphatase domain can be found within the GRIM1 structure by homology analyses, and it is yet to be proven experimentally that GRIM1 is able to dephosphorylate RNAPII.

Titration Out of Coactivators by Binding to GRIM1

The potential of GRIM1 to inactivate basal or general coactivators by binding and thus to repress the initiation or elongation process is currently under investigation by searching for potential hsGRIM1 interactants.

A total of at least 5 independent repressor domains (RDs) have been found within the GRIM1 protein in transient transfections. The fragments E and I of GRIM1 showed the smallest repression potential in transient transfections, but their function in repression by GRIM1 was demonstrated in the INHAT analyses.

However, the deletion mutants P, Q, R and also S show a far stronger repression function in Gal-based transfections, suggesting further mechanisms beyond the known facts. It is possible to find the contribution to repression made by the other regions of GRIM1 by conventional experiments. These were intended to identify interacting GRIM1 partner proteins in order to find whether there is an association with non-HDAC components of transcriptional corepressor complexes.

Example 14

Analysis of Functional Motifs in hsGRIM1

Functional motifs within the hsGRIM1 structure were found by database homology analyses. A summary of the motifs found, their localization within the complete protein and the experimental strategy used is shown in the following table.

TABLE 9

Summary of the functional motifs of hsGRIM1.

| Name | Sequence | aa position | Detection |
|------|----------|-------------|-----------|
| LxxLL | I RD LI | 212-216 | Significance not yet |
|  | L QN LL | 219-223 | confirmed |
|  | L AF LV | 312-316 | experimentally |
|  | L TE LL | 362-366 |  |
|  | II GC I | 339-443 |  |
|  | L PF IL | 476-480 |  |
|  | IL RP L | 686-690 |  |

TABLE 9-continued

Summary of the functional motifs of hsGRIM1.

| Name | Sequence | aa position | Detection |
|---|---|---|---|
| NES | L RV L AF L V L | 309-317 | Detected by GFP relocation experiments and directed point mutagenesis |
| NLS | KRRK MAD RK DED RK QF R | 649-666 | Detected by directed point mutagenesis and GFP-GRIM1 localization |
| CoRNR Box | P L AQV IIGCI K LI P | 435-446 | Not yet confirmed experimentally. Has no influence on AR-dependent interactions |
| HMG Box like | poly E/ poly D | 25-51 68-134 658-683 697-749 | INHAT acitivity of the investigated fragments. Direct DNA and/or histone binding not yet confirmed experimentally. |

LxxLL: interaction motif by which coactivators interact with NHRs.
NES: nuclear export signal.
NLS: nuclear localization signal.
CoRNR box: interation motif by which corepressors interact with NHRs.
HMG box: contact of HMG proteins to DNA and to histones.

Detection of the NES within hsGRIM1

Figure 17:
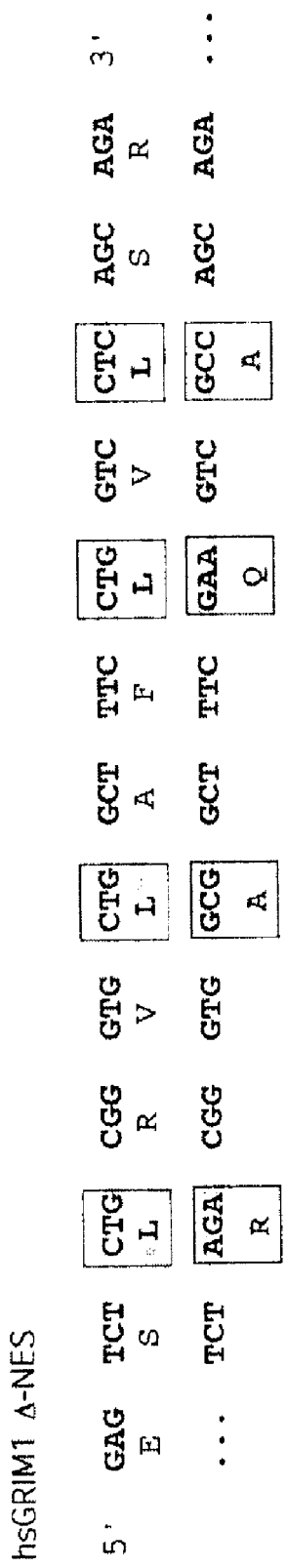
FIG. 17: Directed mutagenesis to inactivate the four lysines involved in the NES (SEQ ID NOS 19-21 are disclosed respectively in order of appearance).

For direct analysis of the motif, all four relevant lysines were inactivated by directed point mutagenesis so that the α-helical structure of the NES was destroyed. The inactivating mutations are depicted in FIG. 17. A directed inactivation of the two 3'-located lysines on its own proved to be insufficient to destroy the functionality of the NES.

Figure 18:
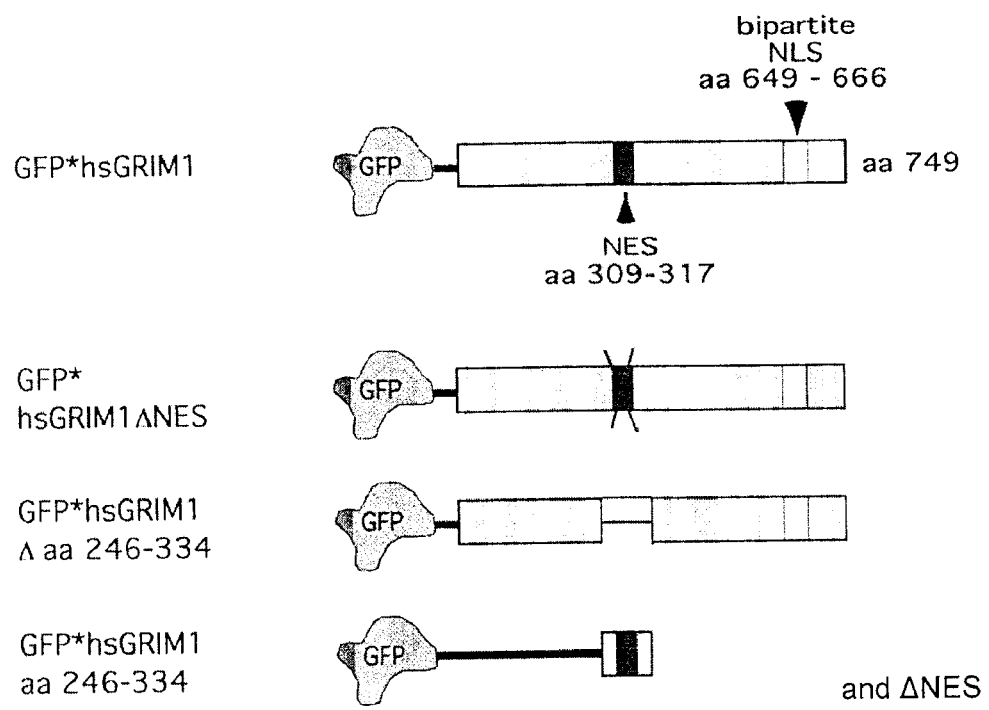
FIG. 18: GFP fusion proteins used to demonstrate the functionality of the nuclear export signal (NES). ANES characterizes the point mutations described above.

To demonstrate the functionality of the export signal, hsGRIM1 protein fragments were fused to GFP (green fluorescent protein) (depicted in FIG. 18) and expressed in cells by transient transfection. The localization of the respective fragments was detected by fluorescence microscopy.

Only GFP showed a pan-cellular localization. Full-length GFP-hsGRIM1 was located exclusively in the nucleus through the dominance of the NLS, as were the NES deletion mutant and the fragment from which a region flanking the NES had been deleted (hsGRIM1 Δaa246-334). On fusion of the hsGRIM1 fragment which contains the NES to GFP (hsGRIM1 aa246-334), the resulting protein was located exclusively in the cytoplasm. On coupling of the point-mutated fragment of aa 246-334 to GFP, the pan-cellular localization was restored so that it was possible to demonstrate the functionality of the motif.

Detection of the NLS within hsGRIM1

Figure 19:
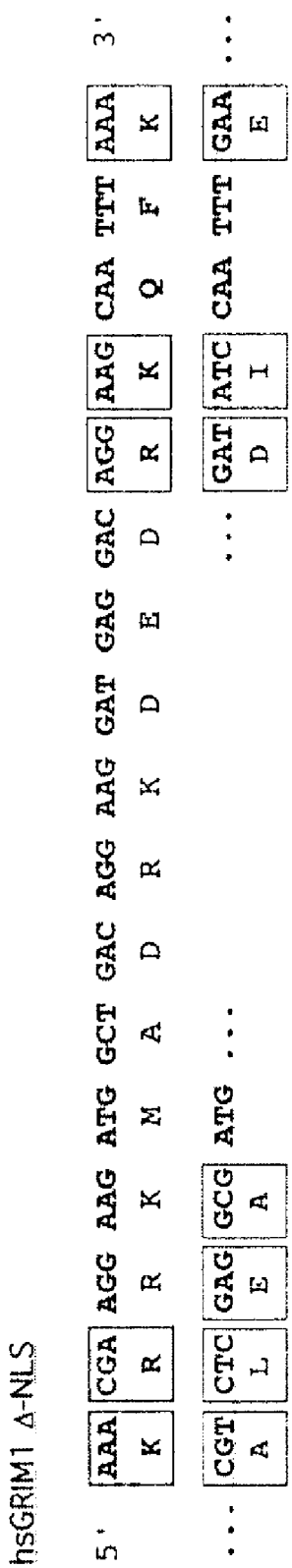
FIG. 19: Directed mutagenesis for inactivation of the seven basic residues involved in the NLS (SEQ ID NOS 22-26 are disclosed respectively in order of appearance).

To analyze the motif, besides the deletion mutants detailed hereinafter, all seven relevant basic residues were inactivated by directed point mutagenesis (FIG. 19). Inactivation of the 3'-located 3 basic residues alone proved to be insufficient to inactivate the NLS.

Figure 20:
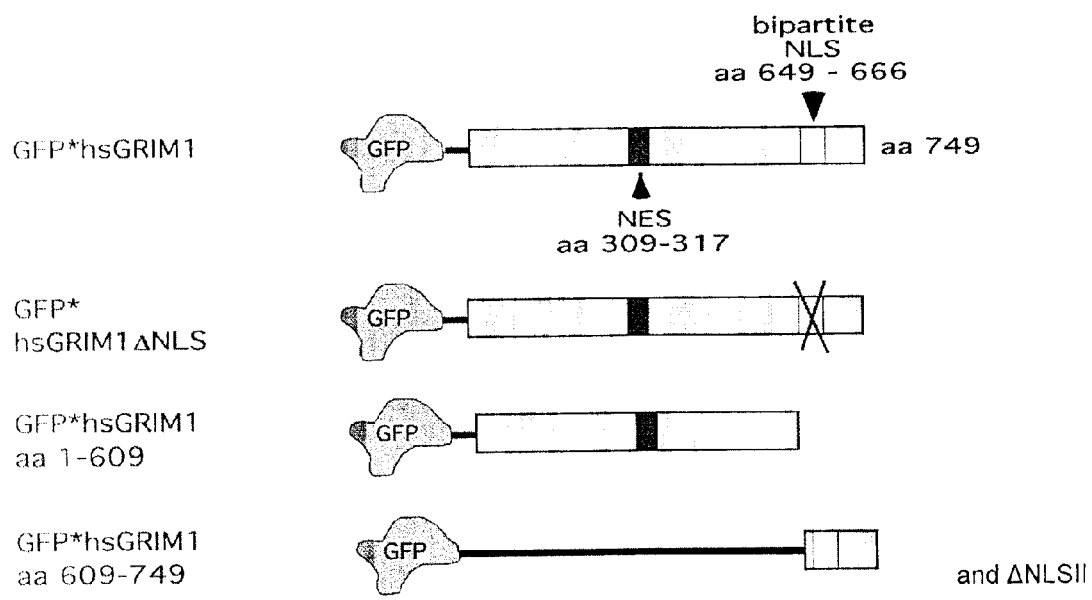
FIG. 20: GFP fusion proteins used to demonstrate the functionality of the nuclear localization signal (NLS).

To demonstrate the functionality of the import signal, hsGRIM1 protein fragments were fused to GFP (depicted in FIG. 20) and expressed in cells by transient transfection. The localization of the respective fragments was detected by fluorescence microscopy.

Only GFP showed a pan-cellular localization. Full-length GFP-hsGRIM1 was located exclusively in the nucleus. On deletion of the last 140 amino acids (hsGRIM1 aa1-609), the GFP fusion protein showed both a cytoplasmic and a weak nuclear localization, while the corresponding counterpart fused to GFP (GFP-hsGRIM1 aa609-749) shows an exclusively nuclear localization. The full-length hsGRIM1 with the seven-fold point mutation within the NLS showed the same distribution pattern as the hsGRIM1 aa1-609 deletion mutant and confirmed the functionality of the NLS. On coupling of the point-mutated fragment of aa609-749 to GFP, the fusion protein was likewise located in the cytoplasm.

Detection of the CoRNR box within hsGRIM1

To analyze the CoRNR box, all three highly conserved and necessary isoleucines in the hydrophobic core of the helix were replaced by alanines or by a serine: I436A, I437S, I444A. Further functional characterization of the point mutations made have revealed to date only that the repression potential of hsGRIM1 is not impaired, and that the interaction with the AR is not impaired by destroying the CoRNR box.

Intracellular Relocalization of mmGRIM1 in Cell Culture-Based Differentiation Models GRIM1 shows a change in its subcellular localization during specific differentiation processes. In cell culture systems, GRIM1 is transported from the nucleus into the surrounding cytoplasm during skeletal muscle differentiation of mouse C2C12 cells. The timeframe for the observed translocation of GRIM1 is in the range for the expression of the myogenic bHLH transcription factor myogenin (My14) and of the structural protein skeletal muscle myosin heavy chain (MHC), i.e. at a more advanced time during muscle differentiation than previously described factors such as HDAC4, HDAC5 and HDAC7. C2C12 cells differentiate under low-serum conditions within 6-8 days from proliferating myoblasts to fused, multinuclear myotubes. During this, the cells undergo a $G_0$ arrest, the CDK inhibitor p21 is upregulated, and an ordered cascade of myogenic transcription factors such as Myf5, MyoD and myogenin provide the transcriptional precondition for myogenesis. In differentiating C2C12 skeletal muscle cells, GRIM1 leaves the nuclei of fused myotubes after about 6 to 8 days, whereas GRIM1 is always located in the nucleus in mononuclear myoblasts. Expression of the structural protein of muscle MHC takes place at the time when the first GRIM1-free nuclei are to be observed, and was used in IIFs as temporal marker for GRIM relocalization.

The data determined for C2C12 also apply to other cellular skeletal muscle differentiation systems. The same effect was also detectable in rat L6 skeletal muscle cells. The cells have different differentiation kinetics and do not fuse until day 10-12 in differentiation medium (DM). GRIM1 also relocalizes in L6 cells, and GRIM1-free nuclei are detectable only from day 16 onwards in DM. In a further differentiation system, mouse 10T1/2 fibroblasts were stably transfected with an estrogen-inducible MyoD expression cassette (cells kindly made available by Dr. D. Bergstrom). Addition of 1 μM estradiol enables skeletal muscle differentiation via MyoD expression. After only about 3-4 days in DM, many cells can be detected as multinuclear myotubes.

During skeletal muscle differentiation, the GRIM1 protein is not degraded and/or broken down but is present to the full extent also in the cytoplasm. GRIM1 immunoreactivity can be detected unchanged in Western blot analyses with whole cell extracts of C2C12 cell extracts which have been differentiated to myotubes in DM for 8 days (on day 8 after addition of DM, ≧60% of all the cells present were myotubes). The results can also be further confirmed by cell fractionations. In addition, RT-PCR analyses have confirmed that the amount of mmGRIM1-mRNA is not changed during C2C12 differentiation.

As a further check, it was investigated whether GRIM1 also experiences subcellular relocalization during smooth muscle differentiation. For this purpose, mouse smooth muscle cells were obtained ex vivo and dedifferentiated by growth factor addition. Cells were additionally differentiated again further to smooth muscle cells via differentiation medium in vitro. The results show that GRIM1 does not leave the nucleus during smooth muscle differentiation. In addition, a cell culture smooth muscle differentiation system (Monc-1 cells) was used in order to obtain in vitro data about possible GRIM1 relocalization. As already shown for the ex vivo cells, no GRIM1 relocalization in smooth muscle cells was observable during the investigated differentiation times.

A further in vitro differentiation model used for GRIM1 relocalization analyses is differentiation of 3T3-L1 preadipocytes to mature fat cells. In the total of three differentiation protocols carried out, GRIM1 twice showed a detectable relocalization from the core into the cytoplasm, while in one case no change in the localization of the GRIM1 immunoreactivity was detectable. Western blot analyses have shown that no decrease in GRIM1 immunoreactivity in whole-cell extracts was detectable in any of the three protocols.

Example 15

Regulation of GRIM1 Function

Complete experimental results are not yet available on the regulation of GRIM1 function and on signal pathways which might be involved in the subcellular relocalization of GRIM1. No signal pathway modulating the transcriptional activity of GRIM1 has yet been unambiguously identifiable. Nor is there any experimental evidence of involvement of a signal cascade intervening in the GRIM1 relocalization process. The data available on this topic can be briefly summarized below.

Transcriptional Activity:

In the direct vicinity of the NES within the GRIM1 sequence there is a consensus PKC phosphorylation site (serine 308). The transcriptional activity of Gal-GRIM1 was investigated in transient transfections in various cell lines. Neither the treatment of the cells with the specific PKC inhibitor Gö6850 (Parke-Davis, formerly Gödecke AG) nor a stimulation with the PKC-activating agent TPA brought about a change in the transcriptional activity.

The sole experimental evidence for modification of GRIM1 is the detection of direct acetylation of GRIM1 (aa3-147 and of full-length GRIM1) by the HAT domain of p300.

Cotransfection of full-length p300 and Gal-GRIM1 shows no change in the repression pattern, and addition of trichostatin A (TSA) enhances general transcription but relative repression by Gal-GRIM1 remains unchanged.

Cotransfection of Gal-GRIM1 in combination with a constitutively active version of Rho GTPase (RhoAV14) likewise shows no change in the activity.

Relocalization:

Nuclear export of GFP-GRIM1 or of the mutant GFP-GRIM1 aa234-336 is not influenced by treatment of the cells with the bacterial toxin leptomycin B (LMB, 20 nM for 6 h before cell harvesting and analysis by IIF). LMB is a specific inhibitor of the export factor exportin1/Crm1, so that it can be concluded from the experiment that there must be an exportin-independent transport mechanism.

14-3-3 proteins are responsible for active removal of the HDACs 4, 5 and 7 from the nucleus and retention in the cytoplasm during muscle differentiation. It was possible by Co-IP studies to rule out an interaction between GRIM1 and 14-3-3 proteins (family members zeta, beta, tau).

Treatment of differentiating C2C12 skeletal muscle cells with various inhibitors of central signal transduction pathways have no effect on relocalization or the number of nuclear speckles of GRIM1 within the investigated differentiation from day 0 to day 6 after addition of the differentiation medium. Tested inhibitors: pan-HDAC inhibitors TSA and sodium butyrate, protein kinase inhibitors Gö6850 (specific PKC inhibitor, 1 µM), LY294002 (specific PI3kinase inhibitor, 10 µM), Ro31-8220 (PKC broad-spectrum inhibitor, 0.5 µM), PD98059 (MEK1 inhibitor, 10 µM), fasudil (Rock kinase inhibitor, 10 µM), SB203580 (p38α/β inhibitor). Overacetylation and blockade of central signal cascades had drastic morphologically visible consequences for some of the cells, but there was no effect on relocalization or the number of detectable GRIM1 speckles.

Example 16

Interaction of hsGRIM1 and the Androgen Receptor (AR) and Functional Consequences Resulting Therefrom It was possible to demonstrate in a yeast two-hybrid interaction assay that GRIM1 interacts with the nuclear hormone receptor androgen receptor (AR). The GRIM1 interaction domain in the yeast-based assay is located in the C terminus between aa 606 to 749. Further functional characterization of the interaction domains within GRIM1 was carried out by pulldown analyses with the expressible fragments of GRIM1. The interaction of GRIM1 with the AR is independent of the type of ligand used (agonists, antagonists or no ligands). The available data are summarized in FIG. 21.

The C terminus of GRIM1 shows, in contrast to the data obtained in yeast, no in vitro interaction with the AR, but the fragment from aa 460 to aa 609 shows a strong interaction independent of the ligand used.

The interaction between the AR and GRIM1 was likewise detectable in in vivo interaction assays. In co-immunoprecipitations, the interaction between GRIM1 and the AR was likewise ligand-independent and could not be significantly blocked even in washing buffer with 400 mM NaCl. It was possible to show the interaction with IP studies using antibodies both against the AR and against GRIM1.

The AR is a member of the superfamily of ligand-activatable nuclear hormone receptors. After binding of the natural AR ligand 5α-dihydrotestosterone, the AR is transported from the cytoplasm into the nucleus and brings about transcriptional activation of its target genes. Besides the activating ligands, each receptor has specific antagonists which likewise bring about translocation into the nucleus, but bring about a repressive conformation of the receptor ligand binding domain. Antagonist-bound receptor is able to recruit corepressor complexes and actively repress transcription. However, in some cell lines or in certain pathological situations, antagonists may become partial agonists and unnaturally bring about a transactivation by the receptor. It is known in the case of the AR that substances employed therapeutically for prostate carcinomas, such as cyproterone acetate, Casodex or hydroxyflutamide, may have partial agonistic effects in hormone-refractory tumors.

Figure 22:
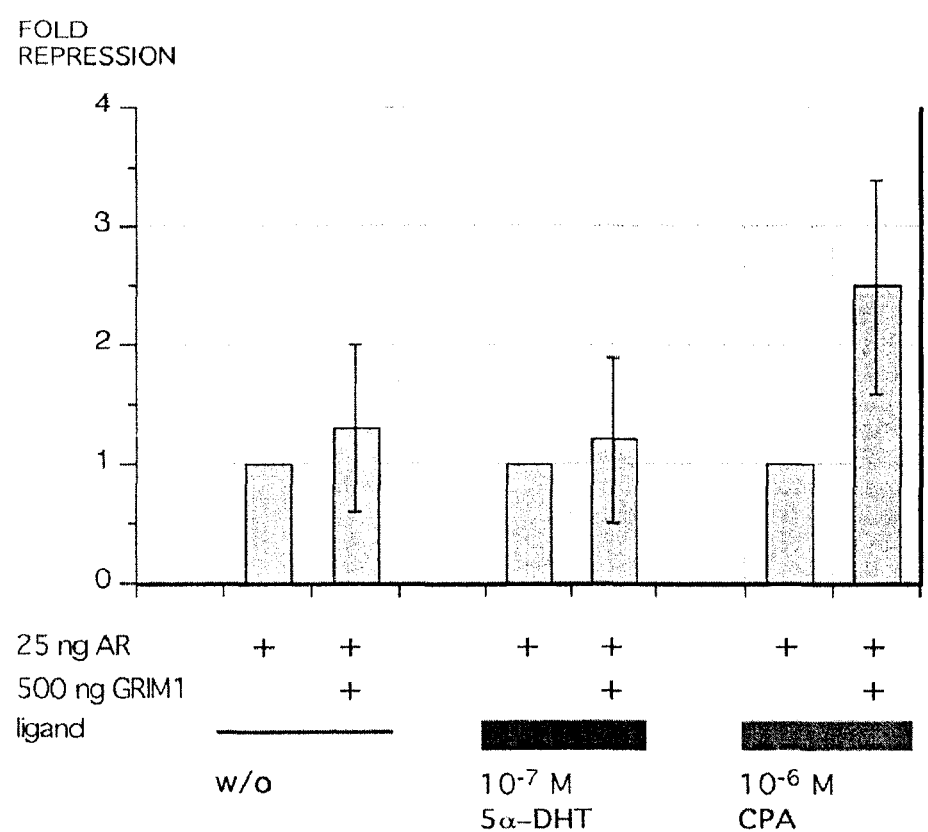
FIG. 22: GRIM1 selectively represses antagonist-activated AR.

It was possible to show in the cell culture system that GRIM1 is able specifically to repress an AR transactivation brought about by CPA, Casodex or OH-flutamide. Non-liganded or DHT-loaded AR is not transcriptionally affected by GRIM1. The observed effect varies in the range between 2-3-fold repression of the CPA-induced AR transactivation (FIG. 22).

Transient transfections were carried out in BHK cells in which the antagonists used act as partial agonists. A minimal promoter with synthetic AR binding sites was used as reporter (ARE$_{2x}$-(tk)TATA-LUC). The same effect was obtained on use of 1 µM Casodex or OH-flutamide instead of 1 µM CPA.

Figure 23:
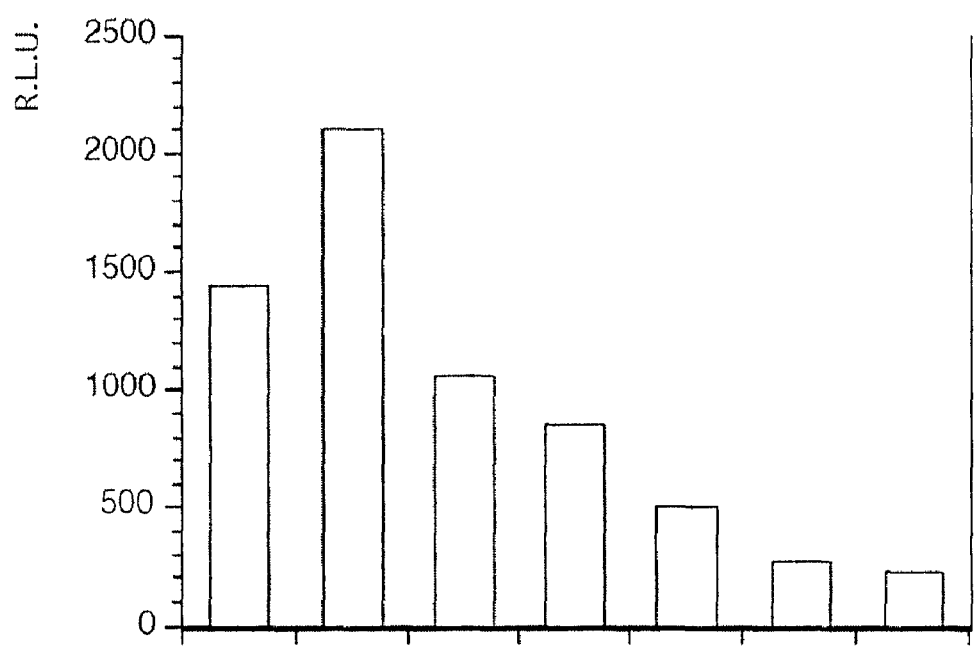
FIG. 23: GRIM1 represses CPA-loaded and TIF2 superactivated androgen receptor. Transient transfections were carried out in BHK cells in which CPA (1 μM) acts as partial agonist. $ARE_{2x}$-(tk)TATA-LUC was used as reporter.

A further indication of the functionality of the effect is that the superactivation of the CPA-loaded AR by the coactivator TIF2 in BHK cells can be repressed or at least markedly restricted by cotransfection of GRIM1 (FIG. 23).

The invention claimed is:

1. A method of assessing the differentiation of a skeletal muscle cell or an adipose cell comprising detecting the subcellular localization of SEQ ID NO: 3 in said cells to determine if SEQ ID NO: 3 is present in the cytoplasm or the nucleus, and assessing the differentiation of the cells based upon whether said SEQ ID NO: 3 is detected in the cytoplasm or the nucleus of said cells, wherein the relocalization of SEQ ID NO: 3 from the nucleus to the cytoplasm correlates with the differentiation of said cells, and wherein SEQ ID NO: 3 is detected with an antibody that binds to SEQ ID NO: 3.

2. The method of claim 1, wherein when said SEQ ID NO: 3 is detected in the cytoplasm of said cell, the cell is differentiated.

3. The method of claim 1, wherein when said SEQ ID NO: 3 is detected in the cytoplasm of said cell, but is not detected in the nucleus of said cell, the cell is differentiated.

4. The method of claim 1, wherein when SEQ ID NO: 3 is detected in the nuclei of said cell, the cell is not differentiated.

5. The method of claim 1, wherein said SEQ ID NO:3 is detected with a detectably labelled antibody that binds SEQ ID NO: 3.

6. The method of claim 5, wherein said antibody is labelled with an enzyme.

7. The method of claim 5, wherein the antibody is labelled with a fluorescein label.

8. A method of assessing the differentiation of a skeletal muscle cell or an adipose cell comprising detecting the subcellular localization of SEQ ID NO: 3 in said cells to determine if SEQ ID NO: 3 is present in the cytoplasm, wherein detection of SEQ ID NO: 3 in the cytoplasm of said cells correlates with the cells being differentiated, and wherein SEQ ID NO: 3 is detected with an antibody that binds to SEQ ID NO: 3.

9. A method of assessing the differentiation of a skeletal muscle cell or an adipose cell comprising detecting the subcellular localization of SEQ ID NO: 3 in said cells to determine if SEQ ID NO: 3 is present in the cytoplasm or the nucleus, wherein detection of SEQ ID NO: 3 in the cytoplasm and not the nucleus of said cells correlates with the cells being differentiated, and wherein SEQ ID NO: 3 is detected with an antibody that binds to SEQ ID NO: 3.

10. A method of assessing the differentiation of a skeletal muscle cell or an adipose cell comprising detecting the subcellular localization of SEQ ID NO: 3 in said cells to determine if SEQ ID NO: 3 is present in the nucleus, wherein detection of SEQ ID NO: 3 in the nucleus of said cells correlates with the cells not being differentiated, and wherein SEQ ID NO: 3 is detected with an antibody that binds to SEQ ID NO: 3.

* * * * *